(12) United States Patent
Yamazaki et al.

(10) Patent No.: US 9,201,168 B2
(45) Date of Patent: Dec. 1, 2015

(54) POLYMERIZABLE INORGANIC-PARTICLE DISPERSANT, INORGANIC-ORGANIC COMPOSITE PARTICLES CONTAINING SAID POLYMERIZABLE INORGANIC-PARTICLE DISPERSANT, AND INORGANIC-ORGANIC RESIN COMPOSITE MATERIAL

(71) Applicant: NIPPON KASEI CHEMICAL COMPANY LIMITED, Iwaki-shi (JP)

(72) Inventors: Masanori Yamazaki, Kanagawa (JP); Naoko Sumitani, Kanagawa (JP); Ritsuko Yamauchi, Kanagawa (JP); Tomoko Maeda, Kanagawa (JP); Takako Takahashi, Kanagawa (JP)

(73) Assignee: NIPPON KASEI CHEMICAL COMPANY LIMITED, Iwaki-shi (JP)

( * ) Notice: Subject to any disclaimer, the term of this patent is extended or adjusted under 35 U.S.C. 154(b) by 0 days.

(21) Appl. No.: 14/230,862

(22) Filed: Mar. 31, 2014

(65) Prior Publication Data
US 2014/0213725 A1 Jul. 31, 2014

Related U.S. Application Data

(63) Continuation of application No. PCT/JP2012/075153, filed on Sep. 28, 2012.

(30) Foreign Application Priority Data

Sep. 30, 2011 (JP) ................................. 2011-217350

(51) Int. Cl.
| | | |
|---|---|---|
| G02B 1/04 | (2006.01) | |
| C08F 20/38 | (2006.01) | |
| C09D 133/14 | (2006.01) | |
| C07F 9/6553 | (2006.01) | |
| C07F 9/6561 | (2006.01) | |
| C07F 9/09 | (2006.01) | |
| C07F 9/165 | (2006.01) | |
| C07F 9/30 | (2006.01) | |

(52) U.S. Cl.
CPC . *G02B 1/04* (2013.01); *C07F 9/091* (2013.01); *C07F 9/098* (2013.01); *C07F 9/1651* (2013.01); *C07F 9/1658* (2013.01); *C07F 9/301* (2013.01); *C07F 9/6561* (2013.01); *C07F 9/655345* (2013.01); *C07F 9/655363* (2013.01); *C08F 20/38* (2013.01); *C09D 133/14* (2013.01)

(58) Field of Classification Search
CPC ........................................................ G02B 1/04
USPC ................. 526/256, 277; 549/5, 20
See application file for complete search history.

(56) References Cited

U.S. PATENT DOCUMENTS

| | | | | |
|---|---|---|---|---|
| 5,055,497 A | * | 10/1991 | Okada et al. .................. | 523/116 |
| 5,457,172 A | * | 10/1995 | Curci et al. .................... | 526/240 |
| 6,646,104 B1 | | 11/2003 | Mori et al. | |
| 2009/0128912 A1 | | 5/2009 | Okada et al. | |
| 2009/0317541 A1 | | 12/2009 | Ito et al. | |
| 2010/0104842 A1 | | 4/2010 | Suzuki et al. | |

FOREIGN PATENT DOCUMENTS

| | | |
|---|---|---|
| JP | 04-161411 | 6/1992 |
| JP | 8-57864 | 3/1996 |
| JP | 2008-94732 | 4/2008 |
| JP | 2008-239922 | 10/2008 |
| JP | 2009-29939 | 2/2009 |
| JP | 2009/209277 | 9/2009 |
| JP | 2010-30993 | 2/2010 |
| JP | 2010-84122 | 4/2010 |
| WO | 01/40175 | 6/2001 |
| WO | 2007/032217 | 3/2007 |

OTHER PUBLICATIONS

Extended European Search Report issued Jan. 14, 2015 in Patent Application No. 12836023.7.

Seiichi Takano, et al., "New Synthesis of (+)-Meroquinene Aldehyde and its Epimer from (+)-Norcamphor" Journal of the Chemical Society, Chemical Communications, No. 13. XP55157035, 1979, pp. 556-557.

Mitsuhiro Kawamura, et al., "Enantio- and Stereocontrolled Syntheses of (−)-Semburin, (+)-N-Benzoylmeroquinene Aldehyde, (−)-Antirhine, and (+)-Isocorynantheol from Common (+)-Norcamphor" Tetrahedron Letters, vol. 36, No. 19, XP004028133, 1995, pp. 3369-3372.

International Search Report issued Jan. 8, 2013 in PCT/JP2012/075153 filed Sep. 28, 2012.

Combined Chinese Office Action and Search Report issued Mar. 3, 2015 in Patent Application No. 201280047364.4 (with English language translation and English translation of categories of cited documents).

\* cited by examiner

*Primary Examiner* — Tae H Yoon
(74) *Attorney, Agent, or Firm* — Oblon, McClelland, Maier & Neustadt, L.L.P.

(57) ABSTRACT

The present invention provides a polymerizable inorganic particle dispersant that can achieve an inorganic-organic composite particle and inorganic-organic resin composite material, which have a high refractive index and a high Abbe's number, i.e., which can achieve both of a high refractive index and a high Abbe's number that is non-conventional in a composite with an inorganic particle. The present invention relates to a polymerizable inorganic particle dispersant comprising a compound which includes the following functional groups A, B and Q: A: Polymerizable functional group; B: Carboxyl group, Oxo acid group containing a phosphorous or Oxo acid group containing sulfur; and C: Sulfur-containing divalent or more aliphatic hydrocarbon group, which may contain a hetero atom other than sulfur.

23 Claims, No Drawings

POLYMERIZABLE INORGANIC-PARTICLE DISPERSANT, INORGANIC-ORGANIC COMPOSITE PARTICLES CONTAINING SAID POLYMERIZABLE INORGANIC-PARTICLE DISPERSANT, AND INORGANIC-ORGANIC RESIN COMPOSITE MATERIAL

CROSS-REFERENCE TO RELATED APPLICATIONS

This application is a Continuation of PCT/JP2012/075153 filed on Sep. 28, 2012. This application is based upon and claims the benefit of priority to Japanese Application No. 2011-217350 filed on Sep. 30, 2011, the entire contents of which are incorporated herein by reference.

TECHNICAL FIELD

The present invention relates to a polymerizable inorganic-particle dispersant having a high refractive index and a high Abbe's number, inorganic-organic composite particles including the polymerizable inorganic-particle dispersant, and an inorganic-organic resin composite material. More particularly, the invention relates to a polymerizable inorganic-particle dispersant that itself has a high refractive index and a high Abbe's number and that is capable of providing a composite material composition combining a high refractive index and a high Abbe's number, which are inconsistent performances, and to inorganic-organic composite particles including the polymerizable inorganic-particle dispersant, an inorganic-organic resin composite material, and an optical material including the inorganic-organic resin composite material. The invention further relates to a novel compound which combines a high refractive index and a high Abbe's number.

BACKGROUND ART

In recent years, plastic materials which are lightweight, have high impact resistance, and can be efficiently produced have come to be frequently used in place of inorganic glasses in personal digital assistants including cell phones, flat panel displays (FPD), lens materials, optical fibers, etc.

In fields where high refractive indexes are required, among those applications, there is a desire for a material which changes little in refractive index with changing wavelength (material having a high Abbe's number), not to mention increases in the refractive index of materials. In plastic materials, however, refractive index and Abbe's number are inconsistent with each other, and it has been difficult to simultaneously satisfy these two properties.

In order to mitigate such problems of organic materials, hybrid materials obtained by compositing an organic material with an inorganic material on a molecular level are being investigated in recent years. Specifically, hybrid materials obtained by dispersing metal oxide nanoparticles [titanium oxide (refractive index: 2.5-2.7), zirconium oxide (refractive index: 2.1-2.2), or barium titanate (refractive index: 2.4)] in organic materials in such a manner as to result in transparency, for the purpose of imparting a high refractive index, mechanical strength, etc. to the organic materials, are being investigated.

In such hybrid materials, it has been necessary to set the Abbe's number of the resin serving as the matrix to a high value in order to attain a high Abbe's number. However, Abbe's number and refractive index are inconsistent with each other in resins, and resins having a high Abbe's number have the property of being low in refractive index. Consequently, for obtaining a hybrid material having an increased refractive index, it has been necessary to disperse a large amount of metal oxide nanoparticles in a resin serving as a matrix.

For example, patent document 1 states that a hybrid material was produced from zirconium oxide and an acrylic resin and that a refractive index $n_d$ of 1.67 and an Abbe's number $v_d$ of 43 were attained when the amount of the zirconium oxide incorporated into the hybrid material was 30% by volume (about 70% by mass).

Meanwhile, a material which combines a high refractive index and a high Abbe's number on the basis of the matrix resin alone has also been proposed. For example, patent document 2 states that a high refractive index (589 nm D-line: 1.6859) and a high Abbe's number (48.6) can be attained with a polymeric material obtained by subjecting 1,4-dithiane-2,5-dithiol and divinyl sulfone to Michael addition polymerization.

Furthermore, patent document 3 states that a high refractive index (589 nm D-line: 1.6512) and a high Abbe's number (42.6) can be attained through the polymerization reaction of 2,5-bis(mercaptomethyl)-1,4-dithiane with divinyl sulfone or bis(vinyl sulfone)methane.

PRIOR-ART DOCUMENTS

Patent Documents

Patent Document 1: International Publication WO 2007/032217
Patent Document 2: JP-A-2009-209277
Patent Document 3: JP-A-2010-84122

SUMMARY OF THE INVENTION

Problems that the Invention is to Solve

However, the hybrid material described in patent document 1 has a problem that since the values shown above are attained by incorporating inorganic particles to a high degree into the resin serving as a matrix, it is impossible to further heighten the refractive index and Abbe's number. Namely, it is difficult to obtain a hybrid material which shows a refractive index of 1.65 or higher even with small inorganic-particle incorporation amounts, and in which the refractive index can be controlled in a wide range by further incorporating inorganic particles, and which can retain an Abbe's number of 30 or higher. In addition, patent document 1 includes no statement at all concerning any dispersant for dispersing the inorganic particles, and the dispersion of inorganic particles described therein cannot polymerize by itself.

Meanwhile, the resins described in patent document 2 and patent document 3 each have a problem that a long-term thermal reaction is necessary and the productivity is considerably low from an industrial standpoint. According to investigations made by the present inventors, since the monomers constituting these resins have no polymerizable functional group which enables the monomers to polymerize with each other, each monomer by itself cannot polymerize, and there are no portions absorbable onto inorganic particles. Because of this, in cases when these resins are mixed with inorganic particles, not only dispersion stability cannot be attained but also it is impossible to disperse the inorganic particles in such a manner as to result in transparency. In addition, it has been difficult to improve the refractive index.

A subject for the invention is to provide a polymerizable inorganic-particle dispersant which itself has polymerizability, has a high refractive index and a high Abbe's number, and is capable of dispersing inorganic particles so as to result in transparency and which, when composited with inorganic particles, makes it possible to realize inorganic-organic composite particles and an inorganic-organic resin composite material that combine a high refractive index and a high Abbe's number which have not been attained so far.

Another subject for the invention is to provide inorganic-organic composite particles including the polymerizable inorganic-particle dispersant, an inorganic-organic resin composite material, an optical material including the inorganic-organic resin composite material, and a novel compound which itself has a high refractive index and which combines the high refractive index and a high Abbe's number.

Means for Solving the Problems

The present inventors made various investigations in order to overcome those problems and, as a result, have discovered a polymerizable inorganic-particle dispersant having specific properties and thereby completed the present invention. Specifically, the inventors have discovered that by using a polymerizable inorganic-particle dispersant which has a polymerizable functional group A, a portion B that is adsorbed onto inorganic particles, and a specific group Q in the molecule, both a high refractive index and a high Abbe's number which have not been attained with any conventional organic material can be obtained even with a product produced by polymerizing the polymerizable inorganic-particle dispersant alone, and that the refractive index and the Abbe's number have a low temperature dependence. Furthermore, the inventors have discovered that an improvement in refractive index and retention of the Abbe's number are rendered possible by compositing the polymerizable inorganic-particle dispersant with inorganic particles and further with an organic resin. The present invention has been thus completed.

Namely, essential points of the invention are as follows.
1. A polymerizable inorganic-particle dispersant comprising a compound which includes the following functional groups A, B, and Q:
A: a polymerizable functional group;
B: a carboxyl group, an oxo acid group containing phosphorus, or an oxo acid group containing sulfur; and
Q: a sulfur-containing divalent or more aliphatic hydrocarbon group which may contain a hetero atom other than sulfur.
2. The polymerizable inorganic-particle dispersant according to the item 1 above, wherein the compound including the functional groups A, B, and Q is a compound represented by the following formula (I) or (II):

[In formula (I), $A^1$ represents a polymerizable functional group, $B^1$ represents a carboxyl group, an oxo acid group containing phosphorus, or an oxo acid group containing sulfur, and $Q^1$ represents a sulfur-containing aliphatic hydrocarbon group which has a valence of (n1+m1) and may contain a hetero atom other than sulfur; and n1 and m1 each independently represent an integer of 1-10; with the proviso that when n1 and m1 are integers of 2 or larger, the multiple $A^1$ or $B^1$ moieties present in the molecule may be the same or different.],

[In formula (II), $A^2$ represents a polymerizable functional group, $B^2$ represents a phosphorus-containing oxo acid group having a valence of m2, and $Q^2$ represents a sulfur-containing aliphatic hydrocarbon group which has a valence of (n2+1) and may contain a hetero atom other than sulfur;
n2 represents an integer of 1-10; and
m2 represents an integer of 2-10;
with the proviso that the multiple $A^2$ or $Q^2$ moieties present in the molecule may be the same or different.].
3. The polymerizable inorganic-particle dispersant according to the item 2 above, wherein $Q^1$ in formula (I) or $Q^2$ in formula (II) respectively is a group represented by the following formula (III) or a group represented by the following formula (IV):

[Chem. 1]

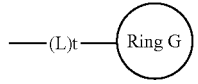 (III)

[In formula (III), ring G represents a saturated, 3- to 8-membered monocycle or bridged ring, or represents a fused ring or spiro ring which is composed of two or three the monocycles or bridged rings bonded together, wherein part of the methylene groups constituting the ring has been replaced with a divalent group comprising a sulfur atom; part of the methylene groups constituting the ring may further include a divalent group comprising an oxygen atom, a nitrogen atom, or a phosphorus atom; L represents a direct bond, a sulfide group, an ether group, or an aliphatic hydrocarbon group which may have a hetero atom, and the multiple L moieties contained in the molecule may be the same or different; and t is (n1+m) (where m and n1 have the same meanings as in the formula (I)) when the formula (III) is $Q^1$, or is (n2+1) (where n2 has the same meaning as in the formula (II)) when the formula (III) is $Q^2$.], $$—[S]_p—[CR_2]_q-[E]_r \quad (IV)$$

[In formula (IV), R represents a hydrogen atom or a hydrocarbon group which may contain a hetero atom; E represents a sulfur atom or an oxygen atom;
p represents an integer of 1-3; q represents an integer of 1-3; and r represents 0 or 1; the multiple R moieties contained In the molecule may be the same or different; and the S, $CR_2$, and E in formula (IV) may have been bonded in any sequence.].
4. The polymerizable inorganic-particle dispersant according to the item 3 above, wherein the hetero atom other than sulfur atom is any of an oxygen atom, a phosphorus atom, and a nitrogen atom.
5. The polymerizable inorganic-particle dispersant according to the item 2 or 3 above, wherein the sulfur-containing aliphatic hydrocarbon group comprises a sulfur-containing cycloaliphatic hydrocarbon group.
6. The polymerizable inorganic-particle dispersant according to the item 5 above, wherein the sulfur-containing cycloaliphatic hydrocarbon group comprises at least one of a dithiane ring, a dithiolane ring, a trithiolane ring, a thiaspiro ring, a dithiaspiro ring, a trithiaspiro ring, a tetrathiaspiro ring, a dithietane ring, a thiirane ring, and a thiolane ring.
7. The polymerizable inorganic-particle dispersant according to the item 5 or 6 above, wherein the sulfur-containing cycloaliphatic hydrocarbon group contains a sulfur-containing chain aliphatic hydrocarbon group as a substituent.
8. The polymerizable inorganic-particle dispersant according to any one of the items 1 to 7 above, wherein the polymerizable functional group A is any of a (meth)acrylic group, an oxirane group, a thiirane group, and an isocyanate group.

9. The polymerizable inorganic-particle dispersant according to any one of the items 1 to 8 above, which has a refractive index of 1.62 or higher.

10. The polymerizable inorganic-particle dispersant according to any one of the items 1 to 8 above, which has an Abbe's number of 40 or higher.

11. Inorganic-organic composite particles which comprise the polymerizable inorganic-particle dispersant according to any one of the items 1 to 10 above and inorganic particles.

12. The inorganic-organic composite particles according to the item 11 above, wherein the inorganic particles are inorganic particles having a refractive index of 2.0 or higher.

13. The inorganic-organic composite particles according to the item 11 or 12 above, wherein the inorganic particles are inorganic particles having a diameter of 1-10 nm.

14. The inorganic-organic composite particles according to any one of the items 11 to 13 above, wherein the content of the inorganic particles is 20-90% by mass based on the polymerizable inorganic-particle dispersant.

15. A dispersion comprising the inorganic-organic composite particles according to any one of the items 11 to 14 above and a dispersion medium.

16. The dispersion according to the item 15 above, which further comprises a polymerizable monomer.

17. An inorganic-organic resin composite material obtained by curing the inorganic-organic composite particles according to any one of the items 11 to 14 above.

18. An optical material comprising the inorganic-organic resin composite material according to the item 17 above.

19. The optical material according to the item 18 above, which is an optical circuit.

20. The optical material according to the item 18 above, which is an optical waveguide.

21. The optical material according to the item 18 above, which is a lens.

22. A compound which comprises the following functional groups A, B, and Q:
   A: a polymerizable functional group;
   B: a carboxyl group, an oxo acid group containing phosphorus, or an oxo acid group containing sulfur; and
   Q: a sulfur-containing divalent or more cycloaliphatic hydrocarbon group which may contain a hetero atom other than sulfur.

Since the polymerizable inorganic-particle dispersant of the invention itself is polymerizable and has a high refractive index and a high Abbe's number, the dispersant is suitable for use as an optical material. Furthermore, the polymerizable inorganic-particle dispersant of the invention can evenly disperse inorganic particles, such as metal oxide nanoparticles having a particle diameter of 1-10 nm, to thereby form inorganic-organic composite particles. The dispersant hence makes it possible to attain an increase in refractive index and an increase in Abbe's number while maintaining transparency. Consequently, the inorganic-organic resin composite material produced using such inorganic-organic composite particles can be effectively applied to optical applications where a high refractive index and a high Abbe's number are required, such as the displays of portable digital assistants or the like, optical lenses, microlenses, switches, lightguide sheets, lightguide plates, or optical waveguide sheets.

MODES FOR CARRYING OUT THE INVENTION

Embodiments of the invention are explained below in detail. The embodiments described below are given for a better understanding of the spirit of the invention, and are not construed as limiting the invention unless otherwise indicated.

1. Polymerizable Inorganic-Particle Dispersant

The polymerizable inorganic-particle dispersant of the invention is a compound which includes the following functional groups A, B, and Q. It is especially preferred that this compound should be a monomer which has transparency throughout the range from the ultraviolet region to the near infrared region.

A: A polymerizable functional group

B: A carboxyl group, an oxo acid group containing phosphorus, or an oxo acid group containing sulfur Q: A sulfur-containing divalent or more aliphatic hydrocarbon group which may contain a hetero atom other than sulfur (1) A: Polymerizable Functional Group A is a polymerizable functional group, which is a functional group that is capable of undergoing homopolymerization (polymerization between polymerizable functional groups A) in the presence of an initiator with the aid of radiation, e.g., ultraviolet rays (UV) or electron beams, or heat, etc. It is preferred that the polymerizable functional group A should be a monovalent polymerizable functional group. Examples of the polymerizable functional group A include a (meth)acrylic group, an oxirane group, a thiirane group, and an isocyanate group. Preferred of these is a (meth)acrylic group, an oxirane group, or a thiirane group, from the standpoint of the ease of synthesis of the polymerizable inorganic-particle dispersant. Furthermore, from the standpoint of productivity or of rendering microfabrication possible, it is preferred that the polymerizable functional group A should be a functional group polymerizable with UV or electron beams, and a (meth)acrylic group is especially preferred.

In this description, the term "(meth)acrylic" means one or both of "acrylic" and "methacrylic"; the same applies to the term "(meth)acrylate" which will appear later.

Due to the inclusion of the polymerizable functional group A in the polymerizable inorganic-particle dispersant, not only the polymerizable inorganic-particle dispersant can be polymerized alone in the presence of an initiator, but also the dispersant, when polymerized as part of a composition obtained by incorporating the dispersant into a photocurable resin, can bring about the effect of, for example, preventing the inorganic particles from separating out, preventing the inorganic particles from being poorly dispersed, or preventing a decrease in mechanical strength.

(2) B: Carboxyl Group, Oxo Acid Group Containing Phosphorus, or Oxo Acid Group Containing Sulfur B is a carboxyl group, an oxo acid group containing phosphorus, or an oxo acid group containing sulfur. From the standpoint of the ease of synthesis of the polymerizable inorganic-particle dispersant, a carboxyl group is preferred. From the standpoint of inhibiting the polymerizable inorganic-particle dispersant from having a color, an oxo acid group containing phosphorus is preferred. B functions as a portion which undergoes chemical bonding or interaction with inorganic particles, such as adsorption, coordination, hydrogen bonding, or covalent bonding, so as to stably disperse the inorganic particles. Preferred are a carboxy group and at least one monovalent, divalent, or more group selected from the structures shown below. The at least one group has a valence of usually 10 or less, preferably 5 or less, more preferably 4 or less, even more preferably 3 or less.

Examples of the oxo acid group containing phosphorus include the following groups.

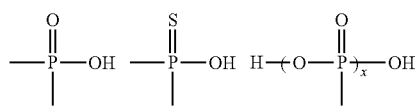
[Chem. 2]

In the formulae, x is an integer of 2 or larger and is usually 10 or smaller, preferably 5 or smaller, more preferably 4 or smaller, even more preferably 3 or smaller.

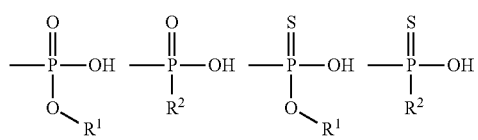
[Chem. 3]

In the formulae, $R^1$, although not particularly limited, is preferably a hydrogen atom or a hydrocarbon group which may have a hetero atom.

The number of carbon atoms of the hydrocarbon group which may have a hetero atom is usually 6 or less, preferably 4 or less, more preferably 3 or less, and is usually 1 or larger. Preferred of such hydrocarbon groups which may have a hetero atom, are sulfur-containing chain aliphatic hydrocarbon groups or sulfur-containing cycloaliphatic hydrocarbon groups, from the standpoints of refractive index and Abbe's number. These sulfur-containing chain aliphatic hydrocarbon groups and sulfur-containing cycloaliphatic hydrocarbon groups may contain hetero atoms other than sulfur, such as oxygen or nitrogen atoms. Meanwhile, from the standpoint of synthesis simplicity, aliphatic hydrocarbon groups are preferred. Of these, a hydrogen atom and aliphatic hydrocarbon groups are preferred, and a hydrogen atom is especially preferred. Incidentally, the hetero atoms are not particularly limited in this description. However, a sulfur atom, oxygen atom, nitrogen atom, and phosphorus atom are preferred.

In the formulae shown above, $R^2$, although not particularly limited, is preferably a hydrogen atom or a hydrocarbon group which may have a hetero atom. The number of carbon atoms of the hydrocarbon group which may have a hetero atom is usually 6 or less, preferably 4 or less, more preferably 3 or less, and is usually 1 or larger. Preferred of such hydrocarbon groups which may have a hetero atom are sulfur-containing chain aliphatic hydrocarbon groups or sulfur-containing cycloaliphatic hydrocarbon groups, from the standpoints of refractive index and Abbe's number. These sulfur-containing chain aliphatic hydrocarbon groups and sulfur-containing cycloaliphatic hydrocarbon groups may contain hetero atoms other than sulfur, such as oxygen or nitrogen atoms. Meanwhile, from the standpoint of synthesis simplicity, aliphatic hydrocarbon groups are preferred. Of these, a hydrogen atom and aliphatic hydrocarbon groups are preferred, and a hydrogen atom is especially preferred.

Examples of the oxo acid group containing sulfur include the following group.

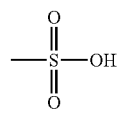
[Chem. 4]

Preferred examples of B include a carboxyl group or groups having the following structures, from the standpoints of inhibiting inorganic particles from aggregating and of attaining the excellent function of stably dispersing the inorganic particles. In the following structures, $R^1$ and $R^2$ are the same as defined above.

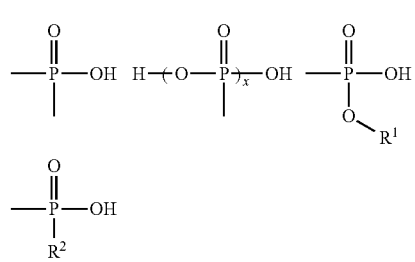
[Chem. 5]

From the standpoint of the ease of synthesis of the polymerizable inorganic-particle dispersant, it is preferred that B should be a carboxyl group. Meanwhile, from the standpoint of inhibiting the polymerizable inorganic-particle dispersant from having a color, the groups having the following structures are preferred.

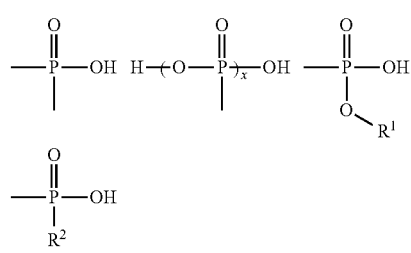
[Chem. 6]

B may be monovalent or may be divalent or more. It is preferred that B which is monovalent should be the $B^1$ contained in formula (I) that will be described later, and examples thereof include the following structures.

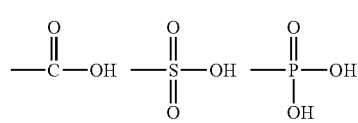
[Chem. 7]

It is preferred that B which is divalent or more should be the $B^2$ contained in formula (II) which will be described later, and examples thereof include the following structures.

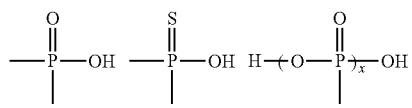

[Chem. 8]

In the formulae, x is an integer of 2 or larger and is usually 10 or smaller, preferably 5 or smaller, more preferably 4 or smaller, even more preferably 3 or smaller.

(3) Q: Sulfur-Containing Divalent or More Aliphatic Hydrocarbon Group which May Contain Hetero Atom Other than Sulfur Q is a sulfur-containing divalent or more aliphatic hydrocarbon group which may contain a hetero atom other than sulfur, and is a group for introducing sulfur atoms and aliphatic hydrocarbon groups into the polymerizable inorganic-particle dispersant of the invention. Because the polymerizable inorganic-particle dispersant of the invention and the inorganic-organic resin composite material of the invention, which is obtained by curing the dispersant, contain sulfur atoms and aliphatic hydrocarbon groups, the dispersant and the composite material not only can combine a high refractive index and a high Abbe's number but also can have a reduced temperature dependence of these properties.

From the standpoint of easily improving optical properties, a sulfur-containing cycloaliphatic hydrocarbon group is preferred. From the standpoint of the stability of the polymerizable inorganic-particle dispersant, it is preferred that the sulfur-containing aliphatic hydrocarbon group should be a sulfur-containing saturated aliphatic hydrocarbon group. Incidentally, the polymerizable inorganic-particle dispersant wherein Q is a sulfur-containing divalent or more cycloaliphatic hydrocarbon group which may contain a hetero atom other than sulfur is a novel compound.

The valence of Q is usually 2 or more and is usually 20 or less, preferably 10 or less, more preferably 5 or less, even more preferably 4 or less, especially preferably 3 or less. Small values of the valence are preferred from the standpoint of ease of production.

The molecular weight of Q is usually 160 or higher, preferably 170 or higher, more preferably 180 or higher, and is usually 2,000 or less, preferably 1,500 or less, more preferably 1,300 or less, even more preferably 1,000 or less, most preferably 800 or less. Molecular weights of the sulfur-containing aliphatic hydrocarbon group not lower than the lower limit are preferred from the standpoint that this compound has low volatility, while molecular weights thereof not higher than the upper limit are preferred from the standpoint that this compound has excellent solubility (compatibility).

The proportion of the sulfur atoms contained in Q is usually 20% by mass or higher, preferably 30% by mass or higher, more preferably 35% by mass or higher, in terms of sulfur atom content. The proportion thereof is usually 90% by mass or less, preferably 85% by mass or less, more preferably 80% by mass or less. Proportions of the sulfur atoms contained in the sulfur-containing aliphatic hydrocarbon group which are not less than the lower limit are preferred from the standpoint that an improvement in refractive index is attained. Proportions thereof not higher than the upper limit are preferred from the standpoint that this compound has high stability.

Although Q is a sulfur-containing aliphatic hydrocarbon group which may contain a hetero atom other than sulfur atom, the term "sulfur-containing aliphatic hydrocarbon group" in the invention means an aliphatic hydrocarbon group in which at least one of the carbon atoms constituting the group has been replaced with a sulfur atom. Preferred of such groups is an aliphatic hydrocarbon group in which at least one of the methylene groups constituting the group has been replaced with a divalent group including a sulfur atom.

The expression "may contain a hetero atom other than sulfur atom" in the invention means that part of the carbon atoms constituting the sulfur-containing aliphatic hydrocarbon group may have been further replaced with one or more hetero atoms other than sulfur atom. Preferably, that expression means that part of the methylene groups constituting the sulfur-containing aliphatic hydrocarbon group may have been replaced with one or more divalent groups including a hetero atom other than sulfur atom.

The hetero atom other than sulfur atom is not particularly limited. However, the hetero atom preferably is one or more of an oxygen atom, a phosphorus atom, and a nitrogen atom, and more preferably is an oxygen atom and/or a nitrogen atom.

Examples of the structure formed by replacing part of the carbon atoms constituting an aliphatic hydrocarbon group with one or more sulfur atoms and optionally with other hetero atom(s) include a structure formed by replacing any methylene group(s) of an aliphatic hydrocarbon group with one or more divalent groups including a sulfur atom.

Examples of the divalent group including a sulfur atom include: a sulfur-containing group such as a sulfide group, disulfide group, or trisulfide group; a sulfur- and oxygen-containing group such as a sulfoxide group, sulfone group, thioester group, thionoester group, or thiocarbonyl group; a sulfur- and phosphorus-containing group such as a thiophosphono group or a dithiophosphono group; and a sulfur- and nitrogen-containing group such as a thioamide group or a thiourea group. Examples of that structure further include these structures which have undergone further replacement with a divalent group containing one or more hetero atoms, such as an oxygen-containing group, e.g., a carbonyl group or an ester group, the oxygen- and phosphorus-containing group shown below,

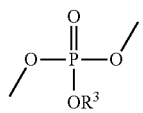

[Chem. 9]

or either of the nitrogen-containing groups shown below.

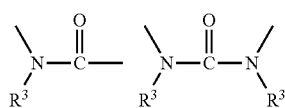

[Chem. 10]

In the formulae shown above, $R^3$ is not particularly limited, and examples thereof include a hydrogen atom and a hydrocarbon group which may have a hetero atom. The number of carbon atoms of the hydrocarbon group which may have a hetero atom is usually 6 or less, preferably 4 or less, more preferably 3 or less, and is usually 1 or larger.

Preferred of such hydrocarbon groups which may have a hetero atom are sulfur-containing chain aliphatic hydrocarbon groups or sulfur-containing cycloaliphatic hydrocarbon groups, from the standpoints of refractive index and Abbe's number. These sulfur-containing chain aliphatic hydrocarbon groups and sulfur-containing cycloaliphatic hydrocarbon groups may contain hetero atoms other than sulfur, such as oxygen or nitrogen atoms. Meanwhile, from the standpoint of synthesis simplicity, aliphatic hydrocarbon groups are preferred. Of these, a hydrogen atom and aliphatic hydrocarbon groups are preferred, and a hydrogen atom is especially preferred.

The sulfur-containing aliphatic hydrocarbon group represented by Q preferably is a group formed by replacing part of an aliphatic hydrocarbon group in which the number of carbon atoms is usually 3 or larger, more preferably 4 or larger, and is usually 20 or less, preferably 15 or less, more preferably 12 or less, with one or more sulfur atoms and optionally with one or more hetero atoms other than sulfur atom. It is preferred that the group represented by Q should be a group formed by replacing part of the methylene groups constituting the aliphatic hydrocarbon group with one or more divalent groups including a sulfur atom and optionally with one or more divalent groups including a hetero atom other than sulfur atom.

The aliphatic hydrocarbon group as the base may have either a chain structure or a cyclic structure or have a cyclic structure having a chain structure as a substituent.

In the case of a chain structure, this structure preferably is a linear or branched aliphatic hydrocarbon group which satisfies the range of the number of carbon atoms. In the case of a cyclic structure having a chain structure as part thereof, it is preferred that the number of carbon atoms including the carbon atoms constituting the chain structure contained therein should be within that range.

Specifically, it is preferred that Q should be either the $Q^1$ contained in formula (I) which will be described later or the $Q^2$ contained in formula (II) which will be described later.

(4) Polymerizable Inorganic-Particle Dispersant

It is especially preferred that the polymerizable inorganic-particle dispersant of the invention should be a compound which imparts dispersion stability to inorganic particles, is capable of maintaining the high refractive index inherent in the inorganic particles, and has a high Abbe's number. Consequently, it is preferred that the polymerizable inorganic-particle dispersant of the invention should contain neither a functional group which brings about a high refractive index but reduces the Abbe's number, such as a benzene ring, nor a functional group which brings about a high Abbe's number but reduces the refractive index, as a component other than B, which is an absorbable portion that serves to stably disperse inorganic particles, and A, which is a functional group that is capable of undergoing homopolymerization in the presence of an initiator.

The molecular weight of the polymerizable inorganic-particle dispersant of the invention is not particularly limited. However, the molecular weight thereof is usually 100 or higher, preferably 150 or higher, more preferably 200 or higher, and is usually 2,000 or less, preferably 1,000 or less, more preferably 800 or less. Molecular weights of the dispersant not lower than the lower limit are preferred from the standpoint that this dispersant has low volatility, while molecular weights thereof not higher than the upper limit are preferred from the standpoint that this dispersant shows excellent solubility (compatibility) when used together with other monomers to produce a composite material.

The proportion of the sulfur atoms contained in the polymerizable inorganic-particle dispersant of the invention is usually 10% by mass or higher, preferably 15% by mass or higher, more preferably 20% by mass or higher, in terms of sulfur atom content. The proportion thereof is usually 70% by mass or less, preferably 60% by mass or less, more preferably 50% by mass or less. In cases when the proportion of the sulfur atoms contained in the dispersant is not less than the lower limit, improvements in optical properties such as refractive index and Abbe's number are attained; such proportions are hence preferred. Proportions thereof not higher than the upper limit are preferred from the standpoints that the starting materials are easily available and that the compound has enhanced stability.

The ratio of A and B in the polymerizable inorganic-particle dispersant, in terms of the ratio of the number of groups B to the number of groups A, is usually 0.1 or larger, preferably 0.5 or larger, more preferably 1 or larger, and is usually 10 or less, preferably 5 or less, more preferably 3 or less, even more preferably 2 or less.

In cases when the ratio of B to A is higher than the lower limit, the inorganic-particle-dispersing function of the polymerizable inorganic-particle dispersant of the invention improves. From this standpoint, such ratios are preferred. Furthermore, such ratios are preferred also from the standpoints that this polymerizable inorganic-particle dispersant of the invention has improved storage stability and that this dispersant tends to be capable of being inhibited from gelling during storage, polymerization, etc. Meanwhile, in cases when the proportion of B to A is less than the upper limit, the inorganic-organic resin composite material to be obtained from the polymerizable inorganic-particle dispersant of the invention can have improved strength.

The content (% by mass) of A in the polymerizable inorganic-particle dispersant of the invention is usually 5% by mass or higher, preferably 10% by mass or higher, more preferably 15% by mass or higher. The content thereof is usually 40% by mass or less, preferably 30% by mass or less, more preferably 20% by mass or less. In cases when the content of A is not less than the lower limit, the inorganic-organic resin composite material to be obtained from the polymerizable inorganic-particle dispersant of the invention can have improved strength. In cases when the content of A is not higher than the upper limit, the polymerizable inorganic-particle dispersant of the invention has improved storage stability and can be inhibited from gelling during polymerization, etc.

The content (% by mass) of B in the polymerizable inorganic-particle dispersant of the invention is usually 10% by mass or higher, preferably 15% by mass or higher, more preferably 20% by mass or higher. The content thereof is usually 50% by mass or less, preferably 40% by mass or less. Contents of B not less than the lower limit are preferred from the standpoint that the inorganic-particle-dispersing function of this polymerizable inorganic-particle dispersant of the invention is improved. In cases when the content of B is not higher than the upper limit, nanoparticle aggregation can be inhibited when this polymerizable inorganic-particle dispersant of the invention is mixed with inorganic particles.

The content (% by mass) of Q in the polymerizable inorganic-particle dispersant of the invention is usually 20% by mass or higher, preferably 30% by mass or higher, more preferably 40% by mass or higher. The content thereof is usually 90% by mass or less, preferably 80% by mass or less, more preferably 70% by mass or less, even more preferably 60% by mass or less. In cases when the content of Q is not less than the lower limit, it is easy to improve the optical properties, in particular, refractive index and Abbe's number, of the polymerizable inorganic-particle dispersant. In cases when the content of Q is not higher than the upper limit, this polymerizable inorganic-particle dispersant is more compatible when mixed with polymerizable monomers to produce an inorganic-organic resin composite material.

Although the polymerizable inorganic-particle dispersant of the invention includes A, B, and Q, the sequence of bonding of the A, B, and Q is not particularly limited. In the case where B is monovalent, there is no direct bond between A and B, and A and B each are bonded to Q to form the polymerizable inorganic-particle dispersant. Examples of the bonding of A, B, and Q in the case where B is monovalent include the following structures.

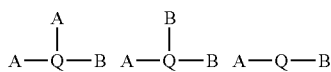
[Chem. 11]

Preferred examples, among these, include compounds represented by formula (I) which will be described later. In the case where B is divalent or more, the number of groups Q and that of groups B are not limited and these groups can be bonded at any positions in any proportion. In this case, monovalent A may be bonded to either Q or B. Examples of the bonding of A, B, and Q in the case where B is divalent include the following structures.

<div style="text-align:center">A-Q-B-AA-Q-B-Q-A [Chem. 12]</div>

Preferred examples, among these, include compounds represented by formula (II) which will be described later.

It is also possible to use monovalent B and divalent B in combination. The monovalent B is usually bonded to Q and located at an end of the polymerizable inorganic-particle dispersant of the invention, while the divalent B is bonded to A or Q. In the case of using monovalent B and divalent B in combination, examples of the bonding of A, B, and Q include the following structure.

<div style="text-align:center">A-Q-B-Q-B [Chem. 13]</div>

2. Preferred Examples of Structure of the Polymerizable Inorganic-Particle Dispersant Preferred as the compound including the functional groups A, B, and Q described above is a compound represented by the following formula (I) or following formula (II) (hereinafter sometimes referred to as "compound (I)" or "compound (II)", respectively).

(1) Compound Represented by Formula (I)

$$(A^1)_{n1}\text{-}Q^1\text{-}(B^1)_{m1} \qquad (I)$$

In formula (I), $A^1$ represents a polymerizable functional group, $B^1$ represents a carboxyl group, an oxo acid group containing phosphorus, or an oxo acid group containing sulfur, and $Q^1$ represents a sulfur-containing aliphatic hydrocarbon group which has a valence of (n1+m1) and may contain a hetero atom other than sulfur. Symbols n1 and m1 each independently represent an integer of 1-10, with the proviso that when n1 and m1 are integers of 2 or larger, the multiple $A^1$ or $B^1$ moieties present in the molecule may be the same or different.

The functional groups $A^1$, $B^1$, and $Q^1$ contained in compound (I) are explained below.

(1-1) Functional Group $A^1$ $A^1$ is a monovalent polymerizable functional group, and is usually not particularly limited so long as $A^1$ is a functional group which is capable of undergoing homopolymerization in the presence of an initiator with the aid of actinic energy rays, such as ultraviolet rays (UV) or electron beams, or heat, etc. Examples thereof include a (meth)acrylic group, an oxirane group, a thiirane group, and an isocyanate group. Preferred of these is a (meth)acrylic group, an oxirane group, or a thiirane group, from the standpoint of the ease of synthesis of the polymerizable inorganic-particle dispersant. Furthermore, from the standpoint of productivity or of rendering microfabrication possible, it is preferred that the polymerizable functional group should be a functional group polymerizable with UV or electron beams, and a (meth)acrylic group is especially preferred.

Due to the inclusion of the polymerizable functional group $A^1$ in the polymerizable inorganic-particle dispersant, not only the polymerizable inorganic-particle dispersant can be polymerized alone in the presence of an initiator, but also the dispersant, when polymerized as part of a composition obtained by incorporating the dispersant into a photocurable resin, can bring about the effect of, for example, preventing the inorganic particles from separating out, preventing the inorganic particles from being poorly dispersed, or preventing a decrease in mechanical strength.

(1-2) Functional Group $B^1$ $B^1$ represents a carboxyl group, an oxo acid group containing phosphorus, or an oxo acid group containing sulfur. From the standpoint of the ease of synthesis of the polymerizable inorganic-particle dispersant, a carboxyl group is preferred. From the standpoint of inhibiting the polymerizable inorganic-particle dispersant from having a color, an oxo acid group containing phosphorus is preferred.

The oxo acid group containing phosphorus is a monovalent oxo acid group containing phosphorus, and groups having the following structures are preferred.

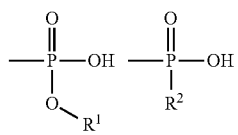
[Chem. 14]

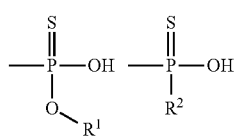
[Chem. 15]

In the formulae, $R^1$, although not particularly limited, is preferably a hydrogen atom or a hydrocarbon group which may have a hetero atom. The number of carbon atoms of the hydrocarbon group which may have a hetero atom is usually 6 or less, preferably 4 or less, more preferably 3 or less, and is usually 1 or larger.

Preferred of such hydrocarbon groups which may have a hetero atom are sulfur-containing chain aliphatic hydrocarbon groups or sulfur-containing cycloaliphatic hydrocarbon groups, from the standpoints of refractive index and Abbe's number. These sulfur-containing chain aliphatic hydrocarbon groups and sulfur-containing cycloaliphatic hydrocarbon groups may contain hetero atoms other than sulfur, such as oxygen or nitrogen atoms. Meanwhile, from the standpoint of synthesis simplicity, aliphatic hydrocarbon groups are preferred. Of these, a hydrogen atom and aliphatic hydrocarbon groups are preferred, and a hydrogen atom is especially preferred.

$R^2$ is not particularly limited. However, $R^2$ preferably is a hydrogen atom or a hydrocarbon group which may have a hetero atom. The number of carbon atoms of the hydrocarbon group which may have a hetero atom is usually 6 or less, preferably 4 or less, more preferably 3 or less, and is usually 1 or larger.

Preferred of such hydrocarbon groups which may have a hetero atom are sulfur-containing chain aliphatic hydrocarbon groups or sulfur-containing cycloaliphatic hydrocarbon groups, from the standpoints of refractive index and Abbe's number. These sulfur-containing chain aliphatic hydrocarbon groups and sulfur-containing cycloaliphatic hydrocarbon groups may contain hetero atoms other than sulfur, such as oxygen or nitrogen atoms. Meanwhile, from the standpoint of synthesis simplicity, aliphatic hydrocarbon groups are preferred. Of these, a hydrogen atom and aliphatic hydrocarbon groups are preferred, and a hydrogen atom is especially preferred.

Specifically, for example, a phosphonoxy group [—OPO$(OH)_2$] and a phosphono group [—PO$(OH)_2$] are preferred, and a phosphono group is most preferred.

Examples of the oxo acid group containing sulfur include a sulfo group [—$SO_2$(OH)], a sulfino group [—SO(OH)], and a sulfeno group [—SOH]. Preferred are a sulfo group and a sulfino group. More preferred is a sulfo group.

$B^1$ preferably is a carboxyl group or an oxo acid group containing phosphorus, and more preferably is an oxo acid group containing phosphorus, from the standpoints of inhibiting inorganic particles from aggregating and of attaining the excellent function of stably dispersing the inorganic particles.

(1-3) Functional Group $Q^1$ $Q^1$ represents a sulfur-containing aliphatic hydrocarbon group which has a valence of (n1+m1) and may contain a hetero atom other than sulfur. The inclusion of a sulfur-containing aliphatic hydrocarbon group in $Q^1$ is preferred from the standpoint of heightening the Abbe's number of the polymerizable inorganic-particle dispersant. From the standpoint of the stability of the polymerizable inorganic-particle dispersant, it is preferred that the sulfur-containing aliphatic hydrocarbon group should be a sulfur-containing saturated aliphatic hydrocarbon group.

The molecular weight of $Q^1$ is usually 160 or higher, preferably 170 or higher, more preferably 180 or higher, and is usually 2,000 or less, preferably 1,500 or less, more preferably 1,300 or less. Molecular weights of the sulfur-containing aliphatic hydrocarbon group not lower than the lower limit are preferred from the standpoint that this compound has low volatility, while molecular weights thereof not higher than the upper limit are preferred from the standpoint that this compound has excellent solubility (compatibility).

The proportion of the sulfur atoms contained in $Q^1$ is usually 20% by mass or higher, preferably 30% by mass or higher, more preferably 35% by mass or higher, in terms of sulfur atom content. The proportion thereof is usually 90% by mass or less, preferably 85% by mass or less, more preferably 80% by mass or less. Proportions of the sulfur atoms contained in the sulfur-containing aliphatic hydrocarbon group which are not less than the lower limit are preferred from the standpoint that an improvement in refractive index is attained. Proportions thereof not higher than the upper limit are preferred from the standpoint that this compound has high stability.

Although $Q^1$ is a sulfur-containing aliphatic hydrocarbon group which may contain a hetero atom other than sulfur atom, the term "sulfur-containing aliphatic hydrocarbon group" in the invention means an aliphatic hydrocarbon group in which at least one of the carbon atoms constituting the group has been replaced with a sulfur atom. Preferred of such groups is an aliphatic hydrocarbon group in which at least one of the methylene groups constituting the group has been replaced with a divalent group including a sulfur atom.

The expression "may contain a hetero atom other than sulfur atom" in the invention means that part of the carbon atoms constituting the sulfur-containing aliphatic hydrocarbon group may have been further replaced with one or more hetero atoms other than sulfur atom. Preferably, that expression means that part of the methylene groups constituting the sulfur-containing aliphatic hydrocarbon group may have been replaced with one or more divalent groups including a hetero atom other than sulfur atom.

The hetero atom other than sulfur atom is not particularly limited. However, the hetero atom preferably is one or more of an oxygen atom, a phosphorus atom, and a nitrogen atom, and more preferably is an oxygen atom and/or a nitrogen atom.

Examples of the structure formed by replacing part of the carbon atoms constituting an aliphatic hydrocarbon group with one or more sulfur atoms and optionally with other hetero atom(s) include a structure formed by replacing any methylene group(s) of an aliphatic hydrocarbon group with one or more divalent groups including a sulfur atom. Examples of the divalent group including a sulfur atom include: a sulfur-containing group such as a sulfide group, disulfide group, or trisulfide group; a sulfur- and oxygen-containing group such as a sulfoxide group, sulfone group, thioester group, thionoester group, or thiocarbonyl group; a sulfur- and phosphorus-containing group such as a thiophosphono group or a dithiophosphono group; and a sulfur- and nitrogen-containing group such as a thioamide group or a thiourea group. Examples of that structure further include these structures which have undergone further replacement with a divalent group containing one or more hetero atoms, such as an oxygen-containing group, e.g., a carbonyl group or an ester group, the oxygen- and phosphorus-containing group shown below,

[Chem. 16]

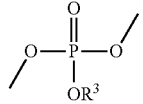

or either of the nitrogen-containing groups shown below.

[Chem. 17]

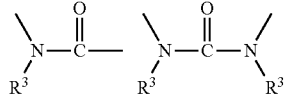

In the formulae shown above, $R^3$ is not particularly limited, and examples thereof include a hydrogen atom and a hydrocarbon group which may have a hetero atom. The number of carbon atoms of the hydrocarbon group which may have a hetero atom is usually 6 or less, preferably 4 or less, more preferably 3 or less, and is usually 1 or larger.

Preferred of such hydrocarbon groups which may have a hetero atom are sulfur-containing chain aliphatic hydrocarbon groups or sulfur-containing cycloaliphatic hydrocarbon groups, from the standpoints of refractive index and Abbe's number. These sulfur-containing chain aliphatic hydrocarbon groups and sulfur-containing cycloaliphatic hydrocarbon groups may contain hetero atoms other than sulfur, such as oxygen or nitrogen atoms. Meanwhile, from the standpoint of synthesis simplicity, aliphatic hydrocarbon groups are preferred. Of these, a hydrogen atom and aliphatic hydrocarbon groups are preferred, and a hydrogen atom is especially preferred.

The sulfur-containing aliphatic hydrocarbon group represented by $Q^1$ in general formula (I) preferably is a group formed by replacing part of an aliphatic hydrocarbon group in which the number of carbon atoms is usually 3 or larger, more preferably 4 or larger, and is usually 20 or less, preferably 15 or less, more preferably 12 or less, with one or more sulfur atoms and optionally with one or more hetero atoms other than sulfur atom. It is preferred that the group represented by $Q^1$ should be a group formed by replacing part of the methylene groups constituting the aliphatic hydrocarbon group with one or more divalent groups including a sulfur atom and optionally with one or more divalent groups including a hetero atom other than sulfur atom.

The aliphatic hydrocarbon group as the base may have either a chain structure or a cyclic structure or have a cyclic structure having a chain structure as a substituent.

In the case of a chain structure, this structure preferably is a linear or branched aliphatic hydrocarbon group which satisfies the range of the number of carbon atoms. In the case of a cyclic structure having a chain structure as part thereof, it is preferred that the number of carbon atoms including the carbon atoms constituting the chain structure contained therein should be within that range.

Examples of the sulfur-containing aliphatic hydrocarbon group include a sulfur-containing cycloaliphatic hydrocarbon group and a sulfur-containing chain aliphatic hydrocarbon group. Preferred is a sulfur-containing cycloaliphatic hydrocarbon group, from the standpoint that the content of sulfur atoms per unit volume of the molecule can be increased. The sulfur-containing cycloaliphatic hydrocarbon group and the sulfur-containing chain aliphatic hydrocarbon group are explained below in detail.

(1-3-1) Sulfur-Containing Cycloaliphatic Hydrocarbon Group

The sulfur-containing cycloaliphatic hydrocarbon group may have a chain structure as a substituent. In the case where the sulfur-containing cycloaliphatic hydrocarbon group has a chain structure, this hydrocarbon group may be bonded to A and/or B either through the chain structure or not through the chain structure. However, bonding through the chain structure is preferred from the standpoint of ease of production.

Preferred as the chain structure is a sulfur-containing chain aliphatic hydrocarbon group which may have a hetero atom such as oxygen or nitrogen, from the standpoint of attaining both refractive index and Abbe's number.

The molecular weight of the sulfur-containing cycloaliphatic hydrocarbon group, in terms of the molecular weight thereof including that of, if any, substituent, is usually 160 or higher, preferably 170 or higher, more preferably 180 or higher, and is usually 2,000 or less, preferably 1,500 or less, more preferably 1,300 or less. Molecular weights of the sulfur-containing cycloaliphatic hydrocarbon group not lower than the lower limit are preferred from the standpoint that this compound has low volatility, while molecular weights thereof not higher than the upper limit are preferred from the standpoint that this compound has excellent solubility (compatibility).

The sulfur-containing cycloaliphatic hydrocarbon group is a group formed by replacing part of the methylene groups constituting an aliphatic hydrocarbon group in which the number of carbon atoms, including the carbon atoms of, if any, substituent, is usually 3 or larger, more preferably 4 or larger, and is usually 20 or less, preferably 15 or less, more preferably 12 or less, with one or more divalent groups including a sulfur atom and optionally with one or more divalent groups including a hetero atom other than sulfur atom.

The proportion of the sulfur atoms contained in the sulfur-containing cycloaliphatic hydrocarbon group is usually 20% by mass or higher, preferably 30% by mass or higher, more preferably 35% by mass or higher, in terms of sulfur atom content. The proportion thereof is usually 90% by mass or less, preferably 85% by mass or less, more preferably 80% by mass or less. Proportions of the sulfur atoms contained in the sulfur-containing cycloaliphatic hydrocarbon group which are not less than the lower limit are preferred from the standpoint of an increase in refractive index, while proportions thereof not higher than the upper limit are preferred because this compound has high stability.

Preferred of such sulfur-containing cycloaliphatic hydrocarbon groups is a sulfur-containing cycloaliphatic hydrocarbon group represented by the structure of formula (III).

[Chem. 18]

(III)

In formula (III), ring G represents a saturated, 3- to 8-membered monocycle or bridged ring or represents a fused ring or spiro ring which is composed of two or three such monocycles or bridged rings bonded together, wherein part of the methylene groups constituting the ring has been replaced with one or more divalent groups including a sulfur atom. Part of the methylene groups constituting the ring may have been further replaced with one or more divalent groups including a hetero atom such as an oxygen atom, a nitrogen atom, or a phosphorus atom.

L represents a direct bond, a sulfide group, an ether group, or an aliphatic hydrocarbon group which may have a hetero atom, and the multiple L moieties contained in the molecule may be the same or different. Symbol t is (n1+m1) (wherein m1 and n1 have the same meanings as in formula (I)). Incidentally, the inorganic particle dispersant in which $Q^1$ is a sulfur-containing cycloaliphatic hydrocarbon group represented by the structure of formula (III) is a preferred novel compound.

Ring G

Ring G represents a saturated, 3- to 8-membered monocycle or bridged ring or represents a fused ring or spiro ring which is composed of two or three such monocycles or bridged rings bonded together, wherein part of the methylene groups constituting the ring has been replaced with one or more divalent groups including a sulfur atom. Part of the methylene groups constituting the ring may have been further replaced with one or more divalent groups including a hetero atom such as an oxygen atom, a nitrogen atom, or a phosphorus atom.

Examples of the monocycle include thiirane (which is excluded when A is a thiirane group), dithiirane, thietane, 1,2-dithietane, 1,3-dithietane, trithietane, thiolane, 1,2-dithiolane, 1,3-dithiolane, 1,2,3-trithiolane, 1,2,4-trithiolane, tetrathiolane, the sulfur-containing cycloaliphatic hydrocarbons of the structures shown below, 1,2-dithiane, 1,3-dithiane, 1,4-dithiane, 1,2,3-trithiane, 1,2,4-trithiane, 1,3,5-trithiane, 1,2,3,4-tetrathiane, 1,2,4,5-tetrathiane, bis(1,2,3,5,6-pentathiepano)methane, tris(1,2,3,5,6-pentathiepano)methane, thiepane, 1,2-dithiepane, 1,3-dithiepane, 1,4-dithiepane, 1,2,3-trithiepane, 1,2,4-trithiepane, 1,2,5-trithiepane, 1,3,5-trithiepane, 1,2,3,4-tetrathiepane, 1,2,3,5-tetrathiepane, 1,2,4,5-tetrathiepane, 1,2,4,6-tetrathiepane, 1,2,3,4,5-pentathiepane, 1,2,3,4,6-pentathiepane, 1,2,3,5,6-pentathiepane, and hexathiepane.

[Chem. 19]

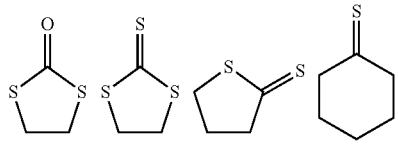

Examples of the bridged ring include the sulfur-containing cycloaliphatic hydrocarbons of the structures shown below.

[Chem. 20]

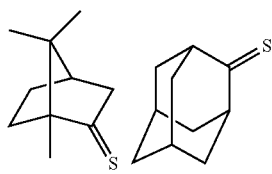

Examples of the fused ring composed of two or three such monocycles or bridged rings bonded together include the sulfur-containing cycloaliphatic hydrocarbons of the structures shown below.

[Chem. 21]

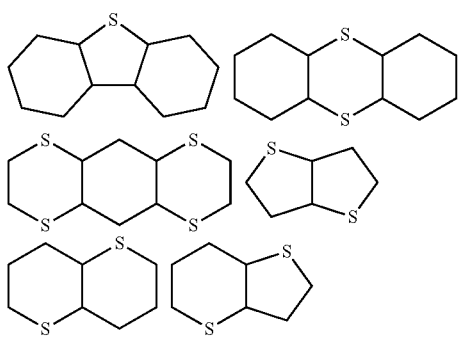

Examples of the Spiro ring composed of two or three such monocycles or bridged rings bonded together include 1,4-dithiaspiro[4.5]decane, 1,5-dithiaspiro[5.5]undecane, 2,4,8,10-tetrathiaspiro[5.5]undecane, and the sulfur-containing cycloaliphatic hydrocarabons of the structures shown below.

[Chem. 22]

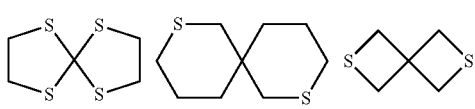

It is preferred that the sulfur-containing cycloaliphatic hydrocarbon should include at least one of a dithiane ring, a dithiolane ring, a trithiolane ring, a thiaspiro ring, a dithiaspiro ring, a trithiaspiro ring, a tetrathiaspiro ring, a dithietane ring, a thiirane ring, and a thiolane ring, from the standpoint that the content of sulfur atoms per unit volume of the molecule can be increased.

Furthermore, the sulfur-containing cycloaliphatic hydrocarbons of the structures shown below are preferred from the standpoint that these hydrocarbons are easy to produce industrially, are stable compounds, and are suitable for easily obtaining optical properties.

[Chem. 23]

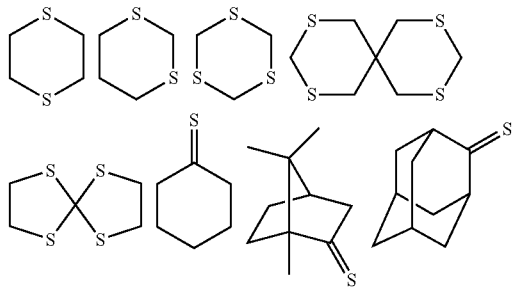

Moreover, the sulfur-containing cycloaliphatic hydrocarbon groups of the structures shown below are preferred from the standpoint that these hydrocarbons enable efficient introduction of sulfur atoms and facilitate control of optical properties.

[Chem. 24]

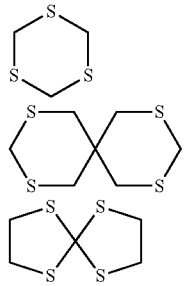

L

L represents a direct bond, a sulfide group, an ether group, or an aliphatic hydrocarbon group which may have a hetero atom, and the multiple L moieties contained in the molecule may be the same or different. The number of carbon atoms of the aliphatic hydrocarbon group which may have a hetero atom is usually 1 or larger and is usually 6 or less, preferably 5 or less, more preferably 4 or less, even more preferably 3 or less.

From the standpoints of ease of production and the stability of the compound, a hydrocarbon group which may have a hetero atom is preferred. Preferred as the hydrocarbon group which may have a hetero atom is an aliphatic hydrocarbon group which may have a hetero atom. More preferred is a sulfur-containing chain aliphatic hydrocarbon group which may have a hetero atom other than sulfur. Even more preferred is the sulfur-containing chain aliphatic hydrocarbon group which will be described later under (1-3-2).

In the case where the cyclic structure of the sulfur-containing cycloaliphatic hydrocarbon group is bonded to A, it is preferred that L should have the structure —C—S—, —C—C—S—, —C—O—, or —C—C—O—. In the case where the cyclic structure of the sulfur-containing cycloaliphatic hydrocarbon group is bonded to B, it is preferred that L should have the structure —C—S—, —C—C—S—, —C—S—C—, —C—, —C—O—, —C—C—O—, or —C—O—C—. In each of these expressions, the left-hand side is the portion bonded to the cyclic structure and the right-hand side is the portion bonded to A or B.

Preferred of those are structures in which the number of carbon atoms is small, from the standpoint of increasing the content of sulfur atoms. Furthermore, structures in which none of the sulfur atoms contained in the cyclic structure forms a thioacetal structure with any sulfur atom contained in the substituents are preferred because this compound is stable.

Preferred examples of $Q^1$ include the following structures.

[Chem. 25]

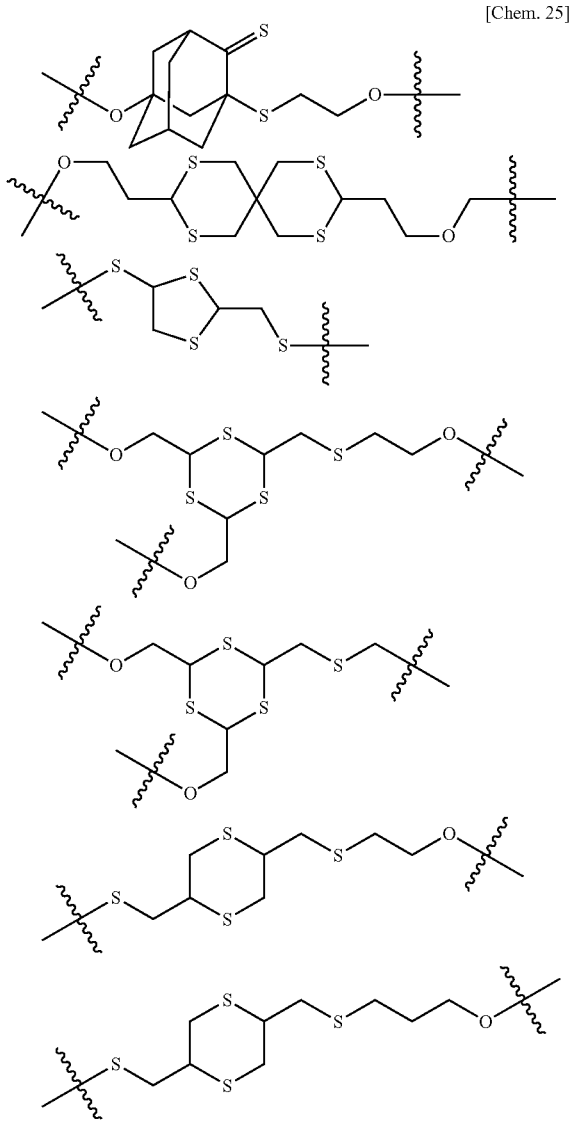

(1-3-2) Sulfur-Containing Chain Aliphatic Hydrocarbon Group

The molecular weight of the sulfur-containing chain aliphatic hydrocarbon group, in terms of the molecular weight thereof including that of, if any, substituent, is usually 60 or higher, preferably 80 or higher, more preferably 90 or higher, and is usually 1,000 or less, preferably 500 or less, more preferably 300 or less. Molecular weights of the sulfur-containing chain aliphatic hydrocarbon group not less than the lower limit are preferred from the standpoint that this compound has low volatility, while molecular weights thereof not higher than the upper limit are preferred from the standpoint that this compound has excellent solubility (compatibility).

It is preferred that the sulfur-containing chain aliphatic hydrocarbon group should be a group formed by replacing part of the methylene groups constituting an aliphatic hydrocarbon group in which the number of carbon atoms, including the carbon atoms of, if any, substituent, is usually 1 or larger, preferably 2 or larger, more preferably 3 or larger, and is usually 20 or less, preferably 15 or less, more preferably 10 or less, with one or more sulfur atoms and optionally with one or more hetero atoms other than sulfur atom.

The proportion of the sulfur atoms contained in the sulfur-containing chain aliphatic hydrocarbon group is usually 20% by mass or higher, preferably 30% by mass or higher, more preferably 35% by mass or higher, in terms of sulfur atom content. The proportion thereof is usually 90% by mass or less, preferably 85% by mass or less, more preferably 80% by mass or less.

Proportions of the sulfur atoms contained in the sulfur-containing chain aliphatic hydrocarbon group which are not lower than the lower limit are preferred from the standpoint of enabling the inorganic particle dispersant to combine a high refractive index and a high Abbe's number. Proportions thereof not higher than the upper limit are preferred from the standpoint that the coloration of the inorganic particle dispersant is only slight. The case where the sulfur-containing aliphatic hydrocarbon group is a sulfur-containing chain aliphatic hydrocarbon group is preferred from the standpoints of solubility and easy impartation of flexibility to the cured object.

Preferred of such sulfur-containing chain aliphatic hydrocarbon groups is a sulfur-containing chain aliphatic hydrocarbon group represented by the structure of formula (IV).

$$—[S]_p—[CR_2]_q-[E]_r- \qquad (IV)$$

In formula (IV), R represents a hydrogen atom or a hydrocarbon group which may contain a hetero atom, and E represents an oxygen atom. Symbol p represents an integer of 1-3, q represents an integer of 1-3, and r represents 0 or 1. The multiple R moieties contained in the molecule may be the same or different. The S, $CR_2$, and E in formula (IV) may have been bonded in any sequence. The number of carbon atoms of the hydrocarbon group which may have a hetero atom is usually 6 or less, preferably 4 or less, more preferably 3 or less, and is usually 1 or larger. Preferred of such hydrocarbon groups which may have a hetero atom are sulfur-containing chain aliphatic hydrocarbon groups or sulfur-containing cycloaliphatic hydrocarbon groups, from the standpoints of refractive index and Abbe's number. These sulfur-containing chain aliphatic hydrocarbon groups and sulfur-containing cycloaliphatic hydrocarbon groups may contain hetero atoms other than sulfur, such as oxygen or nitrogen. Meanwhile, from the standpoint of synthesis simplicity, aliphatic hydrocarbon groups are preferred. Of these, a hydrogen atom and aliphatic hydrocarbon groups are preferred, and a hydrogen atom is especially preferred.

Examples of the sulfur-containing chain aliphatic hydrocarbon groups include groups having the structure —S—C—C—S—C—O— or —S—C—C—O—, an ethylenethio group, an ethylenethioethylene group, a methylenedithio group, a methylenetrithio group, and the groups shown below. However, the sulfur-containing chain aliphatic hydrocarbon groups are not limited to these. In the following structural formulae, each straight-line portion with a wavy line affixed thereto is a portion bonded to A or B.

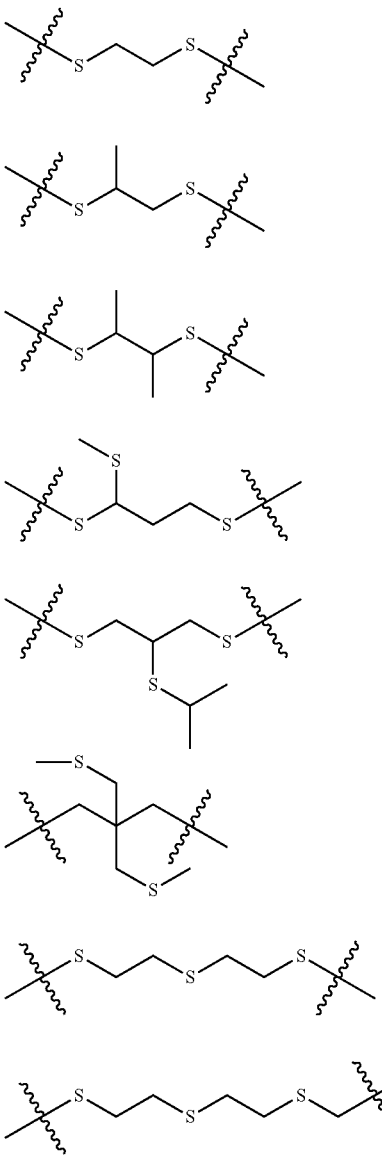

[Chem. 26]

Preferred of these are an ethylenethio group, an ethylenethioethylene group, and the groups shown below.

[Chem. 27]

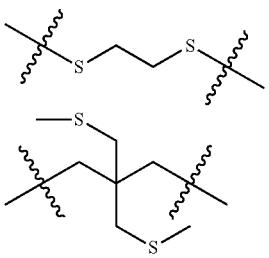

Due to the inclusion of such a hetero-atom-containing hydrocarbon group $Q^1$ in the polymerizable inorganic-particle dispersant of the invention, it becomes possible to stably disperse inorganic particles in a desired dispersion medium so as to result in transparency, and it becomes possible to impart a high Abbe's number while maintaining the high refractive index possessed by the inorganic particles, making it possible to perform refractive-index control and Abbe's-number control in a high-refractive-index range due to the inorganic particles.

<n1, m1>

In formula (I), n1 and m1 each independently represent an integer of 1-10, and are each preferably an integer of 1-6, more preferably an integer of 1-3. Although n1 and m1 need to be 1 or larger, too large numbers are undesirable because the polymerizable inorganic-particle dispersant has a reduced refractive index.

The ratio between n1 and m1, in terms of the ratio of n1 to m1, is usually 0.1 or larger, preferably 0.2 or larger, more preferably 0.3 or larger, even more preferably 0.5 or larger, and is usually 10 or less, preferably 5 or less, more preferably 3 or less, even more preferably 2 or less. The ratio thereof is especially preferably 1.

Preferred examples of the compound represented by formula (I) include the following compounds.

[Chem. 28]

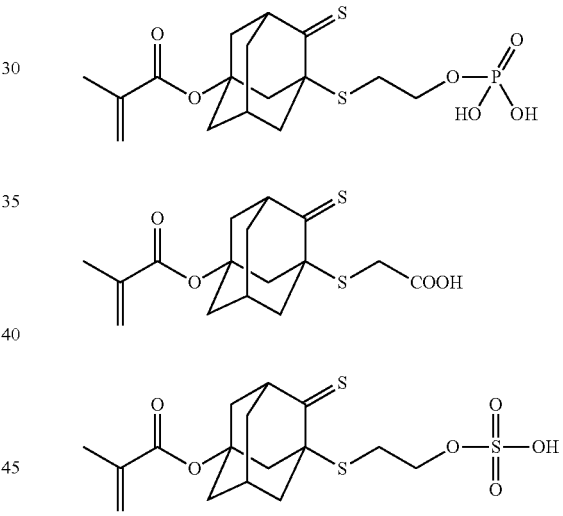

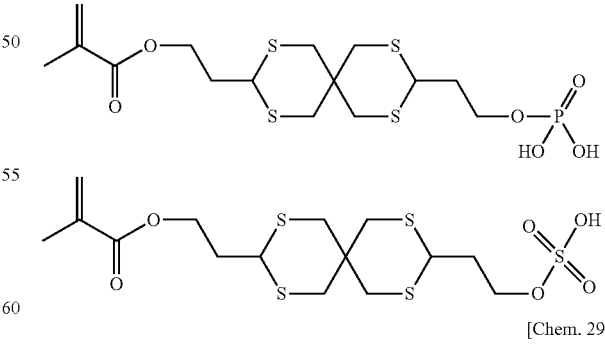

[Chem. 29]

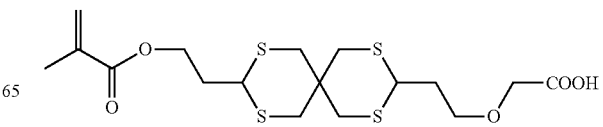

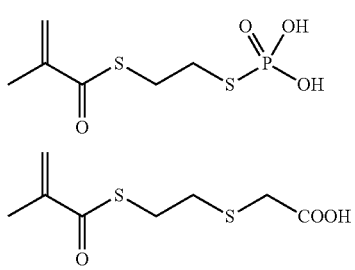
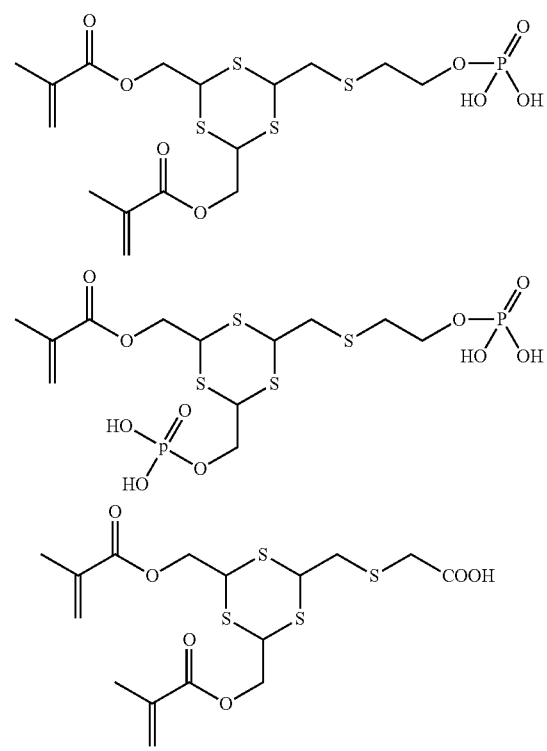

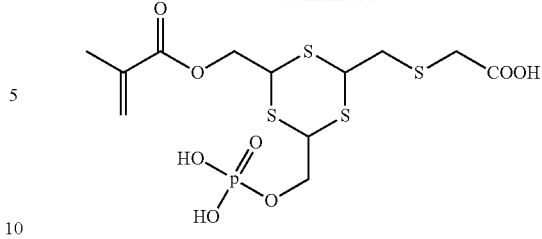

(2) Compound Represented by Formula (II)

$$\{(A^2)_{n2}\text{-}Q^2\}_{m2}\text{-}B^2 \qquad (II)$$

In formula (II), $A^2$ represents a polymerizable functional group, $B^2$ represents a phosphorus-containing oxo acid group having a valence of m2, and $Q^2$ represents a sulfur-containing aliphatic hydrocarbon group which has a valence of (n2+1) and may contain a hetero atom other than sulfur. Symbol n2 represents an integer of 1-10, and m2 represents an integer of 2-5, with the proviso that the multiple $A^2$ or $Q^2$ moieties present in the molecule may be the same or different.

The functional groups $A^2$, $B^2$, and $Q^2$ contained in compound (II) are explained below.

(2-1) Functional Group $A^2$ $A^2$ is a monovalent polymerizable functional group, and is usually not particularly limited so long as $A^2$ is a functional group which is capable of undergoing homopolymerization in the presence of an initiator with the aid of actinic energy rays, such as ultraviolet rays (UV) or electron beams, or heat, etc. Examples thereof include a (meth)acrylic group, an oxirane group, a thiirane group, or an isocyanate group. Preferred of these, from the standpoint of productivity or of rendering microfabrication possible, is a functional group polymerizable with UV or electron beams. A (meth)acrylic group is especially preferred.

Due to the inclusion of the polymerizable functional group $A^2$ in the polymerizable inorganic-particle dispersant, not only the polymerizable inorganic-particle dispersant can be polymerized alone in the presence of an initiator, but also the dispersant, when polymerized as part of a composition obtained by incorporating the dispersant into a photocurable resin, can bring about the effect of, for example, preventing the inorganic particles from separating out, preventing the inorganic particles from being poorly dispersed, or preventing a decrease in mechanical strength.

(2-2) Functional Group $B^2$ $B^2$ represents a phosphorus-containing oxo acid group having a valence of m2, and m2 is an integer of 2-5.

Examples of the phosphorus-containing oxo acid group having a valence of m2 include groups having the following structures.

[Chem. 31]

Formula (P)

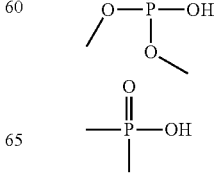

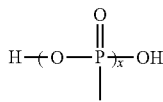

In formula (P), x is an integer of 2-5.

Examples of the structure of formula (P) include the following structures.

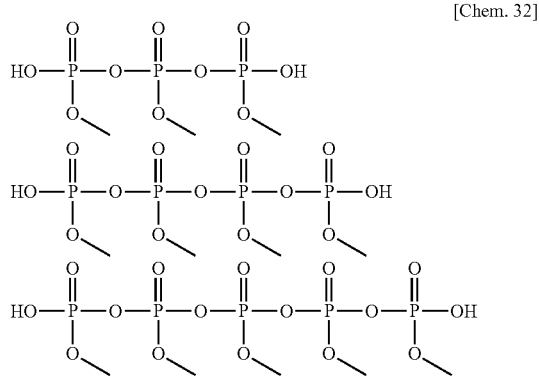
[Chem. 32]

The phosphorus-containing oxo acid group having a valence of m2 may contain one or more sulfur atoms. Examples thereof include the groups having the following structures.

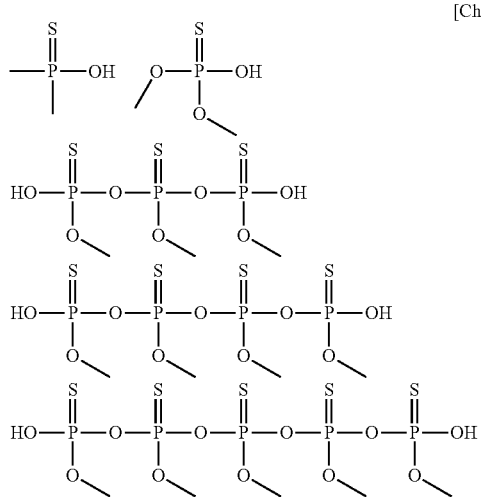
[Chem. 33]

Incidentally, $B^2$ may be bonded to any substituents other than $Q^2$. Examples of such substituents include a hydrogen atom and a hydrocarbon group which may have a hetero atom. The number of carbon atoms of the hydrocarbon group which may have a hetero atom is usually 6 or less, preferably 4 or less, more preferably 3 or less, and is usually 1 or larger. Preferred of such hydrocarbon groups which may have a hetero atom are sulfur-containing chain aliphatic hydrocarbon groups or sulfur-containing cycloaliphatic hydrocarbon groups, from the standpoints of refractive index and Abbe's number. These sulfur-containing chain aliphatic hydrocarbon groups and sulfur-containing cycloaliphatic hydrocarbon groups may contain hetero atoms other than sulfur, such as oxygen or nitrogen atoms. Meanwhile, from the standpoint of synthesis simplicity, aliphatic hydrocarbon groups are preferred. Of these, a hydrogen atom and aliphatic hydrocarbon groups are preferred, and a hydrogen atom is especially preferred.

(2-3) Functional Group $Q^2$ $Q^2$ represents a sulfur-containing aliphatic hydrocarbon group which has a valence of (n2+1) and may contain a hetero atom other than sulfur. The inclusion of a sulfur-containing aliphatic hydrocarbon group in $Q^2$ is preferred from the standpoint of heightening the Abbe's number of the polymerizable inorganic-particle dispersant. From the standpoint of the stability of the polymerizable inorganic-particle dispersant, it is preferred that the sulfur-containing aliphatic hydrocarbon group should be a sulfur-containing saturated aliphatic hydrocarbon group.

The molecular weight of $Q^2$ is usually 160 or higher, preferably 170 or higher, more preferably 180 or higher, and is usually 2,000 or less, preferably 1,500 or less, more preferably 1,300 or less. Molecular weights of the sulfur-containing aliphatic hydrocarbon group not lower than the lower limit are preferred from the standpoint that this compound has low volatility, while molecular weights thereof not higher than the upper limit are preferred from the standpoint that this compound has excellent solubility (compatibility).

The proportion of the sulfur atoms contained in $Q^2$ is usually 20% by mass or higher, preferably 30% by mass or higher, more preferably 35% by mass or higher, in terms of sulfur atom content. The proportion thereof is usually 90% by mass or less, preferably 85% by mass or less, more preferably 80% by mass or less. Proportions of the sulfur atoms contained in the sulfur-containing aliphatic hydrocarbon group which are not less than the lower limit are preferred from the standpoint that an improvement in refractive index is attained. Proportions thereof not higher than the upper limit are preferred from the standpoint that this compound has high stability.

Although $Q^2$ is a sulfur-containing aliphatic hydrocarbon group which may contain a hetero atom other than sulfur atom, the term "sulfur-containing aliphatic hydrocarbon group" means an aliphatic hydrocarbon group in which at least one of the carbon atoms constituting the group has been replaced with a sulfur atom. Preferred of such groups is an aliphatic hydrocarbon group in which at least one of the methylene groups constituting the group has been replaced with a divalent group including a sulfur atom.

The expression "may contain a hetero atom other than sulfur atom" means that part of the carbon atoms constituting the sulfur-containing aliphatic hydrocarbon group may have been further replaced with one or more hetero atoms other than sulfur atom. Preferably, that expression means that part of the methylene groups constituting the sulfur-containing aliphatic hydrocarbon group may have been replaced with one or more divalent groups including a hetero atom other than sulfur atom.

The hetero atom other than sulfur atom is not particularly limited. However, the hetero atom preferably is one or more of an oxygen atom, a phosphorus atom, and a nitrogen atom, and more preferably is an oxygen atom and/or a nitrogen atom.

Examples of the structure formed by replacing part of the carbon atoms constituting an aliphatic hydrocarbon group with a sulfur atom and optionally with other hetero atom(s) include a structure formed by replacing any methylene group of an aliphatic hydrocarbon group with a divalent group including a sulfur atom. Examples of the divalent group including a sulfur atom include: a sulfur-containing group such as a sulfide group, disulfide group, or trisulfide group; a sulfur- and oxygen-containing group such as a sulfoxide group, sulfone group, thioester group, thionoester group, or thiocarbonyl group; a sulfur- and phosphorus-containing group such as a thiophosphono group or a dithiophosphono group; and a sulfur- and nitrogen-containing group such as a thioamide group or a thiourea group. Examples of that structure further include these structures which have undergone further replacement with a divalent group containing one or more hetero atoms, such as an oxygen-containing group, e.g., a carbonyl group or an ester group, the oxygen- and phosphorus-containing group shown below,

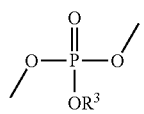

[Chem. 34]

or either of the nitrogen-containing groups shown below.

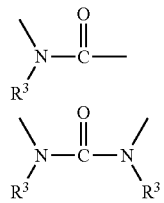

[Chem. 35]

In the formulae shown above, $R^3$ is not particularly limited, and examples thereof include a hydrogen atom and a hydrocarbon group which may have a hetero atom. The number of carbon atoms of the hydrocarbon group which may have a hetero atom is usually 6 or less, preferably 4 or less, more preferably 3 or less, and is usually 1 or larger.

Preferred of such hydrocarbon groups which may have a hetero atom are sulfur-containing chain aliphatic hydrocarbon groups or sulfur-containing cycloaliphatic hydrocarbon groups, from the standpoints of refractive index and Abbe's number. These sulfur-containing chain aliphatic hydrocarbon groups and sulfur-containing cycloaliphatic hydrocarbon groups may contain hetero atoms other than sulfur, such as oxygen or nitrogen atoms. Meanwhile, from the standpoint of synthesis simplicity, aliphatic hydrocarbon groups are preferred. Of these, a hydrogen atom and aliphatic hydrocarbon groups are preferred, and a hydrogen atom is especially preferred.

The sulfur-containing aliphatic hydrocarbon group represented by $Q^2$ in general formula (II), represents a group formed by replacing part of an aliphatic hydrocarbon group in which the number of carbon atoms is usually 3 or larger, more preferably 4 or larger, and is usually 20 or less, preferably 15 or less, more preferably 12 or less, with one or more sulfur atoms and optionally with one or more hetero atoms other than sulfur atom. It is preferred that $Q^2$ should represent a group formed by replacing part of the methylene groups constituting the aliphatic hydrocarbon group with one or more divalent groups including a sulfur atom and optionally with one or more divalent groups including a hetero atom other than sulfur atom.

The aliphatic hydrocarbon group as the base may have either a chain structure or a cyclic structure or have a cyclic structure having a chain structure as a substituent.

In the case of a chain structure, this structure preferably is a linear or branched aliphatic hydrocarbon group which satisfies the range of the number of carbon atoms. In the case of a cyclic structure having a chain structure as part thereof, it is preferred that the number of carbon atoms including the carbon atoms constituting the chain structure contained therein should be within that range.

Examples of the sulfur-containing aliphatic hydrocarbon group include a sulfur-containing cycloaliphatic hydrocarbon group and a sulfur-containing chain aliphatic hydrocarbon group. Preferred is a sulfur-containing cycloaliphatic hydrocarbon group, from the standpoint that the content of sulfur atoms per unit volume of the molecule can be increased. The sulfur-containing cycloaliphatic hydrocarbon group and the sulfur-containing chain aliphatic hydrocarbon group are explained below in detail.

(2-3-1) Sulfur-Containing Cycloaliphatic Hydrocarbon Group

The sulfur-containing cycloaliphatic hydrocarbon group may have a chain structure as a substituent. In the case where the sulfur-containing cycloaliphatic hydrocarbon group has a chain structure, this hydrocarbon group may be bonded to A and/or B either through the chain structure or not through the chain structure. However, bonding through the chain structure is preferred from the standpoint of ease of production.

Preferred as the chain structure is a sulfur-containing chain aliphatic hydrocarbon group which may have a hetero atom such as oxygen or nitrogen, from the standpoint of attaining both refractive index and Abbe's number. The molecular weight of the sulfur-containing cycloaliphatic hydrocarbon group, in terms of the molecular weight thereof including that of, if any, substituent, is usually 160 or higher, preferably 170 or higher, more preferably 180 or higher, and is usually 2,000 or less, preferably 1,500 or less, more preferably 1,300 or less. Molecular weights of the sulfur-containing cycloaliphatic hydrocarbon group not lower than the lower limit are preferred from the standpoint that this compound has low volatility, while molecular weights thereof not higher than the upper limit are preferred from the standpoint that this compound has excellent solubility (compatibility).

The sulfur-containing cycloaliphatic hydrocarbon group preferably is a group formed by replacing part of the methylene groups constituting an aliphatic hydrocarbon group in which the number of carbon atoms, including the carbon atoms of, if any, substituent, is usually 3 or larger, more preferably 4 or larger, and is usually 20 or less, preferably 15 or less, more preferably 12 or less, with one or more divalent groups including a sulfur atom and optionally with one or more divalent groups including a hetero atom other than sulfur atom.

The proportion of the sulfur atoms contained in the sulfur-containing cycloaliphatic hydrocarbon group is usually 20% by mass or higher, preferably 30% by mass or higher, more preferably 35% by mass or higher, in terms of sulfur atom content. The proportion thereof is usually 90% by mass or less, preferably 85% by mass or less, more preferably 80% by mass or less. Proportions of the sulfur atoms contained in the sulfur-containing cycloaliphatic hydrocarbon group which are not less than the lower limit are preferred from the standpoint of an increase in refractive index, while proportions thereof not higher than the upper limit are preferred because this compound has high stability.

Preferred of such sulfur-containing cycloaliphatic hydrocarbon groups is a sulfur-containing cycloaliphatic hydrocarbon group represented by the structure of formula (III).

[Chem. 36]

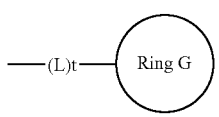

(III)

In formula (III), ring G represents a saturated, 3- to 8-membered monocycle or bridged ring or represents a fused ring or spiro ring which is composed of two or three such monocycles or bridged rings bonded together, wherein part of the methylene groups constituting the ring has been replaced with one or more divalent groups including a sulfur atom. Part of the methylene groups constituting the ring may have been further replaced with one or more divalent groups including a hetero atom such as an oxygen atom, a nitrogen atom, or a phosphorus atom.

L represents a direct bond, a sulfide group, an ether group, or an aliphatic hydrocarbon group which may have a hetero atom, and the multiple L moieties contained in the molecule may be the same or different. Symbol t is (n1+m1) (wherein m1 and n1 have the same meanings as in formula (I)). Incidentally, the inorganic particle dispersant in which $Q^2$ is a sulfur-containing cycloaliphatic hydrocarbon group represented by the structure of formula (III) is a preferred novel compound.

Ring G

Ring G represents a saturated, 3- to 8-membered monocycle or bridged ring or represents a fused ring or spiro ring which is composed of two or three such monocycles or bridged rings bonded together, wherein part of the methylene groups constituting the ring has been replaced with one or more divalent groups including a sulfur atom. Part of the methylene groups constituting the ring may have been further replaced with one or more divalent groups including a hetero atom such as an oxygen atom, a nitrogen atom, or a phosphorus atom.

Examples of the monocycle include thiirane (which is excluded when A is a thiirane group), dithiirane, thietane, 1,2-dithietane, 1,3-dithietane, trithietane, thiolane, 1,2-dithiolane, 1,3-dithiolane, 1,2,3-trithiolane, 1,2,4-trithiolane, tetrathiolane, the sulfur-containing cycloaliphatic hydrocarbons of the structures shown below, 1,2-dithiane, 1,3-dithiane, 1,4-dithiane, 1,2,3-trithiane, 1,2,4-trithiane, 1,3,5-trithiane, 1,2,3,4-tetrathiane, 1,2,4,5-tetrathiane, bis(1,2,3,5,6-pentathiepano)methane, tris(1,2,3,5,6-pentathiepano)methane, thiepane, 1,2-dithiepane, 1,3-dithiepane, 1,4-dithiepane, 1,2,3-trithiepane, 1,2,4-trithiepane, 1,2,5-trithiepane, 1,3,5-trithiepane, 1,2,3,4-tetrathiepane, 1,2,3,5-tetrathiepane, 1,2,4,5-tetrathiepane, 1,2,4,6-tetrathiepane, 1,2,3,4,5-pentathiepane, 1,2,3,4,6-pentathiepane, 1,2,3,5,6-pentathiepane, and hexathiepane.

[Chem. 37]

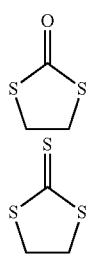

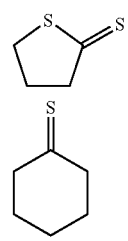

Examples of the bridged ring include the sulfur-containing cycloaliphatic hydrocarbons of the structures shown below.

[Chem. 38]

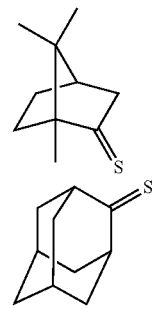

Examples of the fused ring composed of two or three such monocycles or bridged rings bonded together include the sulfur-containing cycloaliphatic hydrocarbons of the structures shown below.

[Chem. 39]

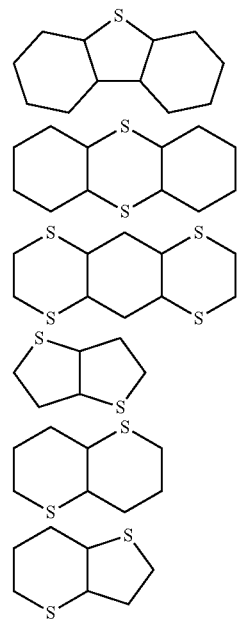

Examples of the spiro ring composed of two or three such monocycles or bridged rings bonded together include 1,4-dithiaspiro[4.5]decane, 1,5-dithiaspiro[5.5]undecane, 2,4,8,10-tetrathiasaspiro[5.5]undecane, and the sulfur-containing cycloaliphatic hydrocarbons of the structures shown below.

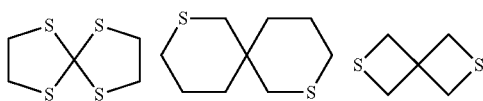

Furthermore, it is preferred that the sulfur-containing cycloaliphatic hydrocarbon should include at least one of a dithiane ring, a dithiolane ring, a trithiolane ring, a thiaspiro ring, a dithiaspiro ring, a trithiaspiro ring, a tetrathiaspiro ring, a dithietane ring, a thiirane ring, and a thiolane ring, from the standpoint that the content of sulfur atoms per unit volume of the molecule can be increased.

Of these, the sulfur-containing cycloaliphatic hydrocarbon groups of the structures shown below are preferred from the standpoint that these hydrocarbons are easy to produce industrially, are stable compounds, and are suitable for easily obtaining optical properties.

[Chem. 41]

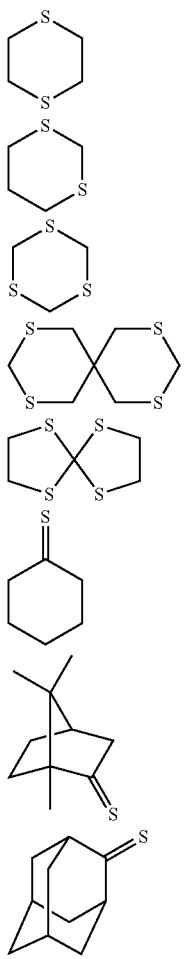

Moreover, the sulfur-containing cycloaliphatic hydrocarbon groups of the structures shown below are preferred from the standpoint that these hydrocarbons enable efficient introduction of sulfur atoms and facilitate control of optical properties.

[Chem. 42]

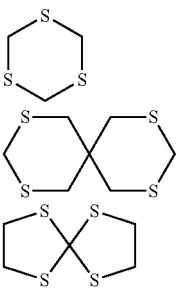

L

L represents a direct bond, a sulfide group, an ether group, or an aliphatic hydrocarbon group which may have a hetero atom, and the multiple L moieties contained in the molecule may be the same or different. The number of carbon atoms of the aliphatic hydrocarbon group which may have a hetero atom is usually 1 or larger and is usually 6 or less, preferably 5 or less, more preferably 4 or less, even more preferably 3 or less.

From the standpoints of ease of production and the stability of the compound, a hydrocarbon group which may have a hetero atom is preferred. Preferred as the hydrocarbon group which may have a hetero atom is an aliphatic hydrocarbon group which may have a hetero atom. More preferred is a sulfur-containing chain aliphatic hydrocarbon group which may have a hetero atom other than sulfur. Even more preferred is the sulfur-containing aliphatic hydrocarbon group which will be described later under (2-3-2).

In the case where the cyclic structure of the sulfur-containing cycloaliphatic hydrocarbon group is bonded to A, it is preferred that L should have the structure —C—S—, —C—C—S—, —C—O—, or —C—C—O—. In the case where the cyclic structure of the sulfur-containing cycloaliphatic hydrocarbon group is bonded to B, it is preferred that L should have the structure —C—S—, —C—C—S—, —C—S—C—, —C—, —C—O—, —C—C—O—, or —C—O—C—. In each of these expressions, the left-hand side is the portion bonded to the cyclic structure and the right-hand side is the portion bonded to A or B.

Preferred of those are structures in which the number of carbon atoms is small, from the standpoint of increasing the content of sulfur atoms. Furthermore, structures in which none of the sulfur atoms contained in the cyclic structure forms a thioacetal structure with any sulfur atom contained in the substituents are preferred because this compound is stable.

Preferred examples of $Q^2$ include the following structures.

[Chem. 43]

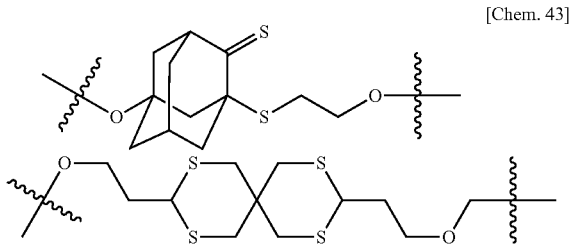

(2-3-2) Sulfur-Containing Chain Aliphatic Hydrocarbon Group

The molecular weight of the sulfur-containing chain aliphatic hydrocarbon group, in terms of the molecular weight thereof including that of, if any, substituent, is usually 60 or higher, preferably 80 or higher, more preferably 90 or higher, and is usually 1,000 or less, preferably 500 or less, more preferably 300 or less. Molecular weights of the sulfur-containing chain aliphatic hydrocarbon group not less than the lower limit are preferred from the standpoint that this compound has low volatility, while molecular weights thereof not higher than the upper limit are preferred from the standpoint that this compound has excellent solubility (compatibility).

It is preferred that the sulfur-containing chain aliphatic hydrocarbon group should be a group formed by replacing part of an aliphatic hydrocarbon framework in which the number of carbon atoms, including the carbon atoms of, if any, substituent, is usually 1 or larger, preferably 2 or larger, more preferably 3 or larger, and is usually 20 or less, preferably 15 or less, more preferably 10 or less, with one or more sulfur atoms and optionally with one or more hetero atoms other than sulfur atom.

The proportion of the sulfur atoms contained in the sulfur-containing chain aliphatic hydrocarbon group is usually 20% by mass or higher, preferably 30% by mass or higher, more preferably 35% by mass or higher, in terms of sulfur atom content. The proportion thereof is usually 90% by mass or less, preferably 85% by mass or less, more preferably 80% by mass or less.

Proportions of the sulfur atoms contained in the sulfur-containing chain aliphatic hydrocarbon group which are not lower than the lower limit are preferred from the standpoint of enabling the inorganic particle dispersant to combine a high refractive index and a high Abbe's number. Proportions thereof not higher than the upper limit are preferred from the standpoint that the coloration of the inorganic particle dispersant is only slight. The case where the sulfur-containing aliphatic hydrocarbon group is a sulfur-containing chain aliphatic hydrocarbon group is preferred from the standpoints of solubility and easy impartation of flexibility to the cured object.

Preferred of such sulfur-containing chain aliphatic hydrocarbon groups is a sulfur-containing chain aliphatic hydrocarbon group represented by the structure of formula (IV).

$$-[S]_p-[CR_2]_q-[E]_r- \quad (V)$$

In formula (IV), R represents a hydrogen atom or a hydrocarbon group which may contain a hetero atom, and E represents an oxygen atom. Symbol p represents an integer of 1-3, q represents an integer of 1-3, and r represents 0 or 1. The multiple R moieties contained in the molecule may be the same or different. The S, $CR_2$, and E in formula (IV) may have been bonded in any sequence. The number of carbon atoms of the hydrocarbon group which may have a hetero atom is usually 6 or less, preferably 4 or less, more preferably 3 or less, and is usually 1 or larger. Preferred of such hydrocarbon groups which may have a hetero atom are sulfur-containing chain aliphatic hydrocarbon groups or sulfur-containing cycloaliphatic hydrocarbon groups, from the standpoints of refractive index and Abbe's number. These sulfur-containing chain aliphatic hydrocarbon groups and sulfur-containing cycloaliphatic hydrocarbon groups may contain hetero atoms other than sulfur, such as oxygen or nitrogen. Meanwhile, from the standpoint of synthesis simplicity, aliphatic hydrocarbon groups are preferred. Of these, a hydrogen atom and aliphatic hydrocarbon groups are preferred, and a hydrogen atom is especially preferred.

Examples of the sulfur-containing chain aliphatic hydrocarbon groups include groups having the structure —S—C—C—S—C—O— or —S—C—C—O—, an ethylenethio group, an ethylenethioethylene group, a methylenedithio group, a methylenetrithio group, and the groups shown below. However, the sulfur-containing chain aliphatic hydrocarbon groups are not limited to these. In the following structural formulae, each straight-line portion with a wavy line affixed thereto is a portion bonded to A or B.

[Chem. 44]

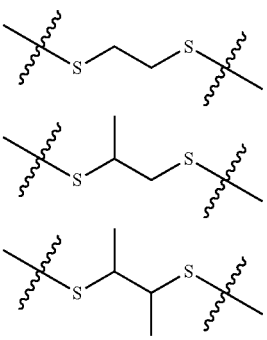

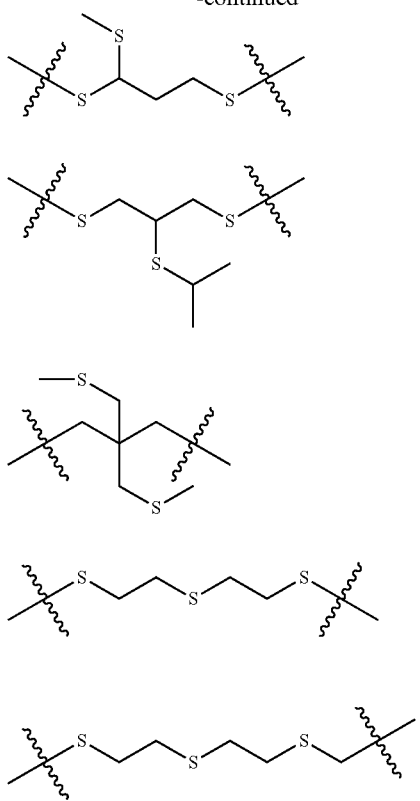

Preferred of these are an ethylenethio group, an ethylenethioethylene group, and the groups shown below.

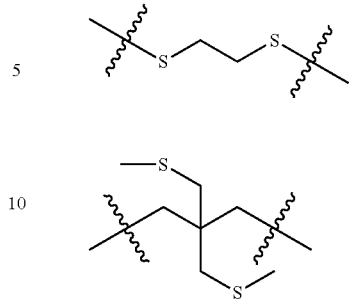

Due to the inclusion of such $Q^2$ in the polymerizable inorganic-particle dispersant of the invention, it becomes possible to stably disperse inorganic particles in a desired dispersion medium so as to result in transparency, and it becomes possible to impart a high Abbe's number while maintaining the high refractive index possessed by the inorganic particles, making it possible to perform refractive-index control and Abbe's-number control in a high-refractive-index range due to the inorganic particles.

<n2, m2>

In formula (II), n2 represents an integer of 1-10, and is preferably an integer of 1-6, more preferably an integer of 1-3, and m2 represents an integer of 2-10, and is preferably an integer of 2-6, more preferably an integer of 2 or 3. Although n2 and m2 need to be 1 or larger, too large numbers are undesirable because the polymerizable inorganic-particle dispersant has a reduced refractive index.

Preferred examples of the compound represented by formula (II) include the following compounds.

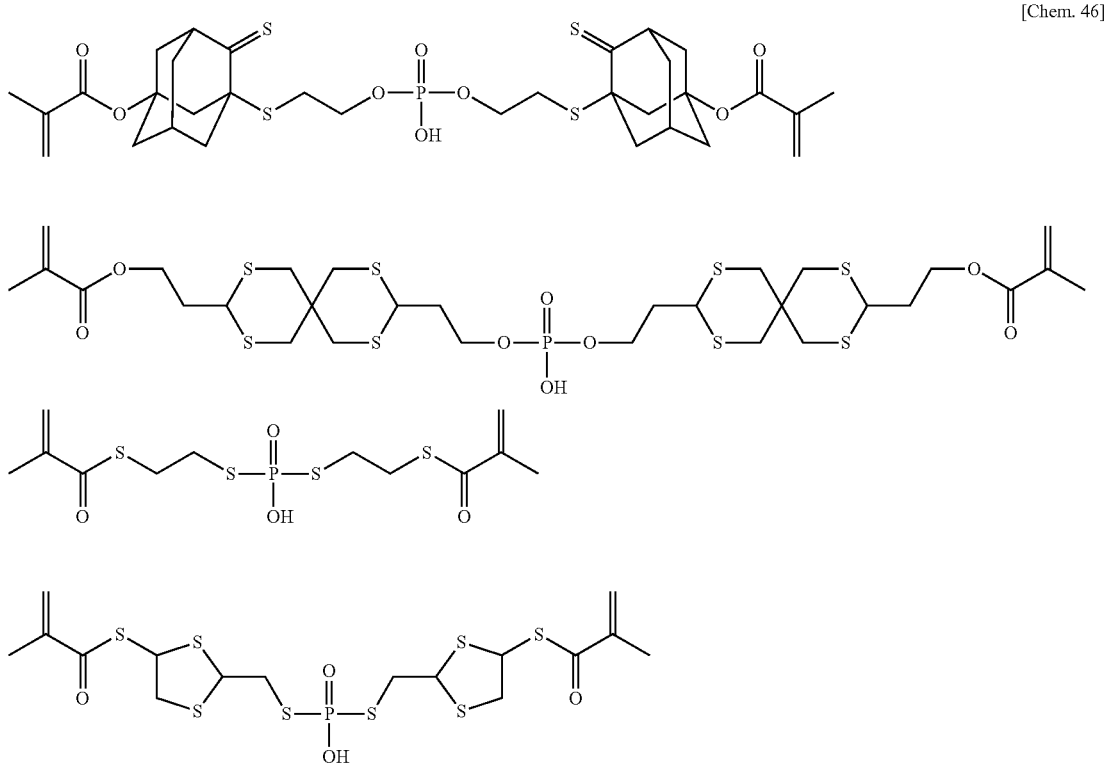

-continued

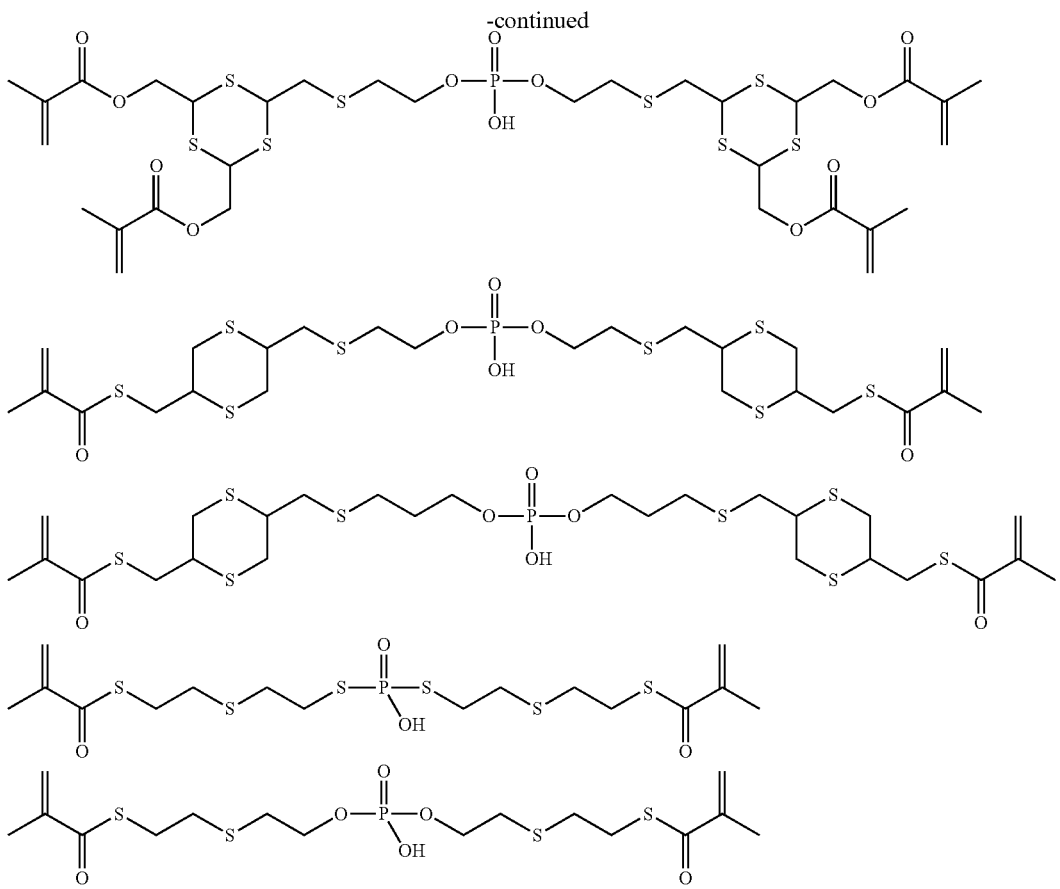

3. Properties of the Polymerizable Inorganic-Particle Dispersant
(1) Refractive Index The polymerizable inorganic-particle dispersant of the invention has a refractive index of usually 1.62 or higher, preferably 1.65 or higher, more preferably 1.7 or higher. Although there is no particular upper limit on the refractive index thereof, the refractive index thereof is usually 2.0 or less. Due to the refractive index of 1.62 or higher, the inorganic-organic composite particles obtained are inhibited from having a reduced apparent refractive index and it is easy to control the refractive index of the inorganic-organic resin composite material in a wide range of high refractive indexes of nd=1.65 and higher. In this description, in the case where optical properties of the polymerizable inorganic-particle dispersant or of the inorganic-organic composite particles are mentioned, these optical properties mean the optical properties of the inorganic-organic resin composite material produced using these.

The reasons for the necessity of refractive-index control in such a high-refractive index range include, for example, that the minimum reflectance required in the case of use in anti-reflection application can be further reduced. Namely, a technique which is being employed for preventing reflection from various substrates is to form a film having a low refractive index on the substrate to make the light reflected by the surface of the low-refractive-index layer have a phase which is the inverse of the phase of the light reflected by the interface between the layer and the substrate, thereby eliminating the light.

Under the current circumstances, however, a film constituted of such a low-refractive-index layer alone is unable to completely prevent reflection. This is because the reflection prevention depends on both the refractive index of the substrate and the refractive index of the low-refractive-index layer, and in the case of a substrate having a refractive index of, for example, 1.63, complete prevention of reflection necessitates formation of a low-refractive-index film having a refractive index of about 1.28. At present, there is no polymeric material which by itself is capable of forming such a low-refractive-index film.

Meanwhile, a method for more highly preventing reflection is known in which a material having a low refractive index and a material having a high refractive index are superposed to thereby prevent reflection over a wide wavelength range. In this method, a high-refractive-index layer is interposed between the substrate and a low-refractive-index layer. However, since the refractive index of the substrate and the refractive index of the low-refractive-index layer vary, the high-refractive-index layer to be interposed therebetween also requires refractive-index control according to those refractive indexes.

For example, in the case where a low-refractive-index film having a refractive index of about 1.4, which is available at present, is used as the low-refractive-index layer and a substrate having a refractive index of about 1.5 is used as the substrate, the high-refractive-index layer to be interposed therebetween is required to have a refractive index of 1.6-1.7, for obtaining an antireflection effect. Consequently, a refractive index of at least 1.6 or higher, more preferably 1.62 or higher, is necessary for enabling regulation of refractive index.

From the standpoint of making the polymerizable inorganic-particle dispersant have a refractive index of 1.62 or higher, it is preferred that atoms or functional groups which contribute to an increase in refractive index should be contained in the polymerizable inorganic-particle dispersant. Examples of the atoms or functional groups which contribute to an increase in refractive index include sulfur atoms, atoms of halogens excluding fluorine, nitrogen atoms, and phenyl groups. From the standpoint of high Abbe's number, however, halogen atoms and phenyl groups are undesirable, and it is preferred that the dispersant should have sulfur atoms.

<Methods for Measuring Refractive Index>

Examples of methods for measuring refractive index usually include direct measurement with a commercial Abbe's meter, and further include, especially for thin-film samples, a method in which a reflectance measurement through a film thickness measurement with a spectral film thickness meter is made at different wavelengths and the refractive index is determined from the reflectances, and a method in which an ellipsometer is used to measure the phase difference $\Delta$ between the p-polarized component and s-polarized component of light and further measure the reflection amplitude ratio angel $\Phi$ and the measured values are analyzed using any of optical models. In the invention, refractive index means the value determined with a spectral film thickness meter.

In the case of determining refractive index with a spectral film thickness meter, the found values are subjected to fitting with the Cauchy model and the refractive indexes $n_F$, $n_d$, and $n_C$ at respective wavelengths (486 nm (F-line), 587 nm (d-line), and 656 nm (C-line)) can be thereby calculated.

As will be described in the section Examples given later, the refractive index of the polymerizable inorganic-particle dispersant of the invention is determined by examining a cured film obtained by adding 0.001-1% by mass the polymerization initiator which will be described later to a solution that contains the polymerizable inorganic-particle dispersant in an amount of 1-10% by mass, using the resultant composition to form a thin film, and irradiating this thin film with ultraviolet rays.

In the invention, the term refractive index means $n_d$. However, it is preferred that the refractive indexes $n_F$ and $n_C$ also should be 1.62 or higher.

(2) Abbe's Number

The polymerizable inorganic-particle dispersant of the invention has an Abbe's number of 40 or higher, preferably 45 or higher, more preferably 50 or higher. Abbe's numbers of the polymerizable inorganic-particle dispersant less than 40 are undesirable because it is difficult to attain both a high refractive index and a high Abbe's number in the case where this dispersant is composited with inorganic particles. In addition, such too low Abbe's numbers are undesirable because this dispersant, when used to produce inorganic-organic composite particles and to obtain an inorganic-organic resin composite material, is reduced in the effect of imparting a high Abbe's number to the composite material. Although there is no particular upper limit on the Abbe's number thereof, the Abbe's number thereof is usually 60 or less.

Here, Lorentz-Lorentz's formula, which characterizes the refractive index and molecular structure of a compound, is known. According to this formula, the refractive index of a polymer is represented by the following equation (1), which is derived from the molecular volume V and molecular refraction [R] of the repeating unit thereof.

$$n=\sqrt{(2[R]/V+1)/(1-[R]/V)} \quad (1)$$

Meanwhile, the Abbe's number $v_d$ is represented by the following equation (2), when the refractive indexes measured with C-line (656 nm), d-line (587 nm), and F-line (486 nm) are expressed by $n_C$, $n_d$, and $n_F$, respectively.

$$v_d=(n_d-1)/(n_F-n_C) \quad (2)$$

Using the value of atomic dispersion given in Kaguku Binran, the Abbe's number $v_d$ is represented by the following equation, in which molecular dispersion is expressed by $[\Delta R]$ and which is derived from equations (1) and (2).

$$v_d=6n_d/(n_d^2+2)(n_d+1)\times[R]/[\Delta R] \quad (3)$$

Here, the molecular dispersion is the sum of the dispersions of the atoms constituting the molecule. Consequently, in order for a resin to have a high Abbe's number, the resin needs to contain a large amount of atoms which have a large atomic dispersion [R] and which give a small molecular dispersion $[\Delta R]$. Halogen atoms other than F and sulfur atoms (having a large [R] and giving a small $[\Delta R]$) are optimal.

Of these, the halogen atoms tend to be restricted in the use thereof from the standpoints of environmental issues, etc. and are harmful. Sulfur atoms are hence preferred for use in heightening the Abbe's number. Consequently, suitable as Q in the polymerizable inorganic-particle dispersant of the invention is a group containing sulfur atoms.

4. Processes for Producing the Polymerizable Inorganic-Particle Dispersant

Processes for producing the compound including A, B, and Q, which is the polymerizable inorganic-particle dispersant of the invention, are not particularly limited so long as a structure including A, B, and Q bonded together is obtained. The compound can be obtained by bonding A, B, and Q, which are known groups, by a known method.

Specifically, use may be made of a method in which A and Q are bonded to each other to obtain a compound of the structure A-Q and B is thereafter bonded to the Q of the compound of the structure A-Q, or a method in which B and Q are bonded to each other to obtain a compound of the structure Q-B and A is thereafter bonded to the Q of the compound of the structure Q-B.

In the case where B has a valence of 2 or higher, it is preferred to conduct bonding between A and Q first, because this method facilitates the production. Also in view of the fact that B is a highly polar group to render purification of the reaction product difficult, it is preferred to first conduct bonding between A and Q.

In the case of forming a bond between A and B, it is preferred to bond one of these to Q and then bond the other.

Methods for bonding A and Q to each other, for bonding Q and B to each other, and for bonding A and B to each other are explained below.

(1) Methods for Bonding A and Q to Each Other

Although examples of the polymerizable functional group A include a (meth)acrylic group, oxirane group, thiirane group, and isocyanate group, methods for linking to Q are explained below with respect to (meth)acrylic group, which is a preferred polymerizable functional group in the invention, as an example.

The most common method for introducing a (meth)acrylic group is to react a (meth)acrylic acid derivative with a hydroxyl group or a mercapto group. Namely, a (meth)acrylic acid derivative is reacted, in the presence of an adequate catalyst or reaction agent, with a sulfur-containing divalent or more aliphatic hydrocarbon group Q which may contain a hetero atom other than sulfur and into which a hydroxyl group or a mercapto group has been introduced beforehand, thereby obtaining the desired product.

The "hydroxyl group or mercapto group prepared beforehand" to be used in the method described above may be in the form of the oxygen atom or sulfur atom which constitutes part of either the L contained in formula (III) described above or the E contained in formula (IV) described above. Specific examples include methods 1 to 5 shown below.

Method 1: Method in which (Meth)Acrylic Acid as (Meth) Acrylic Acid Derivative is Subjected to Esterification Reaction with the Hydroxyl Group of Q Examples of the reaction of (meth)acrylic acid with a hydroxyl group are shown in JP-A-2011-201937, JP-A-2012-36138, etc.

Method 2: Method in which (Meth)Acrylic Group is Introduced by Transesterification Reaction Using Ester, Such as Methyl (Meth)Acrylate, as (Meth)Acrylic Acid Derivative Examples of the reaction of an ester with a hydroxyl group are shown in JP-A-2011-201937, JP-A-1-258642, JP-A-4-66555, etc.

Method 3: Method in which (Meth)Acrylic Group is Introduced by Conducting Esterification Using Acid Halide, Such as (Meth)Acryloyl Chloride, as (Meth)Acrylic Acid Derivative Examples of the reaction between an acid halide and a hydroxyl group are shown in JP-A-2011-201937, JP-A-2000-119220, etc., and examples of the reaction between an acid halide and a mercapto group are shown in JP-A-2-3675, JP-A-2-229808, JP-A-3-11054, etc.

Method 4: Method in which (Meth)Acrylic Anhydride is Used as (Meth)Acrylic Acid Derivative Examples of the reaction between (meth)acrylic anhydride and a hydroxyl group are shown in JP-A-2-229808, JP-A-3-11054, etc. An example of the reaction between (meth)acrylic anhydride and a mercapto group is shown in JP-A-11-35522.

Method 5: Method in which 3-Halopropionyl Halide is Reacted with Hydroxyl Group or Mercapto Group and the Resultant 3-Halopropionic Acid Ester is Dehydrohalogenated to Form (Meth)Acrylic Group A sulfur-containing divalent or more aliphatic hydrocarbon group Q which may contain a hetero atom other than sulfur and into which a hydroxyl group or a mercapto group has been introduced beforehand is reacted with a halopropionyl halide and the halopropionic acid ester obtained is dehydrohalogenated, thereby obtaining Q which has a (meth) acrylic group.

Examples of the reaction between a halopropionyl halide and a hydroxyl group are shown in JP-A-2011-201937, JP-A-2006-232797, etc. Examples of the reaction between a halopropionyl halide and a mercapto group are shown in JP-A-2-172969, etc.

Methods for introducing a (meth)acrylic group are not limited to these methods. These methods can be suitably selected in accordance with the desired structure of Q and the reactivity thereof. Furthermore, other polymerizable functional groups also can be linked to the desired Q using known methods.

(2) Methods for Bonding B and Q to Each Other

Methods for linking to Q are explained below with respect to the following structures as examples, which are preferred in the invention as portion B, which is adsorbed onto inorganic particles.

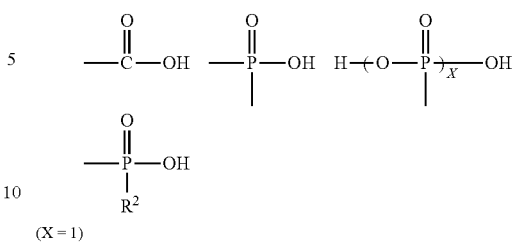

(X = 1)

(2-1) The Case where B is the Following Structure 1

Structure 1

Method 6: Method in which Q having haloalkyl structure is induced to Grignard compound, $CO_2$ is caused to add thereto to obtain carbonate structure having a larger number of carbon atoms, and the system is acidified to thereby obtain carboxyl group.

A specific recipe including a similar substrate is described in the following non-patent document.

*Organic Synthesis*, Collective Volume 6, pp. 845-853, 1988

Method 7: Method based on Michael addition reaction between Q having hydroxyl group or mercapto group and olefin having electron-attracting group.

Methods in which similar substrates are used and acrylic acid is used as the olefin having an electron-attracting group are shown in JP-A-2008-174506 and the following non-patent document.

*Tetrahedron*, Vol. 49, No. 15, pp. 3149-3164, 1993

Methods which use similar substrates and in which acrylonitrile is used to conduct Michael addition and the nitrile group is thereafter hydrolyzed into a carboxyl group are shown in Japanese Patent No. 5031554 and the following non-patent document.

*Synthetic Communications*, Vol. 38, pp. 789-795, 2008

Method 8: There is a method in which Q having a hydroxyl group or mercapto group is reacted with succinic anhydride, and reaction examples using similar substrates are shown in JP-A-2006-273709 and the following non-patent document.

*Organic Synthesis*, Collective Volume 11, pp. 1068-1073, 2009

Method 9: Method in which Q Having Hydroxyl Group or Mercapto Group is Reacted with Chloroacetic Acid Ester and the Ester is then Hydrolyzed The reaction between a hydroxyl group or mercapto group and a chloroacetic acid ester using similar substrates is shown in U.S. Pat. No. 6,080,867, U.S. Pat. No. 5,925,764, and the following non-patent documents.

*Tetrahedron Letters*, Vol. 30, No. 28, pp. 3633-3636, 1989

*Chemical & pharmaceutical bulletin*, Vol. 38, No. 11, pp. 3035-3041, 1990

Methods for the hydrolysis are shown in U.S. Pat. No. 6,303,804, International Publication WO 2010/68242, Chinese Patent No. 102001981, and the following non-patent document.

*Tetrahedron Letters*, Vol. 45, No. 30, pp. 5901-5903, 2004

Methods for introducing structure 1 are not limited to these methods. These methods can be suitably selected in accordance with the desired structure of Q and the reactivity thereof.

(2-2) The Case where B is the Following Structure 2 or 3

[Chem. 49]

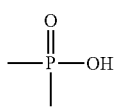

Structure 2

[Chem. 50]

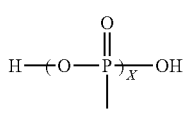

Structure 3

(X = 1)

Known as a method for introducing these structures is a method in which Q having a hydroxyl group or mercapto group is reacted with phosphoryl chloride or thiophosphoryl chloride in the presence of a base to thereby introduce a phosphorus-containing oxo acid structure. Specific methods using similar substrates are shown as examples in JP-A-11-80175, Japanese Patent No. 2735732, etc. In general, the compounds obtained by this method are in the form of a mixture of compounds having structures 2 and 3. In the invention, the mixture of these compounds can be used without being separated.

(2-3) The Case where B is the Following Structure 4

Known as a method for bonding the following structure 4 to Q is a method in which Q having a hydroxyl group or mercapto group is reacted with phosphoryl chloride or thiophosphoryl chloride in the presence of a base. Specifically, a method using a similar substrate is shown as an example in JP-A-5-320181.

[Chem. 51]

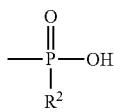

Structure 4

In structure 4, $R^2$ is a hydrogen atom or an aliphatic hydrocarbon group which may have a hetero atom.

Methods for bonding Q and B to each other are not limited to these methods. These methods can be suitably selected in accordance with the desired structure of Q and the reactivity thereof.

The "haloalkyl group" and "hydroxyl group or mercapto group" to be used in the methods described above each may be in the form of the carbon atom, oxygen atom, or sulfur atom which constitutes part of either the L contained in formula (III) described above or the E contained in formula (IV) described above.

(3) Methods for Bonding A and B to Each Other

In the case where portion B, which is adsorbed onto inorganic particles, is divalent or more, it is possible to directly bond the polymerizable functional group A to B. Examples of methods usable in this case include a method in which any of methods 1 to 5 described above is applied to the hydroxyl group or mercapto group introduced beforehand into B. As other examples, a method for synthesizing a similar compound by a reaction between (meth)acrylic anhydride and a phosphoric acid salt is shown as an example in the following non-patent document, and a method for synthesizing a similar compound by reacting diphosphorus pentoxide with (meth) acrylic acid or allyl alcohol is shown as an example in International Publication WO 2004/049068.

*Bioorganic Chemistry*, Vol. 17, No. 1, pp. 1-12, 1989

Methods for linking the polymerizable functional group A to portion B which is divalent or more and is adsorbed onto inorganic particles are not limited to these methods. These methods can be suitably selected in accordance with the desired structures of A and B and the reactivity thereof. The "hydroxyl group or mercapto group prepared beforehand" to be used in the methods shown above may be in the form of the oxygen atom or sulfur atom which constitutes part of either the L contained in formula (III) described above or the E contained in formula (IV) described above.

5. Inorganic Particles (1) Refractive Index of the Inorganic Particles

The inorganic particles to be used in the inorganic-organic composite particles of the invention are not particularly limited and can be selected at will from known inorganic particles. However, inorganic particles having a high refractive index are preferred. The refractive index thereof is usually 2.0 or higher, preferably 2.2 or higher. Although there is no particular upper limit on the refractive index of the inorganic particles, the refractive index thereof is usually 3.0 or less.

Specifically, it is preferred that the inorganic particles should be zirconium oxide (refractive index, 2.1-2.2), titanium oxide (refractive index, 2.5-2.7), cerium oxide (refractive index, 2.1), tin oxide (refractive index, 1.9-2.0), niobium oxide (refractive index, 2.3), zinc oxide (refractive index, 2.0), barium titanate (refractive index, 2.4), strontium titanate (refractive index, 2.4), or a composite oxide including at least one metal oxide selected from these metal oxides.

Inorganic particles having a refractive index less than 2.0 are undesirable because such inorganic particles, when used in combination with the polymerizable inorganic-particle dispersant of the invention to produce inorganic-organic composite particles, are poor in the effect of improving refractive index, making it difficult to attain a refractive index of 1.65 or higher in terms of the refractive index of the cured object formed from the inorganic-organic composite particles.

(2) Particle Diameter of the Inorganic Particles

From the standpoint of enabling the inorganic-organic composite particles to retain high transparency, the inorganic particles have a size of preferably 1-10 nm, more preferably 1-5 nm, in terms of particle diameter. The reasons for this are as follows. By regulating the size of the particles to 1 nm or larger, the inorganic particles can be prevented from having a refractive index lower than the refractive index inherent in the inorganic particles, due to the size effect of the inorganic particles, and making it impossible to obtain a high refractive index. By regulating the size thereof to 10 nm or less, transparency can be prevented from becoming unable to be ensured due to Rayleigh scattering.

The term "particle diameter of inorganic particles" herein means the value determined by directly examining the particles with a transmission electron microscope (TEM), measuring the major-axis lengths of arbitrarily selected 200 particles, and averaging the measured lengths.

(3) Processes for Producing the Inorganic Particles

Processes for producing the inorganic particles are not particularly limited. However, a process can be suitably selected from known processes including the solvothermal method conducted in an alcohol solvent, a process in which an alkoxide as a starting material for oxide is atomized and pyrolyzed in a vapor phase, a method in which a metal oxide is directly pulverized, and a method in which a microemulsion is utilized.

Solvothermal Method:
W. Stober, A. Fink and E. Bohn, *J. Colloid Interface Sci.*, Vol. 26, p. 62 (1986)
E. S. Tormey, R. L. Prober, H. K. Bowen and P. D. Calvert, *Advances in Ceramic Society Press.*, Vol. 9, p. 140 (1984)
B. Fegley, Jr., and E. A. Barringer, *Better Ceramics through Chemistry*, Elsevier, p. 187 (1984)

Atomization Pyrolysis Process:
JP-A-63-221842
Funtai Kōgakukai-shi, Vol. 26, No. 3, pp. 169-173 (1989)
Funtai Kōgakukai-shi, Vol. 33, No. 3, pp. 187-191 (1996)

Pulverization Method:
Nanomateriaru Kōgaku Taikei, Vo. 1, "New Ceramics/Glass", Fuji Technosystem, p. 45

Microemulsion:
M. Yanagi, Y. Asano, K. Kandori, K. Kon-no and A. Kitahara, 1986 *Shikizai Kenkyū Happyō-kai Yōshi-shū*, p. 86 (1986)
K. Osseo-Asare and F. J. Arriagada, *Colloids Surfaces*, Vol. 50, p. 321 (1990)
T. Kawai, A. Fujino, and K. Kon-no, *Colloids Surfaces A*, Vol. 109, p. 245 (1996)

In the inorganic-organic composite particles of the invention, one kind of inorganic particles may be used as the only inorganic particles, or it is also possible to use two or more kinds of inorganic particles in combination unless the effects of the invention are lessened thereby.

6. Inorganic-Organic Composite Particles

The inorganic-organic composite particles of the invention are obtained by compositing inorganic particles with the polymerizable inorganic-particle dispersant of the invention.

By compositing the polymerizable inorganic-particle dispersant of the invention with inorganic particles, the refractive index of the inorganic-organic resin composite material to be obtained from the inorganic-organic composite particles of the invention can be improved. Furthermore, a refractive index as high as refractive index $n_d$=1.65 or above can be attained with an inorganic-particle content as low as 20% by mass. In addition, it becomes possible to conduct refractive-index control and Abbe's-number control in wide ranges in a range of refractive indexes of $n_d$=1.65 and higher.

In this compositing, multiple kinds of inorganic particles and multiple kinds of polymerizable inorganic-particle dispersants may be used.

Processes for producing the inorganic-organic composite particles are not particularly limited. However, a wet process is usually employed. The wet process is a method in which inorganic particles are suspended in a solvent and the polymerizable inorganic-particle dispersant is mixed, either directly or in a solution state, with the suspension of the inorganic particles. Thus, it is possible to produce a transparent dispersion in which the inorganic particles have been evenly dispersed.

In the inorganic-organic composite particles of the invention, the amounts of the inorganic particles and polymerizable inorganic-particle dispersant to be incorporated can be set according to purposes on the basis of the refractive indexes of the respective substances. Usually, however, the amount of the inorganic particles based on the polymerizable inorganic-particle dispersant is preferably 20-90% by mass, more preferably 40-85% by mass, even more preferably 60-80% by mass.

By regulating the content of the inorganic particles based on the polymerizable inorganic-particle dispersant to 20% by mass or higher, the effect of improving refractive index is enhanced, making it easy to obtain inorganic-organic composite particles having a refractive index of 1.65 or higher. Such contents of the inorganic particles are hence preferred. Meanwhile, by regulating the content of the inorganic particles based on the polymerizable inorganic-particle dispersant to 90% by mass or less, the inorganic-particle-dispersing effect of the polymerizable inorganic-particle dispersant is enhanced and dispersion stability is improved. Such contents thereof are hence preferred.

The dispersion medium in which inorganic particles are dispersed is not particularly limited. However, when compatibility with the polymerizable inorganic-particle dispersant is taken into account, it is preferred to use an organic solvent. Specific examples thereof include one or more of tetrahydrofuran, toluene, hexane, N-methylpyrrolidone, dimethyl sulfoxide, ethanol, methanol, butanol, propylene glycol monomethyl ether, ethylene glycol monomethyl ether, methyl isobutyl ketone, and the like.

The amount of the dispersion medium based on the inorganic particles is usually 50-99% by mass. By regulating the amount of the dispersion medium based on the inorganic particles to 50% by mass or larger, the inorganic-particle concentration is regulated and the occurrence of gelation, particle precipitation, etc. can be inhibited. Meanwhile, by regulating the amount of the dispersion medium based on the inorganic particles to 99% by mass or less, the time period required for removing the solvent (dispersion medium) when the inorganic-organic composite particles are used as a composition can be shortened, and problems encountered in the solvent removal step, such as gelation and phase separation, can be inhibited from arising.

For suspending inorganic particles in the dispersion medium, the following method may be used. Inorganic particles produced, for example, by the solvothermal method are sedimented in a poor solvent, and the supernatant is removed. Thereafter, the particles are subjected several times to washing with, for example, a 1:1 mixture of a poor solvent for the organic matter adherent to the particle surface and a good solvent therefor, and the wet inorganic particles are recovered with a centrifugal separator. Subsequently, the desired dispersion medium is added thereto.

Methods for mixing the suspension of inorganic particles with the polymerizable inorganic-particle dispersant are not particularly limited. However, use may be made of a method in which the polymerizable inorganic-particle dispersant in a given amount is added to and mixed with the suspension of inorganic particles either directly or in the form of a solution in any solvent. In the case of mixing the polymerizable inorganic-particle dispersant in a solution state, it is preferred that the solvent to be used should be the same as the dispersion medium in which the inorganic particles are suspended.

Conditions for the mixing of the suspension of inorganic particles with the polymerizable inorganic-particle dispersant are not particularly limited. However, examples include a method in which the mixture is stirred at a temperature of 50° C. or lower for about 1-2 hours at atmospheric pressure.

7. Dispersion of the Inorganic-Organic Composite Particles

By the mixing of the suspension of inorganic particles with the polymerizable inorganic-particle dispersant, a dispersion of the inorganic-organic composite particles is obtained. According to purposes, this dispersion can be used as such or can be used after the dispersion medium is removed or replaced with another solvent.

(1) Concentration of the Inorganic-Organic Composite Particles

In the case where the inorganic-organic composite particles obtained by compositing inorganic particles with the polymerizable inorganic-particle dispersant are used as the dispersion, the concentration of the inorganic-organic composite particles in the dispersion of the inorganic-organic composite particles is usually 1-50% by mass, preferably 1-30% by mass.

By regulating the concentration of the inorganic-organic composite particles so as to be not less than the lower limit, the concentration of the inorganic-organic composite particles is rendered sufficient and, even when the dispersion is used for thin-film formation, a film having a sufficient thickness is formed. Such concentrations are hence preferred. By regulating the concentration thereof so as to be not higher than the upper limit, the dispersion of the inorganic-organic composite particles is made to have better stability and be less apt to suffer gelation or the like. Such concentrations are hence preferred.

(2) Composition of Dispersion of the Inorganic-Organic Composite Particles

The proportion of the inorganic particles in the dispersion of the inorganic-organic composite particles is usually 0.2% by mass or higher, preferably 1% by mass or higher, more preferably 2% by mass or higher, based on the dispersion of the inorganic-organic composite particles. Meanwhile, the concentration of the inorganic particles is usually 45% by mass or less, although there is no particular upper limit thereon so long as the inorganic particles can be stably dispersed.

By regulating the concentration of the inorganic particles to 0.2% by mass or higher, the refractive-index-improving effect of the inorganic particles is enhanced. Such concentrations are hence preferred. Conversely, by regulating the concentration thereof to 45% by mass or less, the inorganic-particle-dispersing effect of the polymerizable inorganic-particle dispersant is enhanced and dispersion stability is improved. Such concentrations are hence preferred.

(3) Dispersion Medium

The dispersion medium is not particularly limited. However, as stated above, it is preferred to use an organic solvent, when compatibility with the polymerizable inorganic-particle dispersant is taken into account. Examples thereof include one or more solvents such as tetrahydrofuran, toluene, hexane, N-methylpyrrolidone, dimethyl sulfoxide, ethanol, methanol, butanol, propylene glycol monomethyl ether, ethylene glycol monomethyl ether, methyl isobutyl ketone, or the like.

(4) Other Components

<Dispersant>

In the dispersion of the inorganic-organic composite particles, a dispersant other than the polymerizable inorganic-particle dispersant of the invention may be used. The dispersion may contain one or more known dispersants having an adsorbable portion such as a carboxyl group, phosphorus-containing oxo acid group, or sulfur-containing oxo acid group, unless the effects of the invention are lessened thereby.

<Antioxidant>

The dispersion of the inorganic-organic composite particles may contain a known antioxidant such as a nitrogen-compound or phosphorus-compound antioxidant incorporated thereinto for the purpose of imparting weatherability to the polymerizable inorganic-particle dispersant. In this case, the content of the antioxidant in the dispersion of the inorganic-organic composite particles, based on the polymerizable inorganic-particle dispersant, is usually 0.01% by mass or higher, more preferably 1% by mass or higher, and is usually 5% by mass or less, preferably 4% by mass or less, more preferably 3% by mass or less. By regulating the content of the antioxidant in the dispersion of the inorganic-organic composite particles so as to be not less than the upper limit, the cured object obtained through polymerization reaction can be prevented, over a long period, from taking a color or deteriorating. By regulating the content thereof so as to be not higher than the upper limit, the cured object obtained through polymerization reaction can be inhibited from suffering the decrease in transparency, decrease in refractive index, etc. which are due to the addition of the antioxidant.

<Polymerization Inhibitor>

The dispersion of the inorganic-organic composite particles may contain a polymerization inhibitor incorporated thereinto for the purpose of preventing the polymerizable inorganic-particle dispersant from polymerizing. In this case, the content of the polymerization inhibitor in the dispersion of the inorganic-organic composite particles, based on the polymerizable inorganic-particle dispersant, is usually 0.01% by mass or higher, more preferably 1% by mass or higher, and is usually 5% by mass or less, preferably 4% by mass or less, more preferably 3% by mass or less. By regulating the content of the polymerization inhibitor in the dispersion of the inorganic-organic composite particles so as to be not less than the upper limit, the polymerizable inorganic-particle dispersant can be prevented, over a long period, from gelling in the solution. By regulating the content thereof so as to be not higher than the upper limit, the cured object obtained through polymerization reaction can be inhibited from suffering the decrease in transparency, decrease in refractive index, etc. which are due to the addition of the polymerization inhibitor.

<Others>

The dispersion of the inorganic-organic composite particles may further contain a known viscosity regulator, leveling agent, or the like which is compatible with the polymerizable inorganic-particle dispersant and has been incorporated thereinto for the purpose of improving viscosity or handleability.

8. Inorganic-Organic Resin Composite Material

Since the inorganic-organic composite particles of the invention have polymerizable functional groups A, an inorganic-organic resin composite material is obtained by polymerizing the polymerizable functional groups A. For example, an inorganic-organic resin composite material which is a polymer of the inorganic-organic composite particles can be obtained usually by mixing a polymerization initiator with the inorganic-organic composite particles or with a dispersion thereof and then molding and curing the mixture.

Meanwhile, an inorganic-organic resin composite material can be obtained also by mixing the inorganic-organic composite particles with another polymerizable monomer and then polymerizing the ingredients. For example, an inorganic-organic resin composite material can be obtained also by mixing a starting-material monomer for resin with the inorganic-organic composite particles or with a dispersion thereof, thereafter mixing this mixture with a polymerization initiator which accelerates the polymerization of each ingredient, and molding and curing the resultant mixture.

Processes for producing the inorganic-organic resin composite material are explained below.

8-1. Process for Producing Polymer of the Inorganic-Organic Composite Particles

An inorganic-organic resin composite material which is a polymer of the inorganic-organic composite particles can be obtained usually by mixing a polymerization initiator with the inorganic-organic composite particles or with a dispersion thereof and then molding and curing the mixture.

(1) Polymerization Initiator

The polymerization initiator is used in order to conduct the polymerization reaction of the inorganic-organic composite particles.

Usually, it is preferred that the amount of the polymerization initiator, based on the amount of the polymerizable inorganic-particle dispersant, should be 0.01% by mass or larger, especially 0.1% by mass or larger, in particular 1% by mass or larger, and be usually 20% by mass or less, especially 15% by mass or less, in particularly 10% by mass or less. By using a polymerization initiator in an amount not less than the lower limit, the polymerization is prevented from resulting in a curing failure or in dissolution of unreacted components, and a sufficient refractive index and mechanical strength are obtained. By using a polymerization initiator in an amount not larger than the upper limit, coloration or the like due to the polymerization initiator is prevented and troubles such as phase separation of inorganic particles and the opacification or embrittlement of the cured object can be inhibited.

The polymerization initiator to be used is not particularly limited so long as the polymerization reaction of the polymerizable inorganic-particle dispersant can be conducted therewith. Use can be suitably made of acetophenone compounds, benzophenone compounds, benzoin ethers, hydroxy ketones, acylphosphine oxides, diazonium cation onium salts, iodonium cation onium salts, sulfonium cation onium salts, or the like in accordance with the kind of the polymerizable inorganic-particle dispersant.

Specific examples thereof include 1-[4-(2-hydroxyethoxyl)phenyl]-2-hydroxy-2-methyl-1-propan-1-one, 1-hydroxycyclohexyl phenyl ketone, 2,2-dimethoxy-1,2-diphenylethan-1-one, 2,4,6-trimethylbenzoyldiphenylphosphine oxide, 2,4,6-trimethylbenzoylphenylethoxyphosphine oxide, 2-benzyl-2-dimethylamino-1-(4-morpholinophenyl)butanone-1,2-hydroxy-2-methyl-1-phenylpropan-1-one, 2-methyl-1-[4-methylthio]phenyl]-2-morpholinopropan-1-one, benzoin methyl ether, benzoin ethyl ether, benzoin isobutyl ether, benzoin isopropyl ether, bis(2,4,6-trimethylbenzoyl)-phenylphosphine oxide, 2-hydroxy-2-methyl-[4-(1-methylvinyl)phenyl]propanol oligomers, isopropylthioxanthone, methyl o-benzoylbenzoate, [4-(methylphenylthio)phenyl]phenylmethane, 2,4-diethylthioxanthone, 2-chlorothioxanthone, benzophenone, ethylanthraquinone, benzophenone ammonium salts, thioxanthone ammonium salts, bis(2,6-dimethoxybenzoyl)-2,4,4-trimethylpentylphosphine oxide, 2,4,6-trimethylbenzophenone, 4-methylbenzophenone, 4,4'-bisdiethylaminobenzophenone, 1,4-dibenzoylbenzene, 10-butyl-2-chloroacridone, 2,2'-bis(o-chlorophenyl)-4,5,4',5'-tetrakis(3,4,5-trimethoxyphenyl)-1,2'-biimidazole, 2,2'-bis(o-chlorophenyl)-4,5,4',5'-tetraphenyl-1,2'-biimidazole, 2-benzoylnaphthalene, 4-benzoylbiphenyl, 4-benzoyldiphenyl ether, acrylated benzophenones, bis(η5-2,4-cyclopentadien-1-yl)-bis(2,6-difluoro-3-(1H-pyrrol-1-yl)phenyl)titanium, o-methylbenzoyl benzoate, p-dimethylaminobenzoic acid ethyl ester, p-dimethylaminobenzoic acid isoamylethyl ester, active tertiary amines, carbazole/phenone-based photopolymerization initiators, acridine-based photopolymerization initiators, triazine-based photopolymerization initiators, benzoyl-based photopolymerization initiators, triallylsulfoniums, hexafluorophosphate salts, triallylsulfonium hexafluorophosphates, hexafluorophosphorus aromatic-sulfonium salts, hexafluoroantimony aromatic-sulfonium salts, triallylsulfoniums, hexafluoroantimony, 4-methylphenyl [4-(2-methylpropyl)phenyl]hexafluorophosphate, 1,2-octanedione, 1 [4-(phenylthio)-2-(o-benzoyloxime)], 1-[9-ethyl-6-(2-methylbenzoyl)-9H-carbazol-3-yl]-1-(o-acetyloxime), ethyl-4-dimehylaminobenzoate, 2 ethylhexyl-4-dimethylaminobenzoate, (9-oxo-9H-xanthen-2-yl)phenyliodonium hexafluorophosphate, bis[4-n-alkyl(C10-13)phenyl]iodonium hexafluorophosphate, bis[4-n-alkyl(C10-13)phenyl]iodonium hexafluoroantimony, triphenylsulfonium trifluorosulfonate, bicyclo[2,2,1]heptane-1-methanesulfonate, (9-oxo-9H-xanthen-2-yl)phenylsulfonium hexafluorophosphate, p-azidobenzaldehyde, p-azidoacetophenone, p-azidobenzoic acid, p-azidobenzaldehyde-2-sulfonic acid Na salt, p-azidobenzalacetophenone, 4,4'-diazidochalcone, 4,4'-diazidodiphenyl sulfide, 3,3'-diazidodiphenyl sulfide, 2,6-bis(4'-azidobenzal)-4-methylcyclohexane, 1,3-bis-(4'-azidobenzal)-propanone, 4,4'-diazidochalcone-2-sulfonic acid Na salt, 4,4'-diazidostilbene-2,2'-disulfonic acid Na salt, 1,3'-bis(4'-azidobenzal)-2'-disulfonic acid Na salt-2-propanone, 2,6-bis(4'-azidobenzal)-2'-sulfonic acid (Na salt) cyclohexanone, 2,6-bis(4'-azidobenzal)-2'-sulfonic acid (Na salt) 4-methylcyclohexanone, α-cyano-4,4'-dibenzostilbene, 2,5-bis(4'-azidobenzalsulfonic acid Na salt)cyclopentanone, 3-sulfonylazidobenzoic acid, 4-sulfonylazidobenzoic acid, cinnamic acid, α-cyanocinnamylideneacetonic acid, p-azido-α-cyanocinnamic acid, p-phenylenediacrylic acid, p-phenylenediacrylic acid diethyl ester, poly(vinyl cinnamate), poly(phenoxyisopropyl cinnamylideneacetate), poly(phenoxyisopropyl α-cyanocinnamylideneacetate), naphthoquinone(1,2)diazido(2)-4-sulfonic acid Na salt, naphthoquinone(1,2)diazido(2)-5-sulfonic acid Na salt, naphthoquinone(1,2)diazido(2)-5-sulfonic acid esters (I), naphthoquinone(1,2)diazido(2)-5-sulfonic acid esters (II), naphthoquinone(1,2)diazido(2)-4-sulfonic acid salts, 2,3,4,4'-tetrahydroxybenzophenone tri(naphthoquinonediazidesulfonic acid) esters, naphthoquinone 1,2,5-(trihydroxybenzophenone) triester, 1,4-iminoquinonediazido(4)-2-sulfamide (I), 1-diazo-2,5-diethoxy-4-p-trimercaptobenzene salts, 5-nitroacenaphthene, N-acetylamino-4-nitronaphthalene, and organoboron compounds. However, the polymerization initiator is not limited to these examples. These polymerization initiators may be used alone or in combination of two or more thereof in accordance with the desired properties of the cured object.

(2) Molding

The inorganic-organic composite particles of the invention or a dispersion thereof is applicable to various molding or forming techniques. For example, in the case where the particles or the dispersion is formed into a film or sheet shape, a film is formed using an existing method such as spin coating, bar coating, spraying, or roll coating. It is also possible to directly cast the dispersion into a desired portion using a dispenser or the like.

Especially in the case where a dispersion of the inorganic-organic composite particles is subjected to forming, a drying step for removing the solvent as the dispersion medium is usually performed. For the drying, use can be made of not only room-temperature air drying in the air but also general drying techniques such as drying by heating in an oven, vacuum drying in a vacuum oven, and vacuum drying by heating. Drying may be conducted in an inert gas atmosphere especially in the case where there is a fear about stability in air.

(3) Curing Method

Methods for curing are not particularly limited. The molded object can be cured by irradiating the molded object with radiation such as ultraviolet rays or electron beams or heating the molded object. Curing by irradiation with radiation is preferred. In particular, curing by ultraviolet (UV) irradiation is suitable. In the case of curing by UV irradiation, it is preferred to use an ultraviolet lamp such as a high-pressure mercury lamp, metal halide lamp, xenon lamp, or UV-LED to irradiate the molded object at an ultraviolet-ray irradiance of 30-3,000 mW/cm$^2$ in an integrated quantity of light of 10-10,000 mJ/cm$^2$, thereby curing the molded object. The irradiation with radiation may be used in combination with infrared rays, hot air, high-frequency heating, or the like.

By regulating the irradiation conditions so as to be not less than the lower limits, dissolution of unreacted components due to curing failure can be prevented and refractive index and mechanical strength can be improved. Such regulation is hence preferred. Meanwhile, by regulating the irradiation conditions so as to be not higher than the upper limits, not only the organic components can be inhibited from being deteriorated by ultraviolet rays but also coloring, phase separation of inorganic particles, opacification or embrittlement of the cured object, etc. can be inhibited. Such regulation is hence preferred.

8-2. Polymer of Mixture of the Inorganic-Organic Composite Particles and Polymerizable Monomer and Process for Producing the Same The inorganic-organic resin composite material of the invention may contain the inorganic-organic composite particles and a resin. Since the inorganic-organic composite particles of the invention by themselves have a high refractive index and a high Abbe's number, it is possible to effectively impart these properties by compositing the particles with a resin. The compositing means a state in which the resin and the inorganic-organic composite particles have been cured in an evenly distributed state. Although methods for the compositing are not particularly limited, examples thereof include a method in which a polymerizable monomer as a starting material for resin is mixed with the inorganic-organic composite particles and the resultant mixture is cured.

Resins which may be contained are not particularly limited. However, (meth)acrylic resins, epoxy resins, silicone resins, and the like are suitable. From the standpoint of refractive index, it is suitable to use acrylic resins, for which relatively various kinds of high-refractive-index monomers are available. From the standpoints of transparency, refractive index, production efficiency, etc., (meth)acrylic resins are preferred. As starting materials for the resins, it is preferred to use polymerizable monomers.

(1) Polymerizable Monomers

Polymerizable monomers in this description are monomers which have a functional group that is capable of polymerizing by the action of radiation, e.g., ultraviolet rays or electron beams, heat, etc. Any polymerizable monomer capable of being mixed with the inorganic-organic composite particles and cured can be used without particular limitations.

Examples of the polymerizable monomers include (meth)acrylates which are starting materials for (meth)acrylic resins, epoxy compounds which are starting materials for epoxy resins, and silane compounds which are starting materials for silicone resins. Examples thereof further include reactive monomers having a functional group such as a vinyl group or a (meth)acrylamide group.

(1-1) (Meth)acrylates

Examples of the (meth)acrylates as starting materials for (meth)acrylic resins include monofunctional (meth)acrylates, bifunctional (meth)acrylates, and polyfunctional (meth)acrylates. Specifically, examples of the monofunctional (meth)acrylates include methyl (meth)acrylate, ethyl (meth)acrylate, propyl (meth)acrylate, n-butyl (meth)acrylate, isobutyl (meth)acrylate, t-butyl (meth)acrylate, pentyl (meth)acrylate, hexyl (meth)acrylate, 2-ethylhexyl (meth)acrylate, heptyl (meth)acrylate, octyl (meth)acrylate, ally (meth)acrylate, methallyl (meth)acrylate, N,N-dimethylaminoethyl (meth)acrylate, N,N-dimethylaminopropyl (meth)acrylate, N,N-diethylaminoethyl (meth)acrylate, N,N-diethylaminopropyl (meth)acrylate, polyethylene glycol monoalkyl ether (meth)acrylates, polypropylene glycol monoalkyl ether (meth)acrylates, N-vinylpyrrolidone, nonyl (meth)acrylate, phenyl (meth)acrylate, tetrahydrofurfuryl (meth)acrylate, norbornyl (meth)acrylate, phenoxy-2-methylethyl (meth)acrylate, phenoxyethoxyethyl (meth)acrylate, 3-phenoxy-2-hydroxypropyl (meth)acrylate, 2-phenylphenoxyethyl (meth)acrylate, 4-phenylphenoxyethyl (meth)acrylate, 3-(2-phenylphenyl)-2-hydroxypropyl (meth)acrylate, (meth)acrylate of an ethylene oxide-modified p-cumylphenol, decyl (meth)acrylate, 2-bromophenoxyethyl (meth)acrylate, 2,4-dibromophenoxyethyl (meth)acrylate, 2,4,6-tribromophenoxyethyl (meth)acrylate, isodecyl (meth)acrylate, dodecyl (meth)acrylate, lauryl (meth)acrylate, n-stearyl (meth)acrylate, cyclohexyl (meth)acrylate, isobornyl (meth)acrylate, tricyclodecanyl (meth)acrylate, dicyclopentenyl (meth)acrylate, adamantyl (meth)acrylate, 2-hydroxyethyl (meth)acrylate, 2-hydroxypropyl (meth)acrylate, 4-hydroxybutyl acrylate, 2-hydroxybutyl (meth)acrylate, polytetramethylene glycol mono(meth)acrylate, 2-(meth)acryloyloxyethyl-2-hydroxyethylphthalic acid glycerin monomethacrylate, 3-acryloyloxyglycerin monomethacrylate, 2-methacryloyloxyethyl-2-hydroxypropyl phthalate, hydroxyl-terminated polyester mono(meth)acrylates, phenoxyethyl (meth)acrylate, 2-phenoxy-2-hydroxypropyl (meth)acrylate, 2-hydroxy-3-phenoxypropyl (meth)acrylate, 3-chloro-2-hydroxypropyl (meth)acrylate, glycerin mono(meth)acrylate, glycidyl (meth)acrylate, polypropylene glycol mono(meth)acrylate, polyethylene glycol mono(meth)acrylate, polyethylene glycol/polypropylene glycol mono(meth)acrylate, methoxypolyethylene glycol mono(meth)acrylate, octoxypolyethylene glycol/polypropylene glycol mono(meth)acrylate, benzyl (meth)acrylate, (meth)acrylate of an ethylene oxide-modified (n=2) phenol, (meth)acrylate of a propylene oxide-modified (n=2.5) nonylphenol, 2-(meth)acryloyloxyethyl acid phosphate, diphenyl 2-methacryloyloxyethyl phosphate, mono(2-methacryloyloxyethyl) acid phosphate, mono(2-acryloyloxyethyl) acid phosphate, o-phenylphenol glycidyl ether (meth)acrylate, ally (meth)acrylate 2-acryloyloxyethyl acid phosphate monoester, (meth)acrylic acid, half (meth)acrylates of phthalic acid derivatives, such as 2-(meth)acryloyloxy-2-hydroxypropyl phthalate, monofunctional (meth)acrylates containing a fluorene framework, hydroxyethylated o-phenylphenol (meth)acrylates, furfuryl (meth)acrylate, Carbitol (meth)acrylate, butoxyethyl (meth)acrylate, monofunctional urethane (meth)acrylates, monofunctional epoxy (meth)acrylates, and monofunctional polyester (meth)acrylates.

Examples of the bifunctional (meth)acrylates include neopentyl glycol di(meth)acrylate, diethylene glycol di(meth)acrylate, 1,6-hexanediol di(meth)acrylate, tripropylene glycol di(meth)acrylate, tricyclodecanedimethanol di(meth)acrylate, 1,3-adamantanediol di(meth)acrylate, di(meth)acrylate of a bisphenol A EO (epoxy) adduct, glycerin di(meth)acrylate, neopentyl glycol hydroxypivalate di(meth)acrylate, trimethylolpropane (meth)acrylate benzoate, 2-butyl-2-ethyl-1,3-propanediol di(meth)acrylate, bifunctional urethane (meth)acrylates, bifunctional epoxy (meth)acrylates, bifunctional polyester (meth)acrylates, 9,9-bis[4-(2-acryloyloxyethoxy)phenyl]fluorene, bifunctional (meth)acrylates containing a fluorene framework, polyethylene glycol diacrylate, polypropylene glycol diacrylate, neopentyl glycol hydroxypivalate diacrylate, diacrylate of a neopentyl glycol-modified trimethylolpropane, a caprolactone-modified diacrylate of a hydroxypivalic acid neopentyl glycol ester, bisphenol A di(meth)acrylate, a (meth)acrylate of an ethylene oxide-modified bisphenol A, a (meth)acrylate of a propylene oxide-modified bisphenol A, epoxy (meth)acrylates obtained by the reaction of bisphenol A with glycidyl (meth)acrylate, epoxy (meth)acrylates obtained by the reaction of an ethylene oxide-modified bisphenol A with glycidyl (meth)acrylate, and epoxy (meth)acrylates obtained by the reaction of a propylene oxide-modified bisphenol A with glycidyl (meth)acrylate.

Examples of the polyfunctional (meth)acrylates include pentaerythritol tetra(meth)acrylate, pentaerythritol tri(meth)acrylate, dipentaerythritol hexa(meth)acrylate, dipentaerythritol penta(meth)acrylate, trimethylolpropane tri(meth)acrylate, polyfunctional urethane (meth)acrylates, polyfunctional epoxy (meth)acrylates, polyfunctional polyester (meth)acrylates, polyfunctional (meth)acrylates containing a fluorene framework, tris[2-(acryloyloxy)ethyl]isocyanurate, tris[2-(acryloyloxy)propyl]isocyanurate, 2,4,6-tris(acryloyloxyethoxy)-1,3,5-triazine, and 2,4,6-tris(acryloyloxypropoxy)-1,3,5-triazine.

These (meth)acrylates can be used alone or in combination of two or more thereof.

(1-2) Epoxy Compounds

Examples of the epoxy compounds as starting materials for epoxy resins include: novolac epoxy compounds such as bisphenol A epoxy compounds, bisphenol F epoxy compounds, phenol-novolac epoxy compounds, and cresol-novolac epoxy compounds; nitrogenous-ring epoxy compounds such as alicyclic epoxy compounds, triglycidyl isocyanurate, and hydantoin epoxy compounds; and hydrogenated bisphenol A epoxy compounds, aliphatic epoxy compounds, glycidyl ether epoxy compounds, bisphenol S epoxy compounds, biphenyl epoxy compounds, dicyclic epoxy compounds, and naphthalene epoxy compounds. These epoxy compounds can be used alone or in combination of two or more thereof.

Examples of hardeners for these epoxy resins include acid anhydride hardeners, i.e., phthalic anhydride, maleic anhydride, trimellitic anhydride, pyromellitic anhydride, hexahydrophthalic anhydride, tetrahydrophthalic anhydride, methylnadic anhydride, nadic anhydride, and glutaric anhydride. These hardeners can be used alone or in combination of two or more thereof.

(1-3) Silane Compounds

Usable as the silane compounds, which are starting materials for silicone resins, are silane compounds having a polymerizable functional group, such as dimethylsilane compounds, methylphenylsilane compounds, amino group-containing silane compounds, carboxy group-containing silane compounds, carbinol group-containing silane compounds, phenyl group-containing silane compounds, organohydrogensilane compounds, polycyclic-hydrocarbon-containing silane compounds, aromatic-hydrocarbon-containing silane compounds, and phenylsilsesquioxane. These silane compounds can be used alone or in combination of two or more thereof.

(1-4) Other Polymerizable Monomers

Besides the monomers shown above, reactive monomers having a functional group such as a vinyl group or a (meth)acrylamide group may be added.

(2) Production Process

Processes for producing the inorganic-organic resin composite material including the inorganic-organic composite particles and a resin are not particularly limited, and the composite material can be produced by the same method as described above under 8-1. Usually, a wet process is optimal. The wet process is a method in which a dispersion of the inorganic-organic composite particles is mixed with a desired polymerizable monomer and the dispersion medium is removed thereafter.

The proportion of the organic resin in the inorganic-organic resin composite material can be set at will in accordance with purposes, and is not particularly limited. However, the proportion thereof, based on the sum of the polymerizable inorganic-particle dispersant of the invention and the inorganic particles, is usually 10% by mass or higher, preferably 20% by mass or higher, more preferably 30% by mass or higher, and is usually 80% by mass or less. By regulating the proportion of the organic resin to be composited with the inorganic-organic composite particles to 10% by mass or higher, the mechanical properties of the cured object to be obtained are rendered easy to control. By regulating the proportion thereof to 80% by mass or less, the refractive-index-improving effect of the inorganic-organic composite particles can be exhibited. Namely, the amount of the polymerizable monomer to be mixed may be regulated so that the proportion of the organic resin in the inorganic-organic resin composite material is within that range. Usually, the amount thereof, based on the sum of the polymerizable inorganic-particle dispersant of the invention and the inorganic particles, is usually 10% by mass or larger, preferably 20% by mass or larger, more preferably 30% by mass or larger, and is usually 80% by mass or less.

In the case of using a dispersion medium, the total concentration of the inorganic-organic composite particles and the polymerizable monomer is usually 1-50% by mass, preferably 1-30% by mass. By regulating the concentration of the inorganic-organic composite particles so as to be not less than the lower limit, the concentration of the inorganic-organic composite particles is rendered sufficient and, even when the dispersion is used for thin-film formation, a film having a sufficient thickness is formed. Such concentrations are hence preferred. By regulating the concentration thereof so as to be not higher than the upper limit, the dispersion of the inorganic-organic composite particles is made to have better stability and be less apt to suffer gelation, etc. Such concentrations are hence preferred.

Although the composite material can be produced by the same method as described above under 8-1, the production process is roughly as follows. For obtaining the inorganic-organic resin composite material as a cured object, the polymerization initiator described above is added. Usually, the amount of the polymerization initiator, based on the solid components, other than the inorganic component, of the inorganic-organic resin composite material, is usually 0.01% by mass or larger, preferably 0.1% by mass or larger, more preferably 1% by mass or larger, and is usually 20% by mass or less, preferably 10% by mass or less, more preferably 5% by mass or less.

By using the polymerization initiator in an amount not less than the lower limit, the polymerization is prevented from resulting in a curing failure or dissolution of unreacted components, and a cured object having a sufficient refractive index and mechanical strength can be obtained. By using the polymerization initiator in an amount not larger than the upper limit, coloration or the like due to the polymerization initiator is prevented and troubles such as phase separation of inorganic particles and the opacification or embrittlement of the cured object can be inhibited.

The inorganic-organic resin composite material of the invention is applicable to various molding or forming techniques. For example, in the case of forming into a film or sheet and curing the film or sheet, use can be made of a method in which a film is formed using an existing method such as spin coating, bar coating, spraying, or roll coating and is then irradiated with ultraviolet or heat rays, electron beams, etc. to polymerize and cure the film. It is also possible to directly cast the feed material into a desired portion using a dispenser or the like and then polymerize the material by means of ultraviolet rays or the like.

Methods for the curing are not particularly limited. However, curing by ultraviolet (UV) irradiation is suitable. In the case of curing by UV irradiation, it is preferred to use an ultraviolet lamp such as a high-pressure mercury lamp, metal halide lamp, xenon lamp, or UV-LED to irradiate the molded object at an ultraviolet-ray irradiance of 30-3,000 mW/cm$^2$ in an integrated quantity of light of 10-10,000 mJ/cm$^2$, thereby curing the molded object. Such light or electron beams may be used in combination with infrared rays, hot air, high-frequency heating, or the like.

By regulating the irradiation conditions so as to be not less than the lower limits, dissolution of unreacted components due to curing failure can be prevented and a sufficient refractive index and mechanical strength are obtained. Such regulation is hence preferred. Meanwhile, by regulating the irradiation conditions so as to be not higher than the upper limits, not only the resin can be prevented from being deteriorated by ultraviolet rays but also coloring, phase separation of inorganic particles, opacification or embrittlement of the cured object, etc. are rendered less apt to occur. Such regulation is hence preferred.

8-3. Inorganic-Organic Resin Composite Material

The refractive index at room temperature (25° C.) of the inorganic-organic resin composite material, which is the cured object obtained, is preferably 1.60 or higher, more preferably 1.65 or higher, in particular 1.70 or higher. Although there is no particular upper limit on the refractive index thereof, the refractive index thereof is usually 2.0 or less. Preferably, the Abbe's number of the cured object obtained is 40 or higher when the refractive index $n_d$ is 1.60, is 35 or higher when the refractive index $n_d$ is 1.70, and is 30 or higher when the refractive index $n_d$ is 1.75.

One of the features of the inorganic-organic resin composite material of the invention resides in that the reactive index and the Abbe's number can be widely changed in a high-refractive-index range as stated above. Hitherto, it has been impossible in systems employing the same resin material to greatly change the refractive index, and it has been necessary, for changing refractive index, that two monomers differing in structure should be thermally polymerized over a long period. Even when a material system obtained using such thermal polymerization is composited with inorganic particles, not only the time period required for the polymerization cannot be shortened but also a high Abbe's number cannot be imparted. In addition, since the polymerization is thermal polymerization, the conventional technique is unsuitable for microprocessing.

In contrast, the inorganic-organic resin composite material, which includes the inorganic-organic composite particles of the invention, not only is obtained through short-period photopolymerization but also is suitable, for example, for designing lenses in which materials having various optical properties are used in combination to configure one optical system or designing a multilayer film for which control of refractive index is necessary. Furthermore, for example, in applications involving information transfer between semiconductor chips which necessitates an optical circuit having a large radius of curvature, the high refractive index and the high Abbe's number make it possible to reduce the loss in the bent portion due to light scattering. The composite material of the invention is hence suitable for such applications.

Furthermore, the inorganic-organic resin composite material of the invention has a feature wherein the temperature dependence of the optical properties is low. Specifically, the refractive index at 60° C. of the inorganic-organic resin composite material of the invention is 1.60 or higher, preferably 1.65 or higher, more preferably 1.70 or higher. Although there is no particular upper limit on the 60° C. refractive index thereof, the refractive index thereof at 60° C. is usually 2.0 or less. Preferably, the Abbe's number at 60° C. of the inorganic-organic resin composite material is 40 or higher when the refractive index $n_d$ is 1.60, is 35 or higher when the refractive index $n_d$ is 1.65, and is 30 or higher when the refractive index $n_d$ is 1.70.

The temperature dependence of the refractive index of the inorganic-organic resin composite material of the invention is usually $1.0 \times 10^{-3}$ or less, preferably $3.0 \times 10^{-4}$ or less, more preferably, $2.5 \times 10^{-4}$ or less, even more preferably $2.4 \times 10^{-4}$ or less. The temperature dependence of the Abbe's number of the inorganic-organic resin composite material is usually $1.0 \times 10^{-1}$ or less, preferably $9.0 \times 10^{-2}$ or less, more preferably $8.0 \times 10^{-2}$ or less.

Although portable electronic appliances, including smartphones, automotive electrical components, etc. considerably change in temperature depending on the surrounding environment, changes in refractive index with changing temperature result in changes in the speed of the light which is transmitted through the optical circuits. There is hence the possibility of posing a problem, for example, that the information processing speed changes with changing temperature. Consequently, from the standpoint of preventing the speed from thus changing with changing temperature, it is preferred that the changes in refractive index with changing temperature should be as small as possible. With respect to Abbe's number also, it is preferred that the light transmitted through a medium should not change in speed with changing wavelength, in view of, for example, the case where light components having multiple wavelengths are simultaneously transmitted through the same optical circuit. Consequently, the higher the Abbe's number, which is an index to refractive-index change due to wavelength, the better the medium. Namely, the inorganic-organic resin composite material of the invention is especially suitable for use in such applications where a low temperature dependence of optical properties is required, such as optical waveguides and optical circuits.

9. Applications

The inorganic-organic resin composite material of the invention has a high refractive index and a high Abbe's number even when the proportion of the inorganic-organic composite particles to the inorganic-organic resin composite material is small. Consequently, by changing the addition amount of the inorganic-organic composite particles, this composite material is rendered suitable for use in applications in which control of refractive index and control of Abbe's number over wide ranges are required, such as optical members in which the whole visible-light region is used, lens applications in which various optical properties are combined to design one optical system, and film applications. In particular, this composite material is optimal as various optical members which have high transparency in a wide wavelength range and are required to have a high refractive index and a high Abbe's number, so as to reflect the feature of the inorganic-organic composite particles of the invention. Furthermore, the composite material is especially suitable as optical members in which those optical properties are required to have a low temperature dependence.

Namely, the composite material is optimal for use as functional films for forward scattering, reflection, light condensation, etc. which are used in the image display portions of flat panel displays (FPD) such as liquid-crystal displays (LCD), plasma display panels (PDP), electroluminescence displays (EL), or surface-conduction electron-emission displays (SED). Moreover, the composite material is applicable to light transmission members such as optical waveguides, optical circuits, optical fibers, lightguide sheets, microarray lens sheets, prism sheets, Fresnel lenses, and lenticular lenses, and to lens sheets, diffusion films, holographic substrates, light modulation films, etc.

EXAMPLES

The invention will be explained below in detail by reference to Examples and Comparative Examples, but the invention should not be construed as being limited by the following Examples.

In the following Examples and Comparative Examples, measurements were made by the following methods.

Refractive Index

A reflective spectral film thickness meter ("FE-3000", manufactured by Otsuka Electronics Co., Ltd.) was used to determine a spectrum of absolute reflectance in the range of 330-1,000 nm by means of the n-Cauchy dispersion formula, as a representative approximate expression of the wavelength dispersion of refractive index. A spectrum of refractive index was determined by the nonlinear least square method to obtain the refractive indexes for light components having wavelengths of 486 nm (F-line), 587 nm (d-line), and 656 nm (C-line). The measurement was made at a measuring temperature of 25° C.

Temperature Dependence of Refractive Index

Prism coupler Model 2010, manufactured by Metricon Corp., to which a hot stage had been fitted was used to measure the refractive index for 633-nm light. The measurement was made at measuring temperatures ranging from 30° C. to 80° C. to determine the change in refractive index per ° C. during temperature rising from 30° C. to 80° C. These measuring temperatures each were the temperature of the prism in contact with the sample; the measurement of refractive index was made after the system was allowed to stand for a sufficient period (10 minutes or longer) until the prism temperature became equal to the sample temperature.

Abbe's Number ($v_d$)

A reflective spectral film thickness meter ("FE-3000", manufactured by Otsuka Electronics Co., Ltd.) was used to determine a spectrum of absolute reflectance in the range of 330-1,000 nm by means of the n-Cauchy dispersion formula, as a representative approximate expression of the wavelength dispersion of refractive index. A spectrum of refractive index was determined by the nonlinear least square method to obtain the refractive indexes for light components having wavelengths of 486 nm (F-line), 587 nm (d-line), and 656 nm (C-line). Furthermore, the Abbe's number was calculated using the following equation. The measurement was made at a temperature of 25° C.

$$\text{Abbe's number}(v_d) = (n_d - 1)/(n_F - n_C)$$

(In the equation, $n_d$ represents refractive index for light having a wavelength of 587 nm, $n_F$ represents refractive index for light having a wavelength of 486 nm, and $n_C$ represents refractive index for light having a wavelength of 656 nm.)

Temperature Dependence of Abbe's Number ($v_d$)

The value of Abbe's number ($v_d$) measured at 25° C. was used. With respect to 80° C. also, the Abbe's number was calculated in the same manner. The temperature dependence of Abbe's number was determined by determining the change in Abbe's number per ° C. over the range of 25° C. to 80° C. For the measurement, a reflective spectral film thickness meter ("FE-3000", manufactured by Otsuka Electronics Co., Ltd.) was used. A heater was disposed under the test sample and an aluminum plate having a thickness of 5 mm was interposed between the sample and the heater, thereby causing the heat from the heater to be evenly applied to the sample when the measurement was conducted. The sample temperature measured with a non-contact type thermometer was taken as the measuring temperature.

The dispersion stability of a dispersion or the like was evaluated by visually examining the dispersion or the like for transparency.

[Synthesis of Inorganic Particles]

As inorganic particles for use in forming inorganic-organic composite particles, zirconium oxide nanoparticles were synthesized by the following method.

Into a 1-L three-necked flask was introduced 500 mL of benzyl alcohol (oxygen-containing organic solvent). Nitrogen bubbling was conducted for 30 minutes. While continuing the nitrogen bubbling, 116.7 g of a 1-propanol solution containing 70% by mass zirconium propoxide (number of moles of the zirconium propoxide (metal oxide precursor)=0.25 mol) was added thereto, and the mixture was stirred for 30 minutes. Thereto was added 100.3 g (0.375 mol) of oleylamine. The mixture was stirred for further 30 minutes. The solution prepared (reaction liquid) was subjected to 3-hour nitrogen bubbling, enclosed in a sealed container made of stainless steel, and heated at 200° C. for 48 hours.

A 50 g portion of the resultant reaction liquid in a milkwhite slurry state was taken out, and a large excess of ethanol was added thereto to form a precipitate. This mixture was centrifuged to recover the precipitate. This precipitate was washed six times with an ethanol/hexane mixed solvent and then recovered and dried to obtain zirconium oxide in a white powder state (yield, 80%).

The zirconium oxide obtained was examined for crystallinity and primary particle diameter by X-ray diffractometry (PW1700, manufactured by PANalytical (previous name, Phillips), Holland; X-ray output (CuKα), 40 Kv, 30 mA; scanning axis, θ/2θ; scanning range (2θ), 10.0-80.0°; measuring mode, continuous; reading width, 0.05°; scanning speed, 3.0°/min; slit DS, 1°; SS, 1°; RS, 0.2 mm) and with a transmission electron microscope.

The crystallite diameter was calculated from the half-value width of the peak attributable to the (111) plane and appearing at around 2θ=30 in the X-ray diffractometry, using the Scherrer equation (D=K·λ/β·cos θ; half-value width correction formula $\beta = (\beta_o^2 - i^2)^{1/2}$, wherein K=0.9 and λ=1.54056 Å; the Bragg angle (θ) attributable to CuKα1 line and the half-value width (βo) attributable to CuKα1 line were calculated by the profile fitting method using JADE5.0+, manufactured by MDI. The half-value width (β) attributable to CuKα1 line due to the sample was determined by calculating βi from a regression curve for the diffraction angle (2θ) attributable to CuKα1 line determined beforehand by means of standard Si and for the half-value width attributable to CuKα1 line due to the apparatus.).

As a result, the zirconium oxide obtained was found to have a crystallite diameter of 3-4 nm. As a result of the examination with a transmission electron microscope, the particles yielded were found to each have a particle diameter in the range of 1-10 nm.

[Synthesis of Polymerizable Inorganic-Particle Dispersants]

Example 1

Synthesis of 2-(carboxymethylthiomethyl)-5-(methacryloylthiomethyl)-1,4-dithiane 2-(Carboxymethylthiomethyl)-5-(methacryloylthiomethyl)-1,4-dithiane (hereinafter referred to as "MDC") was synthesized as a polymerizable inorganic-particle dispersant by the following method.

[Chem. 52]

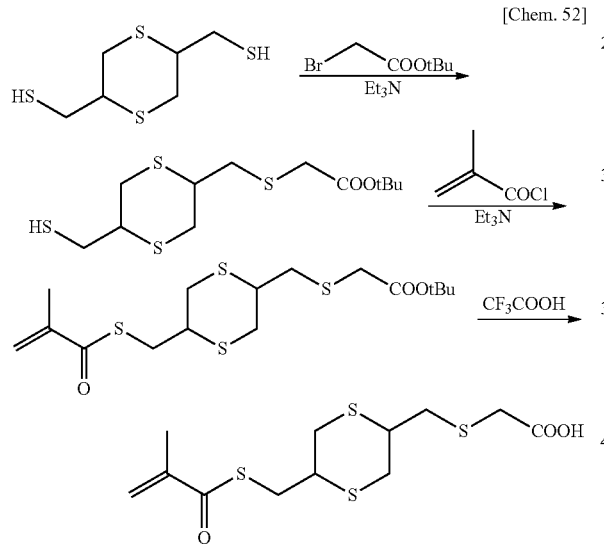

In a nitrogen atmosphere, 32.4 g (153 mmol) of 2,5-bis(mercaptomethyl)-1,4-dithiane synthesized by a known method (e.g., the method described in Japanese Patent No. 2895987), 30.8 g (305 mmol) of triethylamine, and 600 mL of dichloromethane were introduced into a 1-L three-necked flask equipped with a dropping funnel, and the contents were stirred at room temperature. Thereto was added dropwise 29.7 g (153 mmol) of tert-butyl bromoacetate over 1 hour. Thereafter, the resultant mixture was stirred at that temperature overnight.

Water was added thereto, and the organic layer was separated. The organic layer was washed with saturated aqueous sodium chloride solution and then dehydrated with anhydrous sodium sulfate. The insoluble matter was filtered off, and the resultant filtrate was concentrated to obtain an oily substance. This oily substance was purified by silica gel column chromatography (n-heptane/ethyl acetate=9/1 by volume) to obtain 24.5 g (75.0 mmol) of 2-(tert-butyloxycarbonylmethylthiomethyl)-5-mercaptomethyl)-1,4-dithiane as a colorless oily substance.

In a nitrogen atmosphere, 24.5 g (75.0 mmol) of the 2-(tert-butyloxycarbonylmethylthiomethyl)-5-mercaptomethyl)-1,4-dithiane obtained above, 8.3 g (82 mmol) of triethylamine, 100 mg of p-methoxyphenol, and 600 mL of dichloromethane were introduced into a 1-L three-necked flask equipped with a dropping funnel, and the contents were stirred at room temperature.

Thereto was added dropwise 8.5 g (82 mmol) of methacryloyl chloride over 1 hour. Thereafter, the resultant mixture was stirred at that temperature for 3 hours. Water was added thereto, and the organic layer was separated. The organic layer was washed with saturated aqueous sodium chloride solution and then dehydrated with anhydrous sodium sulfate. The insoluble matter was filtered off, and the resultant filtrate was concentrated to obtain an oily substance. This oily substance was purified by silica gel column chromatography (n-heptane/ethyl acetate=4/1 by volume) to obtain 25.5 g (64.6 mmol) of 2-(tert-butyloxycarbonylmethylthiomethyl)-5-(methacryloylthiomethyl)-1,4-dithiane as a colorless oily substance.

In a nitrogen atmosphere, 10 g (25 mmol) of the 2-(tert-butyloxycarbonylmethylthiomethyl)-5-(methacryloylthiomethyl)-1,4-dithiane obtained above, 20 mg of copper(II) chloride, 200 mL of dichloromethane, and 50 g of trifluoroacetic acid were introduced into a 500-mL three-necked flask equipped with a dropping funnel, and the contents were stirred at room temperature. After 2.5 hours, 50 g of trifluoroacetic acid was additionally added, and the resultant mixture was stirred for further 4 hours. Thereafter, water and ethyl acetate were added thereto, and the organic layer was separated. The organic layer was washed with saturated aqueous sodium chloride solution, subsequently dehydrated with anhydrous sodium sulfate, and concentrated to obtain 7.14 g (21.1 mmol) of 2-(carboxymethylthiomethyl)-5-(methacryloylthiomethyl)-1,4-dithiane as a white solid.

IR (KBr, cm$^{-1}$):
Apparatus: FT/IR-6100 type A (JASCO)
Detector: TGS
Measuring technique: liquid film method
Resolution: 4 cm$^{-1}$
Number of integrations: 32
3,500-3,100 cm$^{-1}$ (OH stretching),
2,900-2,952 cm$^{-1}$ (CH stretching),
1,713, 1,693 cm$^{-1}$ (CO stretching)
$^1$H-NMR (300 MHz):
Apparatus: JNM-AL300, manufactured by JEOL
Solvent: CDCl$_3$
Internal reference: TMS
δ [ppm]: 6.11 (1H, s), 5.63 (1H, s), 3.30-2.70 (12H, m), 1.98 (3H, s)
MS (API-ES, negative):
Apparatus: Water LCT Premier XE
Ionization method: flow injection ESI(−) method
Solvent for measurement: methanol
Carboxylic monoester 337 [M-H]$^-$ 675 [2M-H]$^-$ Example 2

Synthesis of Mixture of bis[2-(5-methacryloylthiomethyl-1,4-dithianyl-2-methylthio)ethyl]phosphoric acid ester and [2-(5-methacryloylthiomethyl-1,4-dithianyl-2-methylthio)ethyl]phosphoric acid ester A mixture of bis[2-(5-methacryloylthiomethyl-1,4-dithianyl-2-methylthio)ethyl]phosphoric acid ester and [2-(5-methacryloylthiomethyl-1,4-dithianyl-2-methylthio)ethyl]phosphoric acid ester (hereinafter, the mixture is referred to as "MDEP") was synthesized as a polymerizable inorganic-particle dispersant by the following method.

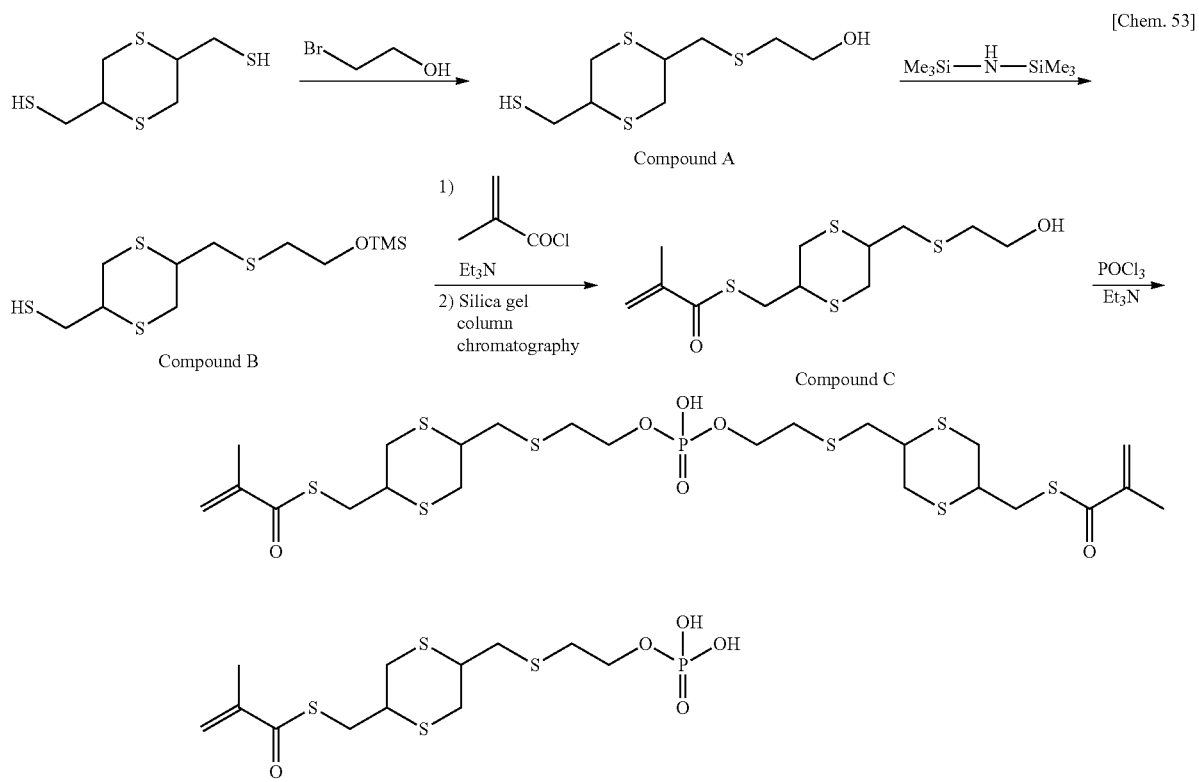

In a nitrogen atmosphere, 370 mL of degassed ethanol and 19.5 g (174 mmol) of KOH were introduced into a 1-L three-necked flask equipped with a dropping funnel, and the KOH was dissolved at room temperature. Thereto was added 37.0 g (174 mmol) of 2,5-bis(mercaptomethyl)-1,4-dithiane synthesized by a known method (e.g., the method described in U.S. Pat. No. 2,895,987). This compound was dissolved at that temperature.

The reaction liquid was cooled with ice, and 21.7 g (174 mmol) of 2-bromoethanol was added dropwise thereto over 15 minutes. This mixture was stirred with cooling with ice for 1 hour and then at an elevated temperature of room temperature for 1 hour, and was thereafter returned to the ice-cooled state. Subsequently, the pH of this mixture was adjusted to 1 with 2-N hydrochloric acid. The ethanol was distilled off under reduced pressure, and the residue was extracted with ethyl acetate. The extract was concentrated, and the oily substance obtained was purified by silica gel column chromatography (n-heptane/ethyl acetate)=1/1 by volume) to obtain 21.0 g (81.9 mmol) of a 2-hydroxyethylated product (compound A) as a colorless oily substance (yield, 47%).

In a nitrogen atmosphere, 210 mL of dichloromethane and 21.0 g of compound A obtained above were introduced into a 500-mL three-necked flask equipped with a dropping funnel, and the compound A was dissolved. Thereto was added 9.4 g (58.2 mmol) of 1,1,1,3,3,3-hexamethyldisilazane (TMS). The resultant mixture was reacted at room temperature for 9 hours to obtain a TMS-modified compound (compound B). To the resultant reaction liquid was added 53 mg of 4-methoxyphenol. After the 4-methoxyphenol was dissolved, this mixture was cooled with ice, and 9.1 g (89.9 mmol) of triethylamine was added thereto.

While the mixture was kept being cooled with ice, 8.56 g (81.9 mmol) of methacryloyl chloride was added dropwise thereto over 30 minutes. Thereafter, the resultant mixture was reacted with cooling with ice for 1 hour and then at an elevated temperature of room temperature for 1 hour. After the mixture was returned to the ice-cooled state, water was added thereto. The resultant mixture was subjected to liquid separation and concentration, and the oily substance obtained was purified by silica gel column chromatography (n-heptane/ethyl acetate=6/4 by volume) to obtain 17.5 g (53.9 mmol) of a methacryloyl-containing product (compound C) as a colorless oily substance (yield, 66%).

In a nitrogen atmosphere, 20 mL of dichloromethane and 1.08 g (7.04 mmol) of phosphorus oxychloride were introduced into a 100-mL three-necked flask equipped with a dropping funnel, and this flask was cooled with ice. A mixed solution of 4.64 g (14.3 mmol) of compound C obtained above and 1.45 g (14.3 mmol) of triethylamine in 15 mL of dichloromethane was added dropwise thereto through the dropping funnel over 30 minutes while maintaining the cooling with ice. After this mixture was stirred for 1 hour with cooling with ice, 0.73 g (7.2 mmol) of triethylamine was added thereto and the resultant mixture was reacted at that temperature for 4 hours. Ice was added thereto, and this mixture was stirred for 10 hours and then subjected to liquid separation. The organic layer was washed with 0.1-N hydrochloric acid prepared with saturated aqueous sodium chloride solution, dried with anhydrous magnesium sulfate, and concentrated, thereby obtaining 4.5 g of a colorless oily substance.

Through $^1$H-NMR and LC/MS, this oily substance was ascertained to be a mixture of the desired compounds, i.e., bis[2-(5-methacryloylthiomethyl-1,4-dithianyl-2-methylthio)ethyl]phosphoric acid ester and [2-(5-methacryloylthiomethyl-1,4-dithianyl-2-methylthio)ethyl]phosphoric acid ester. HPLC revealed that this mixture had a purity of 73% and had such a phosphoric acid ester mixing ratio that the phosphoric diester/phosphoric monoester ratio was 1/2.

Conditions for the analysis by HPLC are as follows.
Column: Inertsil ODS-3V, 5 μm, 150 mm×4.6 mm I.D. (manufactured by GL Sciences Inc.)
Column oven temperature: 40° C.
Eluent: 0.1% by volume aqueous phosphoric acid solution/acetonitrile=30/70 (by volume)
Flow rate: 1 mL/min
Detector: UV 210 nm
IR (KBr, cm$^{-1}$):
Apparatus: NEXUS 670 and Nic-Plan, manufactured by Thermo Fisher Scientific
Purge: $N_2$
Measuring technique: microreflection method
Resolution: 4 cm$^{-1}$
Number of integrations: 128
3,500-3,100 cm$^{-1}$ (OH stretching),
2,952, 2,909 cm$^{-1}$ (CH stretching),
1,659 cm$^{-1}$ (CO stretching),
1,283, 1,027, 893 cm$^{-1}$ (PO stretching, CO stretching, P—O—C alkyl stretching)
$^1$H-NMR (400 MHz):
Apparatus: AVANCE 400, manufactured by BRUKER
Solvent: $CDCl_3$
Internal reference: TMS
δ [ppm]: 6.10 (1H), 5.63 (1H), 3.65-3.63 (2H), 3.33-3.32 (2H), 3.15-2.70 (10H), 1.98 (3H)
MS (API-ES, negative):
Apparatus: Water LCT Premier XE
Ionization method: flow injection ESI(−) method
Solvent for measurement: methanol
Phosphoric monoester 403 [M-H]$^-$, 807 [2M-H]$^-$
Phosphoric diester 710 [M-H]$^-$ Evaluation of Refractive Indexes and Abbe's Numbers of Polymerizable Inorganic-Particle Dispersants Example 3

MDC

A 0.196 g portion of the MDC synthesized in Example 1 was weighed out and placed in a 10-mL sample bottle made of glass, and was dissolved in 7.784 g of tetrahydrofuran (THF) at room temperature to produce a dispersion having a concentration of 2.5% by weight. 1-Hydroxycyclohexyl phenyl ketone (Luna 200, manufactured by Nihon Siberhegner K.K.) was added thereto as a polymerization initiator in an amount of 10% by mass based on the MDC and dissolved therein.

The solution produced was applied to a glass substrate using a spin coater (manufactured by MIKASA) (rotation speed, 1,000 rpm; period, 20 seconds) and dried to form a thin film. Thereafter, in an oxygen-free environment, the thin film was irradiated with ultraviolet rays using a high-pressure mercury lamp (manufactured by Eye Graphics Co., Ltd.) at an irradiance of 100 mW/cm$^2$ in an integrated quantity of light of 350 mJ/cm$^2$. Thus, a cured film (thickness, 280 nm) of the polymerizable inorganic-particle dispersant MDC alone was produced.

The cured film obtained was examined for refractive index and Abbe's number in accordance with the methods described above. The results thereof are shown in Table 1. In Table 1 is also shown the dispersion stability of the MDC in THF.

Example 4

Refractive Indexes and Abbe's Number of MDEP

A weighed amount of the MDEP obtained in Example 2 was placed in a 10-mL sample bottle made of glass, and was dissolved in 4 mL of tetrahydrofuran at room temperature to produce a dispersion having a concentration of 10% by mass. 1-Hydroxycyclohexyl phenyl ketone (Luna 200, manufactured by Nihon Siberhegner K.K.) was added thereto as a polymerization initiator in an amount of 5% by mass based on the MDEP and dissolved therein.

The solution produced was applied to a glass substrate using a spin coater (manufactured by MIKASA Co., Ltd.) (rotation speed, 1,000 rpm; period, 20 seconds) and dried to form a thin film. Thereafter, in an oxygen-free environment, the thin film was irradiated with ultraviolet rays using a high-pressure mercury lamp (manufactured by Eye Graphics Co., Ltd.) at an irradiance of 100 mW/cm$^2$ in an integrated quantity of light of 350 mJ/cm$^2$. Thus, a cured film (thickness, 400 nm) of the polymerizable inorganic-particle dispersant MDEP alone was produced. The cured film obtained was examined for refractive index and Abbe's number in accordance with the methods described above. The results thereof are shown in Table 1. In Table 1 is also shown the dispersion stability of the MDEP in THF.

Comparative Example 1

Refractive Indexes and Abbe's Number of Polymerizable Inorganic-Particle Dispersant Containing Aromatic Ring in Q The following compound α was produced by the method shown in the Synthesis Example 3 given in JP-A-2006-273709.
Compound α

[Chem. 54]

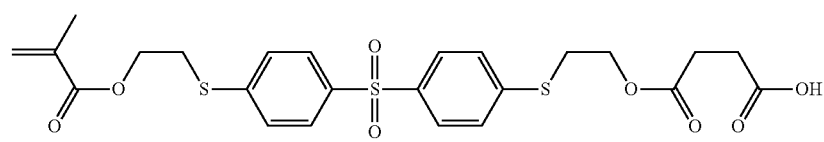

A cured film of a polymerizable inorganic-particle dispersant alone was produced in the same manner as in Example 3, except that the polymerizable inorganic-particle dispersant was changed from the MDC synthesized in Example 1 to the compound α obtained by the method shown above. This cured film was examined for refractive index and Abbe's number in the same manners. The results thereof are shown in Table 1 together with the dispersion stability.

Comparative Example 2

Refractive Indexes and Abbe's Number of Polymerizable Inorganic-Particle Dispersant Containing no Sulfur Atom in Q (2-methacryloyloxyethyl acid phosphate)

A cured film of a polymerizable inorganic-particle dispersant alone was produced in the same manner as in Example 3, except that the polymerizable inorganic-particle dispersant was changed from the MDC synthesized in Example 1 to 2-methacryloyloxyethyl acid phosphate (Light Ester P-2M, manufactured by Kyoeisha Chemical Co., Ltd.). This cured film was examined for refractive index and Abbe's number in the same manners. The results thereof are shown in Table 1 together with the dispersion stability.

Comparative Example 3

Refractive Indexes and Abbe's Number of Polymerizable Inorganic-Particle Dispersant Containing No Sulfur Atom in Q (2-methacryloyloxyethyl acid phosphate)

A cured film of a polymerizable inorganic-particle dispersant alone was produced in the same manner as in Comparative Example 1, except that the polymerizable inorganic-particle dispersant was replaced with 2-methacryloyloxyethylphthalate (CB-1, manufactured by Shin-Nakamura Chemical Co., Ltd.). This cured film was examined for refractive index and Abbe's number in the same manners. The results thereof are shown in Table 1 together with the dispersion stability.

TABLE 1

[Evaluation of temperature dependence of refractive index and Abbe's number of polymerizable inorganic-particle dispersants]

|  | Kind of dispersant | Refractive index 587 nm | Refractive index 486 nm | Refractive index 656 nm | Abbe's number ($v_d$) |
|---|---|---|---|---|---|
| Example 3 | MDC | 1.6273 | 1.6373 | 1.6243 | 48 |
| Example 4 | MDEP | 1.6260 | 1.6360 | 1.6220 | 45 |
| Comparative Example 1 | compound α | 1.6288 | 1.6495 | 1.6215 | 22 |
| Comparative Example 2 | P-2M | 1.4780 | 1.4860 | 1.4750 | 43 |
| Comparative Example 3 | CB-1 | 1.5320 | 1.5410 | 1.5290 | 44 |

Example 5

MDC

A cured film obtained in the same manner as in Example 3 was used and examined for the temperature dependence of Abbe's number by the method described above. For the measurement of refractive index, use was made of a solution obtained by producing a 6.0% by mass MDC dispersion in which tetrahydrofuran (THF) was used as a solvent, adding 1-hydroxycyclohexyl phenyl ketone (Luna 200, manufactured by Nihon Siberhegner K.K.) thereto as a polymerization initiator in an amount of 10% by mass based on the MDC, and dissolving the polymerization initiator. The solution produced was applied to a glass substrate using a spin coater (manufactured by MIKASA) (rotation speed, 500 rpm; period, 20 seconds) and dried to form a thin film. Thereafter, in an oxygen-free environment, the thin film was irradiated with ultraviolet rays using a high-pressure mercury lamp (manufactured by Eye Graphics Co., Ltd.) at an irradiance of 100 mW/cm² in an integrated quantity of light of 350 mJ/cm². Thus, a cured film (thickness, 430 nm) of the polymerizable inorganic-particle dispersant MDC alone was produced. The thin film was examined for refractive index by the method described above. The results thereof are shown in Table 2.

Comparative Example 4

Compound α

A cured film of a polymerizable inorganic-particle dispersant alone was produced in the same manner as in Example 5, except that the polymerizable inorganic-particle dispersant was replaced with compound α. The cured film was examined for the temperature dependence of refractive index and Abbe's number in the same manner by the method described above. The results thereof are shown in Table 2.

TABLE 2

|  | Kind of dispersant | Refractive index $n_d$ (633 nm, 30° C.) | Abbe's number $v_d$ (25° C.) | Temperature dependence of Abbe's number $\Delta v_d/°$ C. | Temperature dependence of refractive index $\Delta n_d /°$ C. (633 nm) |
|---|---|---|---|---|---|
| Example 5 | MDC | 1.6387 | 48 | $5.50 \times 10^{-2}$ | $2.20 \times 10^{-4}$ |
| Comparative Example 4 | compound α | 1.6210 | 22 | $1.13 \times 10^{-1}$ | $2.50 \times 10^{-4}$ |

It can be seen from the evaluation results shown above that the polymerizable inorganic-particle dispersants of the invention are high in refractive index and Abbe's number, in particular, in the temperature dependence thereof, as compared with the polymerizable inorganic-particle dispersants containing an aromatic ring.

Production and Evaluation of Inorganic-Organic Resin Composite Materials

Example 6

MDC

A 0.7997 g portion of the MDC produced in Example 1 was added to and mixed with a dispersion obtained by suspending 0.2 g of the zirconium oxide synthesized by the method described above (the zirconium oxide amount being 20% by mass based on the MDC) in 32.3 g of tetrahydrofuran. Thus, a dispersion having a solid concentration of 3% by mass was produced.

1-Hydroxycyclohexyl phenyl ketone (Luna 200, manufactured by Nihon Siberhegner K.K.) was added thereto as a polymerization initiator in an amount of 10% by mass based on the MDC and dissolved therein. The solution produced (The dispersion stability of this solution is shown in Table 3.) was applied to a glass substrate using a spin coater (manufactured by MIKASA Co., Ltd.) (rotation speed, 1,000 rpm; period, 20 seconds) and dried to form a thin film. Thereafter, in an oxygen-free environment, the thin film was irradiated with ultraviolet rays using a high-pressure mercury lamp (manufactured by Eye Graphics Co., Ltd.) at an irradiance of 100 mW/cm² in an integrated quantity of light of 350 mJ/cm². Thus, a cured film (thickness, 210 µm) of the inorganic-organic composite particles was produced. This cured film was examined for refractive index and Abbe's number in accordance with the methods described above. The results thereof are shown in Table 3.

Example 7

MDC

A cured film was obtained in the same manner as in Example 6, except that the use amount of the zirconium oxide based on the MDC in Example 6 was changed to 40% by mass. The cured film was examined for refractive index and Abbe's number in the same manners. The results thereof are shown in Table 3.

Example 8

MDC

A cured film was obtained in the same manner as in Example 6, except that the use amount of the zirconium oxide based on the MDC in Example 6 was changed to 60% by mass. The cured film was examined for refractive index and Abbe's number in the same manners. The results thereof are shown in Table 3.

Production and Evaluation of Inorganic-Organic Resin Composite Materials

Example 9

MDEP

A 0.25 g portion of the MDEP produced in Example 2 was added to and mixed with a dispersion obtained by suspending 0.06 g of the zirconium oxide synthesized by the method described above (the zirconium oxide amount being 20% by mass based on the MDEP) in 3 mL of tetrahydrofuran. Thus, a dispersion having a solid concentration of 10% by mass was produced. 1-Hydroxycyclohexyl phenyl ketone (Luna 200, manufactured by Nihon Siberhegner K.K.) was added thereto as a polymerization initiator in an amount of 5% by mass based on the MDEP and dissolved therein.

The solution produced (The dispersion stability of this solution is shown in Table 1.) was applied to a glass substrate using a spin coater (manufactured by MIKASA Co., Ltd.) (rotation speed, 1,000 rpm; period, 20 seconds) and dried to form a thin film. Thereafter, in an oxygen-free environment, the thin film was irradiated with ultraviolet rays using a high-pressure mercury lamp (manufactured by Eye Graphics Co., Ltd.) at an irradiance of 100 mW/cm² in an integrated quantity of light of 350 mJ/cm². Thus, a cured film (thickness, 340 µm) of the inorganic-organic composite particles was produced. This cured film was examined for refractive index and Abbe's number in accordance with the methods described above. The results thereof are shown in Table 3.

Example 10

A cured film was obtained in the same manner as in Example 9, except that the use amount of the zirconium oxide based on the MDEP was changed to 40% by mass. The cured film was examined for refractive index and Abbe's number in the same manners. The results thereof are shown in Table 3.

Example 11

A cured film was obtained in the same manner as in Example 9, except that the use amount of the zirconium oxide based on the MDEP was changed to 60% by mass. The cured film was examined for refractive index and Abbe's number in the same manners. The results thereof are shown in Table 3.

Example 12

A cured film was obtained in the same manner as in Example 9, except that the use amount of the zirconium oxide based on the MDEP was changed to 70% by mass. The cured film was examined for refractive index and Abbe's number in the same manners. The results thereof are shown in Table 3.

Comparative Example 5

A cured film of a polymerizable inorganic-particle dispersant alone was produced in the same manner as in Comparative Example 1, except that the polymerizable inorganic-particle dispersant was replaced with 2-methacryloyloxyethylphthalate (CB-1, manufactured by Shin-Nakamura Chemical Co., Ltd.). This cured film was examined for refractive index and Abbe's number in the same manners. The results thereof are shown in Table 3 together with the dispersion stability.

Comparative Example 6

A cured film of inorganic-organic composite particles was produced in the same manner as in Comparative Example 2 except that the polymerizable inorganic-particle dispersant was replaced with 2-methacryloyloxyethylphthalate (CB-1, manufactured by Shin-Nakamura Chemical Co., Ltd.). This cured film was examined for refractive index and Abbe's number in the same manners. The results thereof are shown in Table 3 together with the dispersion stability.

TABLE 3

| | Kind of dispersant | $ZrO_2$* (mass %) | Stability of dispersant (THF solution) | Refractive index 587 nm | 486 nm | 656 nm | Abbe's number ($\nu_d$) |
|---|---|---|---|---|---|---|---|
| Example 3 | MDC | 0 | translucent to transparent | 1.6273 | 1.6373 | 1.6243 | 48 |
| Example 6 | MDC | 20 | translucent to transparent | 1.6534 | 1.6638 | 1.6501 | 48 |

TABLE 3-continued

| | Kind of dispersant | ZrO$_2$* (mass %) | Stability of dispersant (THF solution) | Refractive index 587 nm | 486 nm | 656 nm | Abbe's number ($v_d$) |
|---|---|---|---|---|---|---|---|
| Example 7 | MDC | 40 | transparent | 1.6955 | 1.7091 | 1.6911 | 39 |
| Example 8 | MDC | 60 | transparent | 1.7412 | 1.7576 | 1.7359 | 34 |
| Example 4 | MDEP | 0 | transparent | 1.6260 | 1.6360 | 1.6220 | 45 |
| Example 9 | MDEP | 20 | transparent | 1.6590 | 1.6680 | 1.6530 | 44 |
| Example 10 | MDEP | 40 | transparent | 1.6820 | 1.6920 | 1.6800 | 57 |
| Example 11 | MDEP | 60 | transparent | 1.7010 | 1.7110 | 1.6980 | 54 |
| Example 12 | MDEP | 70 | transparent | 1.7370 | 1.7500 | 1.7320 | 41 |
| Comparative Example 2 | P-2M | 0 | transparent | 1.4780 | 1.4860 | 1.4750 | 43 |
| Comparative Example 5 | P-2M | 60 | transparent | 1.6490 | 1.6600 | 1.6450 | 43 |
| Comparative Example 3 | CB-1 | 0 | transparent | 1.5320 | 1.5410 | 1.5290 | 44 |
| Comparative Example 6 | CB-1 | 60 | transparent | 1.6840 | 1.6980 | 1.6780 | 34 |

The results given above showed the following. It was understood from Examples 3 and 4 that the polymerizable inorganic-particle dispersants MDC and MDEP produced in Examples 1 and 2, even when used alone, give cured objects which are highly transparent and have a refractive index of 1.62 or higher and an Abbe's number of 40 or higher.

Furthermore, it was understood from Examples 6 to 8 and Examples 9 to 12 that although the conventional dispersants require an inorganic-particle concentration of 60% or higher for attaining a refractive index of 1.65 or higher, a high refractive index and a high Abbe's number can be attained even with an inorganic-particle concentration as low as 20% by mass by compositing the dispersants of the invention (MDC and MDEP) with inorganic particles.

It was also understood that the adsorbable portions of the polymerizable inorganic-particle dispersants produce the effect of dispersing so as to result in transparency and are capable of further elevating the concentration of inorganic particles to thereby attain both an improvement in refractive index which has not been made so far and retention of a high Abbe's number in wide ranges.

While the invention has been described in detail and with reference to specific embodiments thereof, it will be apparent to one skilled in the art that various changes and modifications can be made therein without departing from the spirit and scope thereof. This application is based on a Japanese patent application filed on Sep. 30, 2011 (Application No. 2011-217350), the entire contents thereof being incorporated herein by reference.

INDUSTRIAL APPLICABILITY

Since the polymerizable inorganic-particle dispersant of the invention itself is polymerizable and has a high refractive index and a high Abbe's number, the dispersant is suitable for use as an optical material. Furthermore, the polymerizable inorganic-particle dispersant of the invention can evenly disperse inorganic particles, such as metal oxide nanoparticles having a particle diameter of 1-10 nm, to thereby form inorganic-organic composite particles. The dispersant hence makes it possible to attain an increase in refractive index and an increase in Abbe's number while maintaining transparency.

Consequently, the inorganic-organic resin composite material produced from such inorganic-organic composite particles can be applied to optical applications where a high refractive index and a high Abbe's number are required, such as the displays of portable digital assistants or the like, optical lenses, microlenses, switches, lightguide sheets, lightguide plates, optical waveguides, and optical circuits.

The invention claimed is:

1. A polymerizable inorganic-particle dispersant, comprising a compound which includes the following functional groups A, B, and Q:
   A: a polymerizable functional group;
   B: a carboxyl group, an oxo acid group containing phosphorus, or an oxo acid group containing sulfur; and
   Q: a sulfur-containing divalent or more cycloaliphatic hydrocarbon group optionally containing a hetero atom other than sulfur,
   wherein a proportion of sulfur atoms contained in the polymerizable inorganic-particle dispersant is 20% by mass or higher and 70% by mass or less, in terms of sulfur atom content.

2. The polymerizable inorganic-particle dispersant according to claim 1, wherein:
   the compound including the functional groups A, B, and Q is a compound represented by the following formula (I) or (II):

$A^1$ represents a polymerizable functional group,
$B^1$ represents a carboxyl group, an oxo acid group containing phosphorus, or an oxo acid group containing sulfur,
$Q^1$ represents a sulfur-containing cycloaliphatic hydrocarbon group which has a valence of (n1+m1) and may contain a hetero atom other than sulfur,
n1 and m1 each independently represent an integer of 1-10, and
with the proviso that when n1 and m1 are integers of 2 or larger, the multiple $A^1$ or $B^1$ moieties present in the molecule may be the same or different; and

$A^2$ represents a polymerizable functional group,
$B^2$ represents a phosphorus-containing oxo acid group having a valence of m2,
$Q^2$ represents a sulfur-containing cycloaliphatic hydrocarbon group which has a valence of (n2+1) and may contain a hetero atom other than sulfur;
n2 represents an integer of 1-10,
m2 represents an integer of 2-10, and with the proviso that the multiple $A^2$ or $Q^2$ moieties present in the molecule may be the same or different.

3. The polymerizable inorganic-particle dispersant according to claim 2, wherein $Q^1$ in formula (I) or $Q^2$ in formula (II) respectively is a group represented by the following formula (III) or a group represented by the following formula (IV):

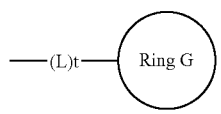  (III)

ring G represents a saturated, 3- to 8-membered monocycle or bridged ring, or represents a fused ring or spiro ring comprising two or three monocycles or bridged rings bonded together, wherein part of methylene groups constituting the ring has been replaced with a divalent group comprising a sulfur atom, and part of the methylene groups constituting the ring may further include a divalent group comprising an oxygen atom, a nitrogen atom, or a phosphorus atom, L represents a direct bond, a sulfide group, an ether group, or an aliphatic hydrocarbon group which may have a hetero atom, and the multiple L moieties contained in the molecule may be the same or different, and t is (n1+m1) when the formula (III) is Q1, or is (n2+1) when the formula (III) is Q2;

  (IV),

R represents a hydrogen atom or a hydrocarbon group which optionally comprise a hetero atom, E represents a sulfur atom or an oxygen atom, p represents an integer of 1-3, q represents an integer of 1-3, r represents 0 or 1, multiple R moieties contained in the molecule may be the same or different, and S, $CR_2$, and E in formula (IV) are bonded in any sequence.

4. The polymerizable inorganic-particle dispersant according to claim 3, wherein the functional group Q comprises the hetero atom other than sulfur atom which is any of an oxygen atom, a phosphorus atom, and a nitrogen atom.

5. The polymerizable inorganic-particle dispersant according to claim 1, wherein the sulfur-containing cycloaliphatic hydrocarbon group comprises at least one of a dithiane ring, a dithiolane ring, a trithiolane ring, a thiaspiro ring, a dithiaspiro ring, a trithiaspiro ring, a tetrathiaspiro ring, a dithietane ring, a thiirane ring, and a thiolane ring.

6. The polymerizable inorganic-particle dispersant according to claim 2, wherein the sulfur-containing cycloaliphatic hydrocarbon group comprises at least one of a dithiane ring, a dithiolane ring, a trithiolane ring, a thiaspiro ring, a dithiaspiro ring, a trithiaspiro ring, a tetrathiaspiro ring, a dithietane ring, a thiirane ring, and a thiolane ring.

7. The polymerizable inorganic-particle dispersant according to claim 5, wherein the sulfur-containing cycloaliphatic hydrocarbon group contains a sulfur-containing chain aliphatic hydrocarbon group as a substituent.

8. The polymerizable inorganic-particle dispersant according to claim 1, wherein the polymerizable functional group A is any of a (meth)acrylic group, an oxirane group, a thiirane group, and an isocyanate group.

9. The polymerizable inorganic-particle dispersant according to claim 1, which has a refractive index of 1.62 or higher.

10. The polymerizable inorganic-particle dispersant according to claim 1, which has an Abbe's number of 40 or higher.

11. Inorganic-organic composite particles, comprising the polymerizable inorganic-particle dispersant according to claim 1 and inorganic particles.

12. The inorganic-organic composite particles according to claim 11, wherein the inorganic particles are inorganic particles having a refractive index of 2.0 or higher.

13. The inorganic-organic composite particles according to claim 11, wherein the inorganic particles are inorganic particles having a diameter of 1-10 nm.

14. The inorganic-organic composite particles according to claim 11, wherein a content of the inorganic particles is 20-90% by mass based on the polymerizable inorganic-particle dispersant.

15. A dispersion, comprising the inorganic-organic composite particles according to claim 11 and a dispersion medium.

16. The dispersion according to claim 15, which further comprises a polymerizable monomer.

17. An inorganic-organic resin composite material obtained by curing the inorganic-organic composite particles according to claim 11.

18. An optical material, comprising the inorganic-organic resin composite material according to claim 17.

19. The optical material according to claim 18, which is an optical circuit.

20. The optical material according to claim 18, which is an optical waveguide.

21. The optical material according to claim 18, which is a lens.

22. A compound, comprising functional groups A, B, and Q:

A: a polymerizable functional group;

B: a carboxyl group, an oxo acid group containing phosphorus, or an oxo acid group containing sulfur; and Q: a sulfur-containing divalent or more cycloaliphatic hydrocarbon group optionally containing a hetero atom other than sulfur, wherein a proportion of sulfur atoms contained in the polymerizable inorganic-particle dispersant is 20% by mass or higher and 70% by mass or less, in terms of sulfur atom content.

23. Inorganic-organic composite particles, comprising a polymerizable inorganic-particle dispersant comprising a compound which includes the following functional groups A, B, and Q:

A: a polymerizable functional group;

B: a carboxyl group, an oxo acid group containing phosphorus, or an oxo acid group containing sulfur; and Q: a sulfur-containing divalent or more cycloaliphatic hydrocarbon group optionally containing a hetero atom other than sulfur.

* * * * *